(12) United States Patent
Collins et al.

(10) Patent No.: US 11,772,085 B2
(45) Date of Patent: *Oct. 3, 2023

(54) FAR SUPERIOR OXIDATION CATALYSTS BASED ON MACROCYCLIC COMPOUNDS

(71) Applicant: Carnegie Mellon University, Pittsburgh, PA (US)

(72) Inventors: Terrence James Collins, Pittsburgh, PA (US); Matthew Alan DeNardo, Pittsburgh, PA (US); Genoa Rose Warner, Pittsburgh, PA (US); Scott Wallace Gordon-Wylie, Woodstock, VT (US); William Chadwick Ellis, Bartlesville, OK (US); Yogesh Somasundar, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/113,162

(22) Filed: Dec. 7, 2020

(65) Prior Publication Data

US 2021/0086171 A1 Mar. 25, 2021

Related U.S. Application Data

(63) Continuation of application No. 15/762,937, filed as application No. PCT/US2016/053105 on Sep. 22, 2016, now Pat. No. 10,926,248.

(Continued)

(51) Int. Cl.
*B01J 31/18* (2006.01)
*C07D 281/00* (2006.01)
(Continued)

(52) U.S. Cl.
CPC ........ *B01J 31/1835* (2013.01); *C07D 281/00* (2013.01); *B01J 2531/0238* (2013.01);
(Continued)

(58) Field of Classification Search
None
See application file for complete search history.

(56) References Cited

U.S. PATENT DOCUMENTS 5,847,120 A 12/1998 Collins et al.
5,853,428 A 12/1998 Collins et al.
(Continued)

OTHER PUBLICATIONS

Collins (Accounts of Chemical Research, 2002, 35(9), 784-790 (Year: 2002).*

(Continued)

*Primary Examiner* — Yun Qian
(74) *Attorney, Agent, or Firm* — K&L Gates LLP

(57) ABSTRACT

An especially robust compound and its derivative metal complexes that are approximately one hundred-fold superior in catalytic performance to the previously invented TAML analogs is provided having the formula (I) wherein $Y_1$, $Y_2$, $Y_3$ and $Y_4$ are oxidation resistant groups which are the same or different and which form 5- or 6-membered rings with a metal, M, when bound to D; at least one Y incorporates a group that is significantly more stable towards nucleophilic attack than the organic amides of TAML activators; D is a metal complexing donor atom, preferably N; each X is a position for addition of a labile Lewis acidic substituent such as (i) H, deuterium, (ii) Li, Na, K, alkali metals, (iii) alkaline earth metals, transition metals, rare earth metals, which may be bound to one or more than one D, (iv) or is unoccupied with the resulting negative charge being balanced by a nonbonded counter-action; at least one Y may contain a site that is labile to acid dissociation, providing a mechanism for
(Continued)

1

2 shortening complex lifetime. The new complexes deliver catalytic performances that promise to revolutionize multiple oxidation technology spaces including water purification.

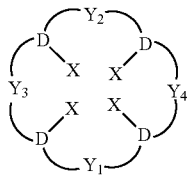

(I)

24 Claims, 25 Drawing Sheets

Related U.S. Application Data

(60) Provisional application No. 62/233,070, filed on Sep. 25, 2015.

(51) Int. Cl.
*D21C 9/10* (2006.01)
*C07F 1/00* (2006.01)
*C07F 3/00* (2006.01)
*C07F 15/02* (2006.01)

(52) U.S. Cl.
CPC .............. *C07F 1/005* (2013.01); *C07F 3/003* (2013.01); *C07F 15/025* (2013.01); *D21C 9/10* (2013.01)

(56) References Cited

U.S. PATENT DOCUMENTS

| | | |
|---|---|---|
| 6,051,704 A | 4/2000 | Gordon-Wylie et al. |
| 6,054,580 A | 4/2000 | Collins et al. |
| 6,685,914 B1 | 2/2004 | Liu |
| 6,992,184 B2 | 1/2006 | Carina et al. |
| 7,060,818 B2 | 6/2006 | Horwitz et al. |
| 8,584,757 B2 | 11/2013 | Reyes |
| 8,722,881 B2 | 5/2014 | Ghosh et al. |
| 10,926,248 B2 | 2/2021 | Collins et al. |
| 2004/0226104 A1 | 11/2004 | Vogt et al. |
| 2012/0329680 A1 | 12/2012 | Sengupta et al. |
| 2013/0287671 A1 | 10/2013 | Murray et al. |

OTHER PUBLICATIONS

Warner et al., Bioinspired, Multidisciplinary, Iterative Catalyst Design Creates the Highest Performance Peroxidase Mimics and the Field of Sustainable Ultradilute Oxidation Catalysis (SUDOC), ACS Catalysis, Jul. 9, 2019, 9, 8, 7023-7037. Abstract only.
DeNardo et al., Unifying Evaluation of the Technical Performances of Iron-Tetra-amido Macrocyclic Ligand Oxidation Catalysts, J. Am. Chem. Soc., 2016, 138, 9, pp. 2933-2936. Abstract only.
International Search Report and Written Opinion for Application No. PCT/US2016/053105, dated Oct. 31, 2016.

* cited by examiner

5555 I Macrocycles

5556 III Macrocycles

5556 IV Macrocycles

5566 I Macrocycles

5656 Macrocycles (cont.)

5666 Macrocycles (cont.)

6666 Macrocycles

6666 Macrocycles (cont.)

FAR SUPERIOR OXIDATION CATALYSTS BASED ON MACROCYCLIC COMPOUNDS

CROSS-REFERENCE TO RELATED APPLICATIONS

This application is a continuation Application of U.S. patent application Ser. No. 15/762,937, entitled FAR SUPERIOR OXIDATION CATALYSTS BASED ON MACROCYCLIC COMPOUNDS, filed on Mar. 23, 2028, which is a U.S. National Stage Entry under 35 U.S.C. § 371 of International Patent Application No. PCT/US2016/053105, entitled FAR SUPERIOR OXIDATION CATALYSTS BASED ON MACROCYCLIC COMPOUNDS, filed Sep. 22, 2016, which claims the benefit under 35 U.S.C. § 119(e) of U.S. Provisional Patent Application Ser. No. 62/233,070, entitled FAR SUPERIOR. OXIDATION CATALYSTS BASED ON MACROCYCLIC COMPOUNDS, filed Sep. 25, 2015, the entire disclosures of which are hereby incorporated by reference herein.

FIELD OF THE INVENTION

This invention relates to metal chelate complexes for serving as oxidation catalysts, and more particularly, to the design of macrocyclic catalytic activators of common oxidizing agents that far outperform the previous leaders in this technology space, namely "TAML Activators."

BACKGROUND

Macrocyclic tetradentate ligand metal complex activators, invented at Carnegie Mellon University and sold commercially as TAML® activators, are long-lived, fully functional mimics of the great families of oxidizing enzymes, namely the peroxidase enzymes (See U.S. Pat. Nos. 5,847,120; 5,853,428; 5,876,625; 6,054,580; 6,051,704; 6,099,586; 6,011,152; 6,100,394; 6,136,223; 6,241,779, and 6,992,184, collectively, the "Collins' Group Patents," each of which is incorporated herein by reference). For many years, the studies to make ever more robust TAML® catalysts followed the same design hypothesis that led to TAML® activators in the first place; that the functioning catalysts were being inactivated by oxidative degradation of the most vulnerable site in the macrocyclic ligand systems and that by finding and strengthening the most oxidatively vulnerable site, a superior catalyst would be produced.

At the same time as that iterative design process was being followed to improve the performance of TAML® catalysts, the mechanisms of TAML® catalyst behavior were studied and a set of Technical Performance Parameters (referred to herein as "Techperps") was developed that eventually cast doubt on the original design hypothesis for certain applications. While TAML activators remain impressive catalysts for the activation of numerous oxidizing agents and work well enough to allow, for example, micropollutants (MPs, a term for any pollutant that has an adverse effect at very small concentrations, typically in the range of parts per trillion to low parts per billion) to be degraded in water with catalyst concentrations in the low nanomolar regime ($\leq 80$ nM), it was found that the macrocyclic tetraamido ligand catalysts run into a stability wall of non-oxidative decay that cannot be escaped.

BRIEF SUMMARY OF THE INVENTION

TAML activators are iteratively invented oxidation catalysts that advanced based on the hypothesis that catalyst lifetimes were limited by destructive oxidation processes caused by the aggressive oxidizing conditions of functioning TAML processes. Over more than a decade of following this hypothesis, we were unable to rationalize a stability wall and thus were unable to find iterative design steps that could break through it. The present inventions arise from a discovery of the fact that our fundamental hypothesis was wrong. The overarching challenge solved by the inventions of this patent has been to achieve new composition of matter catalyst systems that escape the discovered non-oxidative decomposition processes, the nature of which was previously unknown.

The desired ligands and derivative far superior catalyst performances are met by the macrocyclic tetradentate compounds described herein.

The compounds have the general structure

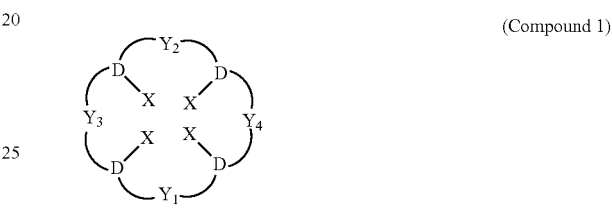

(Compound 1)

wherein:

D is an N donor atom; and each X is a position for addition of a labile Lewis acidic substituent such as (i) H, deuterium, (ii) Li, Na, K, other alkali metals, or (iii) alkaline earth metals, transition metals, rare earth metals, which may be bound to one or more than one D, or (iv) is unoccupied with the resulting negative charge being balanced by a non-bonded countercation.

As used in Compound 1, $Y_1$, $Y_2$, $Y_3$ and $Y_4$ are each independently selected from the group consisting of

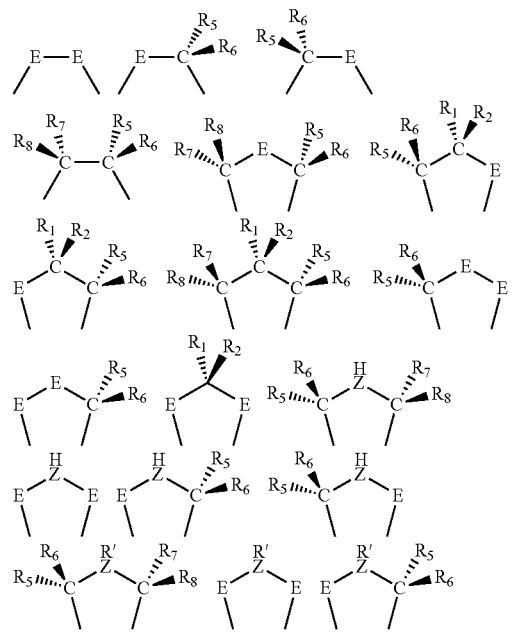

-continued

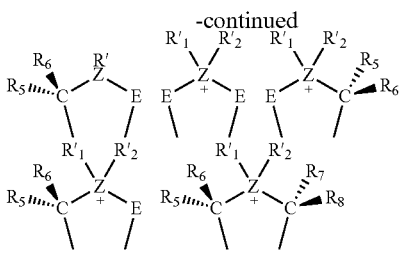

wherein:
E is selected from the groups consisting of $S(=Q)_2$, $S(=Q)R'_2$, $S(=Q)$, $P(=Q)R'$, $PR'_3$ and $C=Q$, where Q is oxygen or $ZR'$, wherein at least one E in at least one Y is more stable towards nucleophilic attack than $C=Q$ and is selected from the group consisting of $S(=Q)_2$, $S(=Q)R'_2$, $S(=Q)$, $P(=Q)R'$ or $PR'_3$ and is directly attached to one D in said Compound 1;

Z is selected from the group consisting of O, S (where there may or may not be an R' or H substituent), N, P, and As (where for N, P, and As one or two R's, designated $R'_1$ and $R'_2$, may be present); and R' is selected from the group consisting of (i) H, deuterium, (ii) Li, Na, K, other alkali metals, (iii) alkaline earth metals, transition metals, rare earth metals, (iv) oxygen, hydroxyl, halogen, a nitrogen-containing group, a carbon-containing group selected from the group consisting of alkyl, alkenyl, alkynyl, aryl, alkoxy, phenoxy, halogenated alkyl, halogenated aryl, halogenated alkenyl, halogenated alkynyl, perhaloalkyl, perhaloaryl, a substituted or unsubstituted cycloalkyl ring, a substituted or unsubstituted cycloalkenyl ring, a substituted or unsubstituted saturated heterocyclic ring containing oxygen, a Periodic Table Group 16 element, nitrogen, a Periodic Table Group 15 element, and a substituted or unsubstituted unsaturated heterocyclic ring containing any such elements.

$R'_1$ and $R'_2$ in Z of the $Y_1$, $Y_2$, $Y_3$ and $Y_4$ units are linked or nonlinked and each is independently selected from the group consisting of substituents which are unreactive, form strong bonds intramolecularly within said $R'_1$ and $R'_2$ and with the Z of the Y unit to which each is bound, are unable due to size to interact with a metal center when X is occupied by a metal, and may also be sterically hindered and/or conformationally hindered to further restrict oxidative degradation of a metal complex of the compound when the complex is in the presence of an oxidizing agent, or together with an R substituent or two R substituents on an adjacent carbon, E or Z in the same Y unit, form a mono- or poly-substituted or unsubstituted saturated or unsaturated ring. By way of example, $R'_1$ and $R'_2$ may be selected from hydrogen or deuterium, which may be labile to acid dissociation, alkyl, aryl, halogen, haloalkyl, perhaloalkyl, haloaryl, perhaloaryl, particularly methyl, ethyl, $CF_3$, substituted or unsubstituted-carbazole, or amino, substituted amino, amido (—NHCOR, —NRCOR, —NHSO$_2$R, —NRSO$_2$R, —NHPO$_2$R$^-$, NRPO$_2$R$^-$, NHPO(OR)R, NRPO(OR)R), fully oxidized or partially oxidized or substituted or unsubstituted carboxylic acid derivatives including, but not limited to, carboxylate (—CO$_2^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—O$_3^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$)), phosphines (—PR$_3$), nitrile, nitro, hydroxyl, and combinations thereof, or may form, together with the Z atom to which both are bound, substituted or unsubstituted three-, four-, five- or six-membered ring, such as a substituted or unsubstituted-aziridine, -azetidine, -pyrrolidine, or -piperidine.

$R_1$ and $R_2$ are linked or nonlinked and each is independently selected from the group consisting of substituents which form strong bonds intramolecularly within said $R_1$ and $R_2$ and with the carbon of the Y unit to which each is bound, which in the cases of H or D may be labile to acid dissociation, are unable due to size to interact with a metal center when X is occupied by a metal, are sterically hindered, conformationally hindered to further restrict oxidative degradation of a metal complex of the compound when the complex is in the presence of an oxidizing agent, or together with an R substituent or two R substituents on an adjacent carbon, E or Z in the same Y unit, form a mono- or poly-substituted or unsubstituted saturated or unsaturated ring. By way of example, $R_1$ and $R_2$ may be selected from hydrogen or deuterium, which may be labile to acid dissociation, alkyl, aryl, halogen, haloalkyl, perhaloalkyl, haloaryl, perhaloaryl, particularly methyl, ethyl, or $CF_3$, substituted or unsubstituted-carbazole, carboxyl, amino, substituted amino, amido (—NHCOR, —NRCOR, —NHSO$_2$R, —NRSO$_2$R, —NHPO$_2$R$^-$, —NRPO$_2$R$^-$, —NHPO(OR)R, NRPO(OR)R), fully oxidized or partially oxidized or substituted or unsubstituted carboxylic acid derivatives including, but not limited to, carboxylate (—O$_2^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$)), phosphines (—PR$_3$), nitrile, nitro, hydroxyl, alkoxy, aryloxy, a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring, and combinations thereof, or may form, together with the carbon atom to which both are bound, substituted or unsubstituted three-, four-, five- or six-membered ring, such as a substituted or unsubstituted-cyclopropyl, -cyclobutyl, -cyclopentyl including but not limited to dibenzocyclopentyl, or cyclohexyl, or together with a substituent on an adjacent E in the same Y unit form a mono- or poly-substituted or unsubstituted saturated or unsaturated ring, or joining with its paired R substituent together with a substituent on an adjacent E in the same Y unit form a mono- or poly-substituted or unsubstituted saturated or unsaturated ring.

Although methyl or a substituent, such as hydrogen, too small to reach the metal center when complexed with a metal, or a substituent that is conformationally or sterically hindered from reaching the iron center is preferred in the $R'_1$, $R'_2$, $R_1$, or $R_2$ positions, an advantage to including alkyls longer than methyl in the $R'_1$, $R'_2$, $R_1$, or $R_2$ positions is in the event that these positions are used, instead of $R_5$, $R_6$, $R_7$, or $R_8$, as a site to append hydrophobic chains to make the compound soluble in hydrophobic solvents as may be done, for example, with a cyclohexyl fused ring at $R_5$ and $R_6$. The $R'_1$, $R'_2$, $R_1$, or $R_2$ sites could be used as an attachment point to a solid support but the aromatic ring is believed to be the best location for this attachment point through either a nitrogen atom bonded to the ring or amide, sulfonamide, or phosphonamide in which case the respective carbon, sulfur, or phosphorous atom is bound to the ring. The carboxylic, sulfonic, and phosphonic acid derivative substituents for the $R'_1$, $R'_2$, $R_1$, $R_2$, $R_5$, $R_6$, $R_7$, and $R_8$ positions may serve, for example, as attachment points for solid supports, though other uses for them may be of interest.

$R_5$ and $R_6$, and, $R_7$ and $R_8$, are each (i) independently selected from the group consisting of hydrogen, deuterium, alkyl, alkenyl, alkynyl, aryl, alkoxy, phenoxy, oxylic, phenyl, halogen, halogenated alkyls, perhaloalkyl, halogenated aryls, perhaloaryl, halogenated alkenyl, halogenated alkynyl, alkylaryl, $CF_3$, $CH_2CF_3$, a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring, or amino, substituted amino, amido (—NHCOR, —NRCOR, —NHSO$_2$R, —NRSO$_2$R, —NHPO$_2$R$^-$, —NRPO$_2$R$^-$, —NRPO(OR)R, NRPO(OR)R), fully oxidized or partially oxidized or substituted or unsubstituted carboxylic acid derivatives including, but not limited to, carboxylate (—CO$_2$$^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3$$^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3$$^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR) (NR$_2$)), phosphines (—PR$_3$), nitrile, nitro, hydroxyl, alkoxy, aryloxy, and combinations thereof, or may combine to form a cycloalkyl, cycloalkenyl or aromatic ring or rings including polycyclic aromatic systems, which may contain at least one ring atom that is not carbon (ii) together with one or both R substituents on an adjacent carbon in the same Y unit, form a mono- or poly-substituted or unsubstituted saturated or unsaturated ring of which two carbons in the ring are adjacent carbons in the same Y unit, (iii) joining its paired R substituent together with one or both R substituents on an adjacent carbon in the same Y unit form a mono- or poly-substituted or unsubstituted saturated or unsaturated ring of which two carbons in the ring are adjacent carbons in the same Y unit, (iv) together with a paired R bound to the same carbon atom form a substituted or unsubstituted cycloalkyl or substituted or unsubstituted cycloalkenyl ring, (v) together with an R' substituent on an adjacent Z in the same Y unit form a mono- or poly-substituted or unsubstituted saturated or unsaturated ring, (vi) joining with its paired R substituent together with the R' substituent on an adjacent Z in the same Y unit, form a mono- or poly-substituted or unsubstituted saturated or unsaturated ring, (vii) together with a substituent on an adjacent E in the same Y unit form a mono- or poly-substituted or unsubstituted saturated or unsaturated ring, (viii) joining with its paired R substituent together with a substituent on an adjacent E in the same Y unit form a mono- or poly-substituted or unsubstituted saturated or unsaturated ring.

Another embodiment of the compound of the invention is shown by the formula

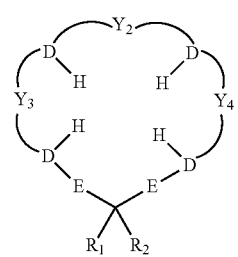

(Compound 2)

wherein $R_1$ and $R_2$ are linked or nonlinked, and each is independently selected from the group consisting of substituents which form strong bonds intramolecularly with said $R_1$ and $R_2$ and with the carbon to which each is bound, sterically hindered, and conformationally hindered such that in each case, oxidative degradation of a metal complex of the compound is restricted when the complex is in the presence of an oxidizing agent. The low conformational freedom of the $R_1$ and $R_2$ unit at least inhibits, and preferably prevents, attainment of conformers that are conducive to intramolecular oxidative degradation. Together with an R substituent or two R substituents on an adjacent carbon, E or Z in the same Y unit, $R_1$ and $R_2$ may form a mono- or poly-substituted or unsubstituted saturated or unsaturated ring. $R_1$ and $R_2$ may be selected from hydrogen or deuterium, which may be labile to acid dissociation, alkyl, aryl, halogen, haloalkyl, perhaloalkyl, haloaryl, perhaloaryl, particularly methyl, ethyl, or $CF_3$, amino, substituted amino, amido (—NHCOR, —NRCOR, —NHSO$_2$R, —NRSO$_2$R, —NHPO$_2$R$^-$, —NRPO$_2$R$^-$, —NHPO(OR)R, NRPO(OR)R), fully oxidized or partially oxidized or substituted or unsubstituted carboxylic acid derivatives including, but not limited to, carboxylate (—CO$_2$$^-$), carboxylic acids (—CO$_2$H), esters (CO$_2$R), amides (—CONH$_2$, —CONHR, —CONR$_2$), fully oxidized or partially oxidized substituted or unsubstituted sulfur substituents including, but not limited to, sulfonates (—SO$_3$$^-$, —SO$_2$(OH), —SO$_2$OR), sulfones (—SO$_2$R), and sulfonamides (—SO$_2$(NH$_2$)$^-$, —SO$_2$(NHR), —SO$_2$(NR$_2$)), fully oxidized or partially oxidized substituted or unsubstituted phosphorus substituents including, but not limited to, phosphates (—PO$_3$$^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonaxnides (—PO$_2$(NR$_2$)$^-$, —PO(NR$_2$)$_2$, —PO(OR) (NR$_2$)), phosphines (—PR$_3$), nitrile, nitro, hydroxyl, a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring, and combinations thereof, or may form, together with the carbon atom to which both are bound, a substituted or an unsubstituted three-, four-, five- or six-membered ring, such as a substituted or unsubstituted-cyclopropyl, -cyclobutyl, cyclopentyl (which may include, for example, an aromatic ring or rings like -dibenzocyclopentyl or polycyclic aromatic systems and which may contain least one ring atom that is not carbon), -cyclohexyl.

D is a donor atom, such as an oxidation resistant metal complexing atom, preferably N, bearing hydrogen where necessary.

E is selected from the groups consisting of $S(=Q)_2$, $S(=Q)R'_2$, $S(=Q)$, $P(=Q)R'$, $PR'_3$ and $C=Q$, where Q is oxygen or $ZR'$, wherein at least one E in at least one Y is more stable towards nucleophilic attack than $C=Q$ and is selected from the group consisting of $S(=Q)_2$, $S(=Q)R'_2$, $S(=Q)$, $P(=Q)R'$ or $PR'_3$ and is directly attached to one D in said Compound 1.

Z is selected from the group consisting of O, S (where there may or may not be an R' or H substituent), N, P, and As (where for N, P, and As one or two R's, designated $R'_1$ and $R'_2$, may be present).

R' is selected from the group consisting of (i) 14, deuterium, (ii) Li, Na, K, alkali metals, (iii) alkaline earth metals, transition metals, rare earth metals, (iv) oxygen, hydroxyl, halogen, or a nitrogen-containing group, a carbon-containing group selected from the group consisting of alkyl, alkenyl, alkynyl, aryl, alkoxy, phenoxy, halogenated alkyl, halogenated aryl, halogenated alkenyl, halogenated alkynyl, perhaloalkyl, perhaloaryl, a substituted or unsubstituted cycloalkyl ring, a substituted or unsubstituted cycloalkenyl ring, a substituted or unsubstituted saturated heterocyclic ring containing oxygen, a Periodic Table Group 16 element, nitrogen, a Periodic Table Group 15 element, and a substituted or unsubstituted unsaturated heterocyclic ring containing any such elements.

Further, $R'_1$ and $R'_2$ are the same or different, linked or nonlinked, and each is independently selected from the group consisting of substituents which are unreactive, form strong bonds intramolecularly within said and $R'_1$ and $R'_2$ with the Z of the Y unit to which each is bound, are unable due to size to interact with a metal center when X is occupied by a metal, and may also be sterically hindered and/or conformationally hindered to further restrict oxidative degradation of a metal complex of the compound when the complex is in the presence of an oxidizing agent, or together with an R substituent or two R substituents on an adjacent carbon, E or Z in the same Y unit, form a mono- or poly-substituted or unsubstituted saturated or unsaturated ring. By way of example, hydrogen or deuterium, which may be labile to acid dissociation, alkyl, aryl, halogen, haloalkyl, perhaloalkyl, haloaryl, perhaloaryl, particularly methyl, ethyl, $CF_3$, substituted or unsubstituted-carbazole, amino, substituted amino, substituted amido, amido (—NHCOR, —NRCOR, —NHSO$_2$R, —NRSO$_2$R, —NHPO$_2$R$^-$, —NRPO$_2$R$^-$, —NHPO(OR)R, NRPO(OR)R), fully oxidized or partially oxidized or substituted or unsubstituted carboxylic acid derivatives including, but not limited to, carboxylate (—CO$_2$$^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3$$^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3$$^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$),) phosphines (—PR$_3$), nitrile, and combinations thereof, or may form, together with the Z atom to which both are bound, substituted or unsubstituted three-, four-, five- or six-membered ring, such as a substituted or unsubstituted such as a substituted or unsubstituted -aziridine, -azetidine, -pyrrolidine, or -piperidine.

$Y_3$ is a unit joining the adjacent D atoms comprised of

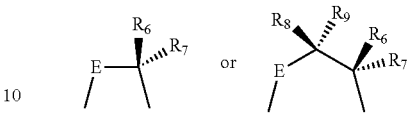

and $Y_4$ is a unit joining the adjacent D atoms comprised of

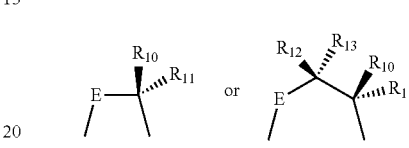

wherein $R_6$ and $R_7$, $R_8$ and $R_9$, and $R_{10}$ and $R_{11}$, and $R_{12}$ and $R_{13}$, pairwise and cumulatively, are the same or different and each (i) is selected from the group consisting of H or deuterium, alkyl, alkenyl, alkynyl, aryl, alkoxy, phenoxy, halogen, halogenated alkyl, halogenated aryl, halogenated alkenyl, halogenated alkynyl, $CF_3$, $CH_2CF_3$, amino, substituted amino, amido (—NHCOR, —NRCOR, —NHSO$_2$R, —NRSO$_2$R, —NRPO$_2$R$^-$, —NRPO$_2$R$^-$, —NRPO(OR)R, NPRO(OR)R), fully oxidized or partially oxidized or substituted or unsubstituted carboxylic acid derivatives including, but not limited to, carboxylate (—CO$_2$$^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3$$^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3$$^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$)), phosphines (—PR$_3$), nitrile, nitro, hydroxyl, and combinations thereof, a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring, and combinations thereof, (ii) together with one or both R substituents on an adjacent carbon in the same Y unit, form a mono- or poly-substituted or unsubstituted saturated or unsaturated ring of which two carbons in the ring are adjacent carbons in the same Y unit, (iii) joining with its paired R substituent together with one or both R substituents on an adjacent carbon in the same Y unit, form a mono- or poly-substituted or unsubstituted saturated or unsaturated ring of which two carbons in the ring are adjacent carbons in the same Y unit, (iv) together with a paired R bound to the same carbon atom, form a substituted or unsubstituted cycloalkyl or substituted or unsubstituted cycloalkenyl ring, (v) together with an R' substituent on an adjacent Z in the same Y unit, form a mono- or poly-substituted or unsubstituted saturated or unsaturated ring, (vi) joining with its paired R substituent together with the R' substituent on an adjacent Z in the same Y unit, form a mono- or polysubstituted or unsubstituted saturated or unsaturated ring, (vii) together with a substituent on an adjacent E in the same Y unit, form a mono- or poly-substituted or unsubstituted saturated or unsaturated ring, (viii) joining with its paired R substituent together with a substituent on an adjacent E in the same Y unit, form a mono- or poly-substituted or unsubstituted saturated or unsaturated ring.

$Y_2$ is a unit joining the adjacent D atoms comprised of:
(i)

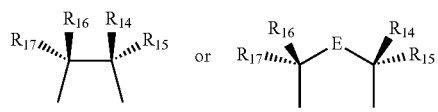

wherein $R_{14}$ through $R_{17}$ are the same or different and are hydrogen, deuterium, alkyl, aryl, halogen, halogenated alkyls, halogenated aryls, $CF_3$, $CH_2CF_3$, cycloalkyl, cycloalkenyl, alkynyl, alkylaryl, alkoxy, phenoxy, oxylic, phenyl, or amino, substituted amino, amido (—NHCOR, —NRCOR, —NHSO$_2$R, —NRSO$_2$R, —NHPO$_2$R$^-$, —NRPO$_2$R$^-$, —NRPO(OR)R, NRPO(OR)R), nitro, fully oxidised or partially oxidized or substituted or unsubstituted carboxylic acid derivatives including, but not limited to, carboxylate (—CO$_2$$^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3$$^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3$$^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$)), phosphines (—PR$_3$), nitrile, nitro, hydroxyl, aryloxy, and combinations thereof, or combine to form a cycloalkyl, cycloalkenyl or aromatic ring or rings including polycyclic aromatic systems, which may contain at least one ring atom that is not carbon, and combinations thereof, or together with a substituent on an adjacent E in the came Y unit, form a mono- or poly-substituted or unsubstituted saturated or unsaturated ring, or may join with its paired R substituent together with a substituent on an adjacent E in the same Y unit, form a mono- or poly-substituted or unsubstituted saturated or unsaturated ring, or together with an R' substituent on an adjacent Z in the same Y unit may form a mono- or poly-substituted or unsubstituted saturated or unsaturated ring, or may join with its paired R substituent together with the R' substituent on an adjacent Z in the same Y unit, form a mono- or poly-substituted or unsubstituted saturated or unsaturated ring, (ii) an aryl group wherein two adjacent positions are attached to two adjacent Ds of Compound 2 including

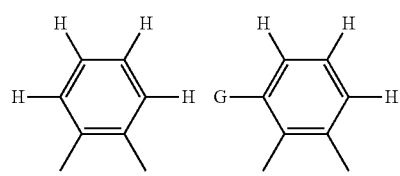

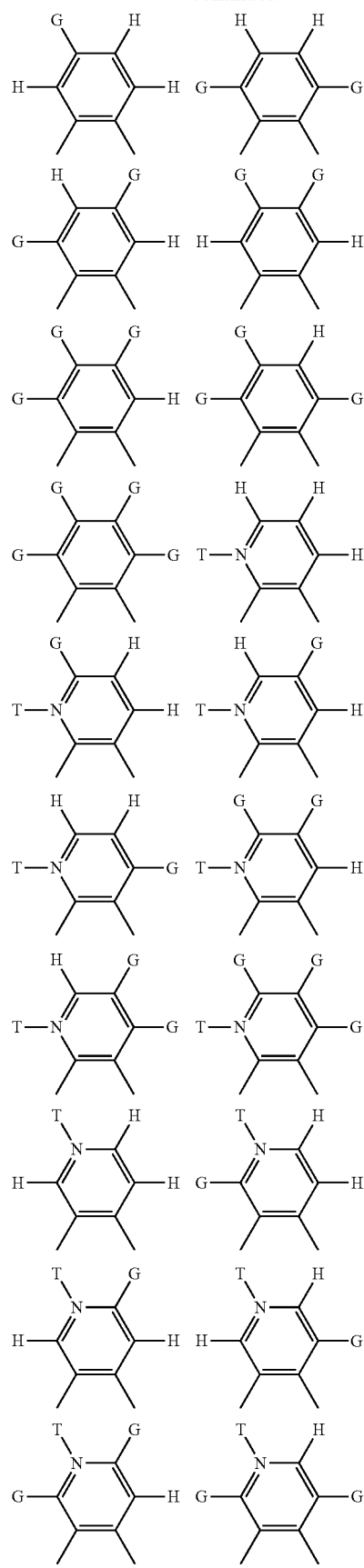

-continued

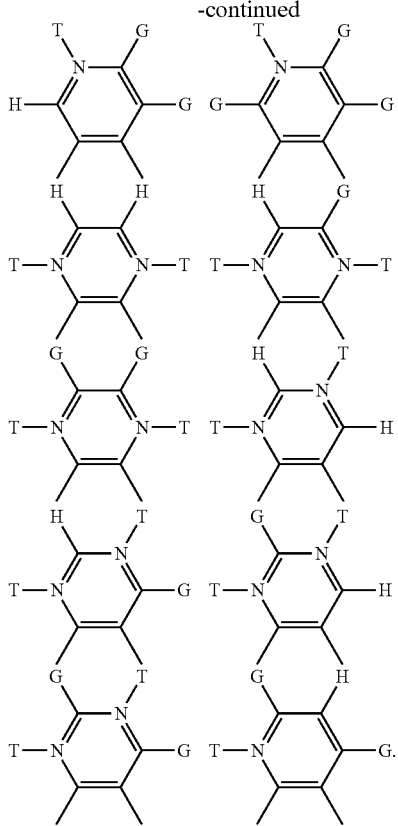

Each T in the foregoing benzene and substituted benzene structures listed for the $Y_2$ aryl group is the same or different and is one of an unoccupied position, or is occupied with one of a hydrogen, alkyl or haloalkyl.

Each G of the aryl group listed for $Y_2$ (i) is the same or different and comprises halogen, hydrogen, alkyl, cycloalkyl, alkenyl, cycloalkenyl, alkynyl, aryl, polycyclic aryl which may contain at least one ring atom that is not carbon, alkylaryl, phenoxy substituents, or amino, substituted amino, amido (—NHCOR, —NRCOR, —NHSO$_2$R, —NRSO$_2$R, —NHPO$_2$R$^-$, —NRPO$_2$R$^-$, —NHPO(OR)R, NRPO(OR)R), fully oxidized or partially oxidized or substituted or unsubstituted carboxylic acid derivatives including, but not limited to, carboxylate (—CO$_2$$^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3$$^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3$$^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$)), phosphines (—PR$_3$), nitrile, nitro, hydroxyl, alkoxy, aryloxy, siloxy, and combinations thereof, or combine to form a cycloalkyl, cycloalkenyl or aromatic ring or rings including polycyclic aromatic systems, which may contain at least one ring atom that is not carbon, (ii) together with one or more G substituents on adjacent carbons, form a mono- or poly-substituted or unsubstituted saturated or unsaturated ring, (iii) joins with an R substituent of one or more G substituents forms a mono- or poly-substituted or unsubstituted saturated or unsaturated ring (iv) together with an R' substituent on an adjacent Z in an adjacent Y unit, form a mono- or poly-substituted or unsubstituted saturated or unsaturated ring, (v) joins together with a substituent on an adjacent E in an adjacent Y unit, form a mono- or polysubstituted or unsubstituted saturated or unsaturated ring.

The present invention pertains to the novel changes to the macrocyclic structure giving new compositions of matter that increase the robustness of tetra-aza macrocyclic ligands such that one can obtain ligand systems that can better support catalysis, which is based on highly reactive metaloxo intermediates similar to those of the monooxygenases and peroxidases, than any small molecule replicas heretofore. The degradation chemistry that rendered the described changes necessary for improvement of catalytic performance was completely unexpected. Most significantly, the new systems described herein exhibit significantly improved technical performance with highly desirable O-atom transfer oxidants, especially peroxides, as well as electrodes and/or oxidized complexes regenerated by electrodes. These superior activities make these new systems available for a wide range of technological oxidation applications where there is significant promise of obtaining chemically- and cost-effective catalytic processes. The advantages over prior catalysts pertain not only to improved technical performances but also to superior cost performances.

Transition metal complexes of macrocyclic ligands have been used to catalyze oxidations in the past. Patented systems include tetra-amido macrocyclic ligands, porphyrins and phthalocyanines, halogenated porphyrins and ligands related to porphyrins, and substituted tricycloazanonane and related macrocycles. All of these systems differ fundamentally from the system of the present invention in significant ways. TAML® activators are the most functionally effective small molecule replicas of peroxidase enzymes in existence. For two decades, all TAML research in the pursuit of improved embodiments was focused systematically on trying to strengthen the most oxidatively vulnerable site in accordance with the hypothesis that TAML® activators are subject to oxidative decay. Following this design approach has led to catalysts of greater reactivity and utility as well as the development of kinetic methods to analyze the rates by which they (i) are oxidized to reactive forms by oxidizing agents such as hydrogen peroxide (associated with a rate constant $k_I$), (ii) attack targeted substrates (associated with a rate constant $k_{II}$), and (iii) decompose under functional conditions (associated with a rate constant $k_i$). Through the systematic application of these kinetic methods to a structurally diverse set of TAML activators, we have discovered, as described herein, that TAML® activators are not ultimately limited by oxidative decay as thought during this long period. Surprisingly, these studies indicate that TAML activator catalysis appears instead to be curtailed by nucleophilic hydrolytic and perhydrolytic attacks that occur at the carbonyl carbons of the amido-N ligands of the TAML® catalyst constructs. This discovery revealed a fatal flaw that could not be remedied within the TAML® system. Instead, new ligand systems that incorporate functionalities more resistant to nucleophilic attack than the C═O of amido-N ligands such as SO$_2$ or P(O)R yield macrocyclic tetradentate compounds that are overall less susceptible to the nucleophilic attack that underlies the newly discovered commanding vulnerability of TAML® activators.

Macrocyclic tetradentate compounds containing at least one sulfonamide or phosphonamide or related ligands comprising an E position and its adjacent D atom (as used in the structures for Compounds 1 and 2 above) were developed and found to provide many unexpected advantages. First, such ligands are anionic at D when bonding to a catalytic metal atom and are sufficiently highly donating such that the ligands of the present invention facilitate access to reactive high valent states of metals as with TAML® activators, a property that leads to efficient oxidative catalysis. While sulfonamides, as the test case, were substituted in order to confer increased protection against degradation to the catalysts, the deprotonated nitrogen atoms of sulfonamides and phosphonamides also generally donate less electron density than the corresponding amido-nitrogen atoms of TAML activators (lower $pK_a$'s), such that more oxidatively reactive activators have also been achieved by their incorporation into new compositions. Second, the macrocycles of the present invention can attain a high degree of both protection against decay and increased aggressiveness toward targeted substrates without recourse to halogen substituents—TAML activators are typically made more reactive by the incorporation of halogens at various positions on the macrocycles.

The new complexes are very active without incorporation of halogens, but can be made even more active with halogens. However, the nonhalogenated embodiments of the macrocyclic tetradentate activators are expected to have a higher degree of environmental friendliness as organohalogen compounds are often toxic, including developmentally toxic. Indeed, of seven TAML® activators subjected to zebrafish development assays, two of the three that were found to disrupt normal development were organochlorines. (see Lisa Truong et al., "Zebrafish Assays as Developmental Toxicity Indicators in the Green Design of TAML Oxidation Catalysts," Green Chem., 2013, 15, 2339-2343.) Moreover, for the large-scale water treatment uses anticipated for TAML activators, it had become a major concern that the best embodiments prior to the current inventions contain fluorine. Thus, water treatment use cannot escape the release of fluoride to aquatic systems and we were unsure that releasing either organofluorines or fluorine itself on large scales to water could be justified based on uncertainty associated with environmental safety. It is prudent for increasing the likelihood of environmental compatibility that catalysts for large-scale water treatment contain only biochemically common elements. While fluorine is not biochemically common, sulfur and phosphorus are. Thus, sulfonamides and phosphonamides can be used instead of halogens to decrease the electron density at the metal and render the so-changed catalysts more reactive than the TAML® analogues and this approach might also render them significantly less likely to be toxic. Third, macrocyclic tetradentate compounds containing one or more sulfonamide or phosphonamide at an ED site(s) of the present invention in place of the —(CO)N— moieties of TAML® activator embodiments (wherein E in all cases is (C=O) and D is N) should exhibit increased resistance to hydrolysis, perhydrolysis or other forms of nucleophilic attack and decay at each so-exchanged site. With each substitution of the four amido-N ligands in TAML activators, the number of susceptible sites is mathematically reduced by one, thereby removing an additional point of weakness to decomposing nucleophilic attack. Thus, each progressive substitution from one to four leads to a catalyst that is relatively more suitable for commercial use. However, the number of sulfonamide or phosphonamides can be manipulated for desired optimum outcomes by balancing the virtue of increased oxidative reactivity against the drawback of increased susceptibility to attack by nucleophiles at the remaining —(CO)N— moieties. This balance favors increased reactivity as each substitution results in one less susceptible site. Maximum augmentation of reactivity and the greatest resistance to nucleophilic attack are expected for the maximum substitution of four amido-N ligands with four sulfonamides or phosphonamides at an E-D site. The balances which can be achieved between reactivity, cost, environmental compatibility and lifetime are very important for optimization of processes, especially water treatment processes—one should not release a vigorous catalyst to the environment having too long a lifetime as it would be more likely to find toxic pathways and low dose adverse effects in the high biochemical complexity of natural aquatic systems. The new embodiments with sulfonamide and phosphonamide metal-binding groups greatly expand our flexibility in balancing through design optimal performance in water treatment plants with sufficiently rapid catalyst degradation to eliminate the potential of unknown adverse effects manifesting later in the environment.

In this regard, in the process of investigating the reactivities of the catalysts depicted in FIG. 1, we have discovered a novel and unanticipated catalyst inactivation pathway, which has never been observed for the amido-N macrocyclic activators. This pathway occurs when $R_1$ and/or $R_2$ are H or D and appears to be associated with acid dissociation of $H^+$ or $D^+$ rendering a much less stable catalyst system. When allowed to stand in deuterium oxide ($D_2O$), the $R_1$ and $R_2$ protons rapidly exchange to become $R_1$ and $R_2$ deuterons. Importantly, the exchange process must proceed by dissociation of $H^+$ or $D^+$ from the carbon atom bridging the sulfonamides. The deprotonated form turns out to be much more sensitive to decay under the conditions of oxidative catalysis. This "kill switch" is most turned on in the activated form of the catalyst and becomes more evident with increasing pH. Thus, at elevated pH the catalysts of Structure 2 having H or D as $R_1$ and/or $R_2$ decay more rapidly than expected by the comparative behavior of all other catalysts. Because the catalysts of Structure 2 are so reactive in water, oxidation catalysis proceeds so rapidly that, for example, in water purification most micropollutants are removed in minutes whereas the deprotonation "kill switch," a completely separate degradation process from those arising from nucleophilic attack at organic amido-N ligands, causes a slower degradation not evident in any prior TAML activator. Because of the balance manifested in these competing reactivities, this "kill switch" is an overall positive factor in the embodied compositions, allowing us to tune the rate of catalyst inactivation and bring added safety by providing a safeguard against release to the environment of catalysts that have already done their required job extraordinarily well. At elevated pHs, the inactivation of Structure 2 catalysts is very rapid, prescribing a method for catalyst disposal when necessary.

The tetradentate macrocyclic compound of the present invention is designed to be complexed with a metal, preferably a transition metal chosen from Groups 3 through 12 of the Periodic Table of the Elements, and most preferably a group 6 (Cr group), 7 (Mn group), 8 (Fe group), 9 (Co group), 10 (Ni group) or 11 (Cu group) transition metal, to form the corresponding chelate complex.

The invention therefore also includes a chelate complex of the formula

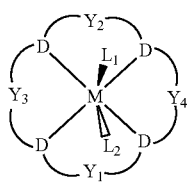

wherein M is a metal, D is a donor atom, preferably N, as defined for Compounds 1 and 2 above.

$Y_1$, $Y_2$, $Y_3$ and $Y_4$ function as oxidation and nucleophilic degradation-resistant components of the chelate system, may be the same or different, as defined for Compounds 1 and 2 above, and form, for example, five- to six-membered chelate rings with the adjacent DMD atoms.

$L_1$ and $L_2$ are optional ligands. In the preferred embodiment, one or both axial ligands, $L_1$ and $L_2$, bind to the metal M and at least one must be labile. The labile ligand(s) will dissociate in solution and will be replaced by a solvent molecule or the oxidant, most generally an O-atom transfer agent, but also any general oxidant that can serve to activate the metal ion to perform catalysis. The ligands may be the same or different. Preferred ligands include water, the hydroxide anion, the chloride-anion, halide ions in general, $CN^-$, ROH, $NH_3$, or any amine, carboxylate, phenol or phenoxide, nitrile, pyridine, ether, sulfoxide, ketone, phosphate, or carbonate.

It has been determined that the oxidation site in $Fe^{IV}$ complexes of aromatic ring-containing macrocycles can be manipulated by choice of the axial ligands as well as by the aromatic ring substituents. Strong donor anionic axial ligands ($CN^-$) favor a metal-centered oxidation i.e., $Fe^{IV}$, whereas weaker donors (e.g., $Cl^-$) favor a ligand-localized oxidation. The oxo intermediate form of the chelate complex system is believed to function as the actual catalytically active oxidized species in some applications and it is reactive at both the Fe(IV) and Fe(V) states, the latter being by far the most reactive. In others, the chelate system can be the sole site of oxidation, or the oxidation site can be mixed between the chelate system, the metal and any other ligand attached to the metal. Higher valences than Fe(V), including the engagement of either metal or ligand oxidation sites, may also participate in the catalysis.

The chelate group, $Y_1$, corresponds to the linking constituent of Compound 2 having the general formula $EC(R_1)(R_2)E$ wherein $R_1$, $R_2$ and E correspond to the groups described above for Compound 2.

$R_1$ and $R_2$ are key substituents in the design of the robust chelate complex and catalysts of the present invention. $R_1$ and $R_2$ are preferably hydrogen or deuterium, which may be labile to acid dissociation, alkyl, aryl, halogen, haloalkyl, perhaloalkyl, haloaryl, perhaloaryl, particularly methyl, ethyl, or $CF_3$, amino, substituted amino, amido (—NHCOR, —NRCOR, —NHSO$_2$R, —NRSO$_2$R, —NHPO$_2$R, —NRPO$_2$R$^-$, —NRPO(OR)R, NRPO(OR)R), fully oxidized or partially oxidized or substituted or unsubstituted carboxylic acid derivatives including, but not limited to, carboxylate (—CO$_2^-$), carboxylic acids (—CO$_2$H), (esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR) (NR$_2$)), phosphines (—PR$_3$), nitrile, nitro, a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring, and combinations thereof, or may form, together with the carbon atom to which both are bound, substituted or unsubstituted three-, four-, five- or six-membered ring, such as a substituted or unsubstituted-cyclopropyl, -cyclobutyl, -cyclopentyl including but not limited to dibenzocyclopentyl, or -cyclohexyl, or together with a substituent on an adjacent E in the same Y unit form a mono- or poly-substituted or unsubstituted saturated or unsaturated ring, or joining with its paired R substituent together with a substituent on an adjacent E in the same Y unit form a mono- or poly-substituted or unsubstituted saturated or unsaturated ring. Intramolecular reactions between an oxo ligand in a functioning catalytic system and the $R_1$ and $R_2$ substituents in prior art complexes where $R_1$ and $R_2$ substituents were ethyl groups, for example, may still contribute to the rapid degradation of the chelate ligand as has been heretofore experienced. See the Collins' Group Patents in addition to the nucleophilic processes discussed. The complexes described in the Collins' Group Patents which include oxidatively resistant substituents in the $R_1$ and $R_2$ positions have proven to be capable of productive catalysis. However, current work has indicated that nucleophilic attacks such as hydrolysis and perhydrolysis of the amides of these complexes contribute significantly to their inactivation under catalytic conditions (i.e. when exposed to an oxidant in systems containing nucleophiles, especially aqueous systems). The substitution of the sulfonamides, phosphonamides, or other blocking groups at the E position in the compounds described herein are selected to retard degradation ascribed to increased resistance to hydrolysis or perhydrolysis at the substituted position. As such, the inclusion of at least one sulfonamide or phosphonamide or related functionality in the new complexes decreases the number of susceptible sites for hydrolysis or perhydrolysis or other forms of nucleophilic decay while increasing reactivity leading to more productive and often cheaper catalytic processes.

The present invention also includes processes for the use of the complex defined above in the presence of an oxidant for performing of oxidation reactions. The complex may be present in substoichiometric amounts or in stoichiometric or near stoichiometric amounts or may be in excess.

The present invention also includes a process comprising exposing a target to an oxidant in the presence of the complex defined above. The oxidant may be halogen, halogen oxide, halogenoxoanion, elemental halogen, a peroxy compound, such as hydrogen peroxide, oxygen, air, oxygen in the presence of an adjunct, an electrode, a mediating compound in an oxidized state that is regenerated by an electrode, or photons that cause the complex to be oxidized by ejection of an electron or electrons, and combinations thereof. For example, the oxidant may be chosen from hydrogen peroxide, ozone, elemental chlorine, chlorine oxide, chlorine oxoanion, chlorine dioxide, hypochlorite, acidic species thereof, or combinations thereof. In the process, the complex may be added for the purpose of activating the oxidant for disinfection, sterilization, wound cleaning, fungicidal, bactericidal, insecticidal and herbicidal oxidations, or for sewerage and water treatment. The target may be a variety of organic or inorganic materials, including any oxidizable compound in water and micropollutants.

DETAILED DESCRIPTION OF THE INVENTION

Figure 1:
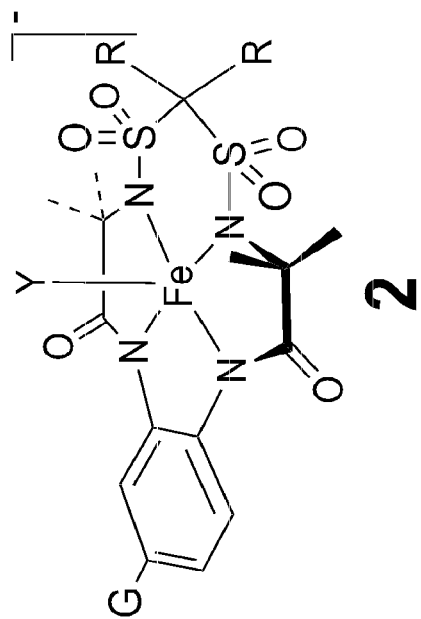
FIG. 1 compares the structures of a prior art macrocyclic tetraamido catalysts (Structure 1, 1a: G=H, R=CH$_3$, 1b: G=NO$_2$, R=CH$_3$) and improved macrocyclic sulfonamide catalysts (Structure 2, 2a: G=R=H, 2b: G=NO$_2$, R=H).
Figure 1:
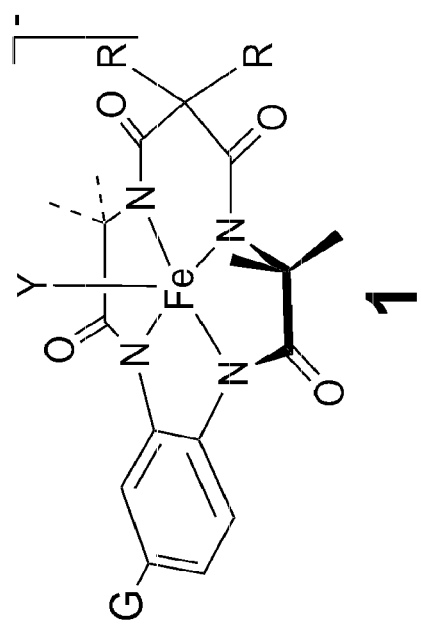

The set of Techperps developed to study catalyst performance is based on a general scheme for the mechanism of the catalytic cycle (see Scheme 1). The Techperps are: (1) the log of the rate constant associated with formation of the reactive intermediate (log k$_I$), (2) the log of the rate constant associated with oxidation of a targeted chemical (log k$_{II}$), and (3) the log of the rate constant associated with catalyst degradation (log k$_i$). The balance of the three Techperps, which can change with the reaction conditions, defines the comparative functional utilities of individual TAML® activators relative to all others under any common set of conditions. It has been learned, as disclosed herein, that the magnitudes of log k$_I$, log k$_{II}$ and log k$_i$ at the most environmentally significant pH of 7 for fifteen TAML® activators across four generations show reactivity differentials of six orders of magnitude in both k$_{II}$ and k$_i$ and >3 in k$_I$. When the individual Techperps are correlated against each other, e.g. log k$_i$ versus log k$_{II}$, linear dependencies are revealed in each correlation. This implies that a common property of TAML® activators controls all three Techperps via a common effect. Without wishing to be bound by theory, the common property is currently believed to be the Lewis acidity at the metal center of the catalyst. As used herein, TAML activators and amido-N activators refer to the heretofore available activators, prior to the improvement in the compound structure described herein.

These facts teach that while one can design TAML activators to be more reactive towards oxidizable substrates (i.e., increase log k$_{II}$) by increasing the Lewis acidity at the metal via addition of electron-withdrawing substituents to the macrocycle, this approach also increases the catalyst degradation rate (i.e., increases log k$_i$). Moreover, in a relationship common to each correlation, log k$_i$ and log k$_{II}$ have been found to be related linearly with a slope of approximately 1. This behavior is general over all variations of the 15 TAML catalysts studied in this way at pH 7, making it clear that the hypothesis that the research team had long been pursuing for making more reactive/longer lived TAML activators, i.e. that TAML activators decompose under operating conditions by oxidative decay, is wrong for TAML activators at pH 7, even although this very hypothesis was correct for all iterative catalyst design steps leading up to the point of invention of TAML activators. Moreover, the high catalytic activity displayed by TAML activators operating in aqueous solutions containing excess hydrogen peroxide led to the assumption that TAML activators were not subject to lifetime-limiting hydrolytic or perhydrolytic decay. Studies conducted at aggressive high pH conditions were particularly misleading as such nucleophilic degradation processes would be expected to be most rapid here. Without wishing to be bound by theory, it now seems that deprotonation at high pH of aqua ligands on the metal complex such as are found in aqueous solutions increases the negative charge on the complex. This negative charge is distributed over the catalyst masking the presence of such hydrolytic or perhydrolytic decay pathways by slowing these processes down. Regardless of the explanation, TAML activators clearly run into a stability wall of non-oxidative decay at neutral pH that cannot be escaped within the TAML activator family.

Again, without wishing to be bound by theory, it is believed that the controlling chemistries of these activator lifetimes are perhydrolysis and hydrolysis of the amide moieties in the macrocyclic tetraamido ligand systems. The body of prior art and the detailed scientific studies that led us to this unexpected revelation over the controlling chemistries of TAML activator design are signaled in the appended publication (Appendix 1 attached hereto and incorporated herein).

The preferred embodiment of the tetradentate macrocyclic compound of the present invention follows:

A macrocyclic tetradentate ligand having the structure

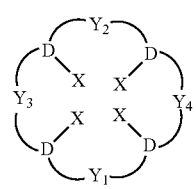

wherein:

D is a donor atom, preferably N; and each X is a position for addition of a labile Lewis acidic substituent such as (i) H, deuterium, (ii) Li, Na, K, other alkali metals, (iii) alkaline earth metals, transition metals, rare earth metals, which may be bound to one or more than one D, (iv) or is unoccupied with the resulting negative charge being balanced by a nonbonded countercation.

As used in Compound 1, $Y_1$, $Y_2$, $Y_3$ and $Y_4$ are each independently selected from the group consisting of

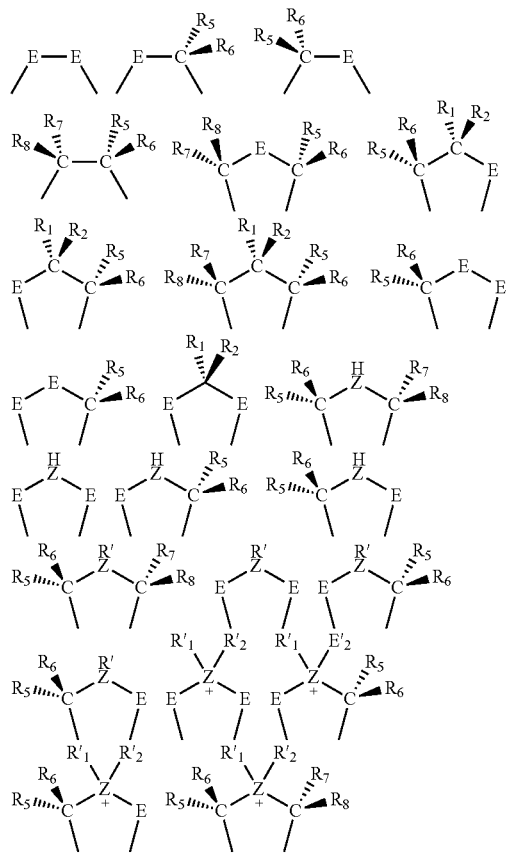

wherein:
- E is selected from the groups consisting of $S(=Q)_2$, $S(=Q)R'_2$, $S(=Q)$, $P(=Q)R'$, $PR'_3$ and $C=Q$, where Q is oxygen or $ZR'$, wherein at least one E in at least one Y is more stable towards nucleophilic attack than $C=Q$ and is selected from the group consisting of $S(=Q)_2$, $S(=Q)R'_2$, $S(=Q)$, $P(=Q)R'$ or $PR'_3$ and is directly attached to one D in said Compound 1;
- Z is selected from the group consisting of O, S (where there may or may not be an R' or H substituent), N, P, and As (where for N, P, and As one or two R's, designated $R'_1$ and $R'_2$, may be present);
- R' is selected from the group consisting of (i) H, deuterium, (ii) Li, Na, K, alkali metals, (iii) alkaline earth metals, transition metals, rare earth metals, (iv) oxygen, hydroxyl, halogen, a nitrogen-containing group, a carbon-containing group selected from the group consisting of alkyl, alkenyl, alkynyl, aryl, alkoxy, phenoxy, halogenated alkyl, halogenated aryl, halogenated alkenyl, halogenated alkynyl, perhaloalkyl, perhaloaryl, a substituted or unsubstituted cycloalkyl ring, a substituted or unsubstituted cycloalkenyl ring, a substituted or unsubstituted saturated heterocyclic ring containing oxygen, a Periodic Table Group 16 element, nitrogen, a Periodic Table Group 15 element, and a substituted or unsubstituted unsaturated heterocyclic ring containing any such elements;
- $R'_1$ and $R'_2$ are the same or different, linked or nonlinked, and each is independently selected from the group consisting of substituents which are unreactive, form strong bonds intramolecularly within said $R'_1$ and $R'_2$ and with the Z of the Y unit to which each is bound, are unable due to size to interact with a metal center when X is occupied by a metal, and may also be sterically hindered and/or conformationally hindered to further restrict oxidative degradation of a metal complex of the compound when the complex is in the presence of an oxidizing agent, or together with an R substituent or two R substituents on an adjacent carbon, E or Z in the same Y unit, form a mono- or poly-substituted or unsubstituted saturated or unsaturated ring; and,
- $R_1$ and $R_2$ are the same or different, linked or nonlinked, and each is independently selected from the group consisting of substituents which are form strong bonds intramolecularly within said $R_1$ and $R_2$ and with the carbon of the Y unit to which each is bound, which in the cases of H or D may be labile to acid dissociation, are unable due to size to interact with a metal center when X is occupied by a metal, sterically hindered, and/or conformationally hindered to further restrict oxidative degradation of a metal complex of the compound when the complex is in the presence of an oxidizing agent, or together with an R substituent or two R substituents on an adjacent carbon, E or Z in the same Y unit, form a mono- or poly-substituted or unsubstituted saturated or unsaturated ring.

$R'_1$ and $R'_2$, for example, may be selected from hydrogen or deuterium, which may be labile to acid dissociation, alkyl, aryl, halogen, haloalkyl, perhaloalkyl, haloaryl, perhaloaryl, particularly methyl, ethyl, $CF_3$, amino, substituted amino, amido (—NHCOR, —NRCOR, —NHSO$_2$R, —NRSO$_2$R, —NHPO$_2$R$^-$, —NRPO$_2$R$^-$, —NRPO(OR)R, NRPO(OR)R), fully oxidized or partially oxidized or substituted or unsubstituted carboxylic acid derivatives including, but not limited to, carboxylate (—CO$_2^-$), carboxylic acids (—CO$_2$H), (esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$)), phosphines (—PR$_3$), nitrile, nitro, hydroxyl, alkoxy, aryloxy, and combinations thereof, or may form, together with the carbon atom to which both are bound, substituted or unsubstituted three-, four-, five- or six-membered ring, such as a substituted or unsubstituted-cyclopropyl, -cyclobutyl, -cyclopentyl including but not limited to -dibenzocyclopentyl, or -cyclohexyl, carboxyl.

By way of example, $R_1$ and $R_2$ may be selected from hydrogen or deuterium, which may be labile to acid dissociation, alkyl, aryl, halogen, haloalkyl, perhaloalkyl, haloaryl, perhaloaryl, particularly methyl, ethyl, or $CF_3$, amino, substituted amino, substituted amino, amino (—NHCOR, —NRCOR, —NHSO$_2$R, —NRSO$_2$R, —NHPO$_2$R$^-$, —NRPO$_2$R$^-$, —NRPO(OR)R, NRPO(OR)R), fully oxidized or partially oxidized or substituted or unsubstituted carboxylic acid derivatives including, but not limited to, carboxylate (—CO$_2^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates ($-SO_3^-$, $-SO_2(OH)$, $-SO_2OR$), sulfones ($-SO_2R$), and sulfonamides ($-SO_2(NH_2)$, $-SO_2(NHR)$, $-SO_2(NR_2)$), fully oxidized or partially oxidized substituted or unsubstituted phosphorus substituents including, but not limited to, phosphates ($-PO_3^{2-}$, $-PO_2(OH)^-$, $-PO(OH)_2$), alkyl phosphate ($-PO_2(OR)^-$), phosphonate ($-PO(OR)_2$), phosphinate ($-PO(OR)R$), phosphine oxide ($-P(O)R_2$), phosphonamides ($-PO_2(NR_2)^-$, $-PO(NR_2)_2$, $-PO(OR)(NR_2)$,) phosphines ($-PR_3$), nitrile, nitro, hydroxyl, alkoxy, aryloxy, a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring, a substituted or unsubstituted unsaturated heterocyclic ring, and combinations thereof, or may form, together with the carbon atom to which both are bound, substituted or unsubstituted three-, four-, five- or six-membered ring, such as a substituted or unsubstituted-cyclopropyl, -cyclobutyl, -cyclopentyl including but not limited to dibenzocyclopentyl, or -cyclohexyl, such as a substituted or unsubstituted such as a substituted or unsubstituted -aziridine, -azetidine, -pyrrolidine, -piperidine including but not limited to substituted or unsubstituted-carbazole, or together with a substituent on an adjacent E in the same Y unit form a mono- or poly-substituted or unsubstituted saturated or unsaturated ring, or joining with its paired R substituent together with a substituent on an adjacent E in the same Y unit form a mono- or poly-substituted or unsubstituted saturated or unsaturated ring.

$R_5$ and $R_6$, and, $R_7$ and $R_8$, pairwise and cumulatively, are the same or different and each (i) is independently selected from the group consisting of hydrogen, deuterium, alkyl, alkenyl, alkynyl, aryl, alkoxy, phenoxy, oxylic, phenyl, halogen, halogenated alkyls, perhaloalkyl, halogenated aryls, perhaloaryl, halogenated alkenyl, halogenated alkynyl, alkylaryl, $CF_3$, $CH_2CF_3$, amino, substituted amino, amido (NHCOR, NRCOR, $-NHSO_2R$, $NRSO_2R$, $-NHPO_2R^-$, $-NRPO_2R^-$, $-NHPO(OR)R$, $NRPO(OR)R$), fully oxidized or partially oxidized or substituted or unsubstituted carboxylic acid derivatives including, but not limited to, carboxylate ($-CO_2^-$), carboxylic acids ($-CO_2H$), esters ($-CO_2R$), amides ($-CONH_2$, $-CONHR$, $-CONR_2$), and combinations thereof, fully oxidized or partially oxidized substituted or unsubstituted sulfur substituents including, but not limited to, sulfonates ($-SO_3^-$, $-SO_2(OH)$, $-SO_2OR$), sulfones ($-SO_2R$), and sulfonamides ($-SO_2(NH_2)$, $-SO_2(NHR)$, $-SO_2(NR_2)$), fully oxidized or partially oxidized substituted or unsubstituted phosphorus substituents including, but not limited to, phosphates ($-PO_3^{2-}$, $-PO_2(OH)^-$, $-PO(OH)_2$), alkyl phosphate ($-PO_2(OR)^-$), phosphonate ($-PO(OR)_2$), phosphinate ($-PO(OR)R$), phosphine oxide ($-P(O)R_2$), phosphonamides ($-PO_2(NR_2)^-$, $-PO(NR_2)_2$, $-PO(OR)(NR_2)$), phosphines ($-PR_3$), nitrile, nitro, hydroxyl, aryloxy, and combinations thereof, a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring, (ii) together with one or both R substituents on an adjacent carbon in the same Y unit, form a mono- or poly-substituted or unsubstituted saturated or unsaturated ring of which two carbons in the ring are adjacent carbons in the same Y unit, (iii) joining its paired R substituent together with one or both R substituents on an adjacent carbon in the same Y unit form a mono- or poly-substituted or unsubstituted saturated or unsaturated ring of which two carbons in the ring are adjacent carbons in the same Y unit, (iv) together with a paired R bound to the same carbon atom, forms a substituted or unsubstituted cycloalkyl or substituted or unsubstituted cycloalkenyl ring, (v) together with an R' substituent on an adjacent Z in the same Y unit, forms a mono- or poly-substituted or unsubstituted saturated or unsaturated ring, (vi) joining its paired R substituent together with the R' substituent on an adjacent Z in the same Y unit forms a mono- or poly-substituted or unsubstituted saturated or unsaturated ring, (vii) together with a substituent on an adjacent E in the same Y unit, form a mono- or poly-substituted or unsubstituted saturated or unsaturated ring, (viii) joining with its paired R substituent and a substituent on an adjacent E in the same Y unit, form a mono- or poly-substituted or unsubstituted saturated or unsaturated ring.

The preferred embodiment of Compound 1 has the structure

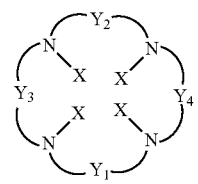

wherein each D is N. The remaining substituents are as described above.

An embodiment of the macrocyclic compound of the present invention, Compound 2, is a subset of Compound 1, wherein $Y_1$ comprises a carbon atom positioned between two Es, and has the structure:

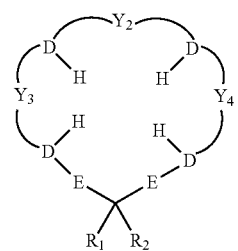

wherein $R_1$ and $R_2$ are the same or different, linked or nonlinked, and each is independently selected from the group consisting of substituents which form strong bonds intramolecularly with said $R_1$ and $R_2$ and with the cyclic carbon to which each is bound, may be sterically hindered and/or conformationally hindered such that oxidative degradation of a metal complex of the compound is restricted when the complex is in the presence of an oxidizing agent. The low conformational freedom of the species prevents attainment of conformers that are conducive to intramolecular oxidative degradation. $R_1$ and $R_2$ may be hydrogen or deuterium, which may be labile to acid dissociation, alkyl, aryl, halogen, haloalkyl, perhaloalkyl, haloaryl, perhaloaryl, particularly methyl, ethyl, or $CF_3$, amino, substituted amino, amido ($-NHCOR$, $-NRCOR$, $-NHSO_2R$, $-NRSO_2R$, $-NHPO_2R^-$, $-NRPO_2R^-$, $-NHPO(OR)R$, $NRPO(OR)R$), fully oxidized or partially oxidized or substituted or unsubstituted carboxylic acid derivatives including, but not limited to, carboxylate ($-CO_2^-$), carboxylic acids ($-CO_2H$), esters ($-CO_2R$), amides ($-CONH_2$, —CONHR, —CONR$_2$), and combinations thereof, fully oxidized or partially oxidized substituted or unsubstituted sulfur substituents including, but not limited to, sulfonates (—SO$_3^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$)), phosphines (—PR$_3$), nitrile, nitro, hydroxyl, alkoxy, aryloxy, a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring, and combinations thereof, or may form, together with the carbon atom to which both are bound, substituted or unsubstituted three-, four-, five- or six-membered ring, such as a substituted or unsubstituted-cyclopropyl, -cyclobutyl, -cyclopentyl including but not limited to dibenzocyclopentyl, or cyclohexyl, or together with a substituent on an adjacent E in the same Y unit form a mono- or poly-substituted or unsubstituted saturated or unsaturated ring, or joining with its paired R substituent together with a substituent on an adjacent E in the same Y unit form a mono- or poly-substituted or unsubstituted saturated or unsaturated ring;

D is a donor atom, such as an oxidation resistant metal complexing atom, preferably N, bearing hydrogen where necessary;

E is selected from the groups consisting of S(=Q)$_2$, S(=Q)R'$_2$, S(=Q), P(=Q)R', PR'$_3$ and C=Q, where Q is oxygen or ZR', wherein at least one E in at least one Y is more stable towards nucleophilic attack than C=Q and is selected from the group consisting of S(=Q)$_2$, S(=Q)R'$_2$, S(=Q), P(=Q)R' or PR'$_3$ and is directly attached to one D in said Compound 1;

Z is selected from the group consisting of O or S (where there may or may not be an R' or H substituent), or N, P, or As (where for N, P, or As one or two R's, designated R'$_1$ and R'$_2$, may be present);

R' is selected from the group consisting of (i) H, deuterium, (ii) Li, Na, K, alkali metals, (iii) alkaline earth metals, transition metals, rare earth metals, (iv) oxygen, hydroxyl, halogen, a nitrogen-containing group, a carbon-containing group selected from the group consisting of alkyl, alkenyl, alkynyl, aryl, alkoxy, phenoxy, halogenated alkyl, halogenated aryl, halogenated alkenyl, halogenated alkynyl, perhaloalkyl, perhaloaryl, a substituted or unsubstituted cycloalkyl ring, a substituted or unsubstituted cycloalkenyl ring, a substituted or unsubstituted saturated heterocyclic ring containing oxygen, a Periodic Table Group 16 element, nitrogen, a Periodic Table Group 15 element, and a substituted or unsubstituted unsaturated heterocyclic ring containing any such elements; and, R'$_1$ and R'$_2$ are the same or different, linked or nonlinked, and each is independently selected from the group consisting of substituents which are unreactive, form strong bonds intramolecularly within said R'$_1$ and R'$_2$ and with the Z of the Y unit to which each is bound, are unable due to size to interact with a metal center when X is occupied by a metal, and may also be sterically hindered and/or conformationally hindered to further restrict oxidative degradation of a metal complex of the compound when the complex is in the presence of an oxidizing agent, or together with an R substituent or two R substituents on an adjacent carbon, E or Z in the same Y unit, form a mono- or poly-substituted or unsubstituted saturated or unsaturated ring. By way of example, hydrogen or deuterium, which may be labile to acid dissociation, alkyl, aryl, halogen, haloalkyl, perhaloalkyl, haloaryl, perhaloaryl, particularly methyl, ethyl, CF$_3$, amino, substituted amino, substituted amino, amido (—NHCOR, —NRCOR, —NHSO$_2$R, —NRSO$_2$R, —NHPO$_2$R$^-$, —NRPO$_2$R$^-$, —NRPO(OR)R, NRPO(OR)R), fully oxidized or partially oxidized or substituted or unsubstituted carboxylic acid derivatives including, but not limited to, carboxylate (—CO$_2^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$),) phosphines (—PR$_3$), hydroxyl, nitrile, and combinations thereof, or may form, together with the carbon atom to which both are bound, substituted or unsubstituted three-, four-, five- or six-membered ring, such as a substituted or unsubstituted -aziridine, -azetidine, -pyrrolidine, -piperidine including but not limited to substituted or unsubstituted-carbazole.

Y$_3$ is a unit joining the adjacent D atoms comprised of

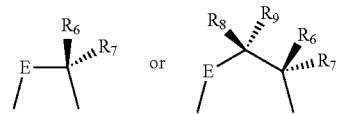

Y$_4$ is a unit joining the adjacent D atoms comprised of

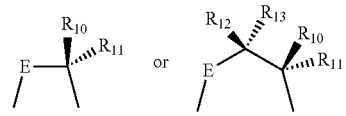

wherein R$_6$ and R$_7$, R$_8$ and R$_9$, and R$_{10}$ and R$_{11}$, and R$_{12}$ and R$_{13}$, pairwise and cumulatively, are the same or different and each (i) is selected from the group consisting of 1-1 or deuterium, alkyl, alkenyl, alkynyl, aryl, alkoxy, phenoxy, halogen, halogenated alkyl, halogenated aryl, halogenated alkenyl, halogenated alkynyl, CF$_3$, CH$_2$CF$_3$, amino, substituted amino, amido (—NHCOR, —NRCOR, —NHSO$_2$R, —NRSO$_2$R, —NHPO$_2$R$^-$, —NRPO$_2$R$^-$, —NHPO(OR)R, NRPO(OR)R), fully oxidized or partially oxidized or substituted or unsubstituted carboxylic acid derivatives including, but not limited to, carboxylate (—CO$_2^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3^-$, —SO$_2$(OH), —SO$_2$OR), sulfones (—SO$_2$R), and sulfonamides (—SO₂(NH₂), —SO₂(NHR), —SO₂(NR₂)), fully oxidized or partially oxidized substituted or unsubstituted phosphorus substituents including, but not limited to, phosphates (—PO₃²⁻, —PO₂(OH)⁻, —PO(OH)₂), alkyl phosphate (—PO₂(OR)⁻), phosphonate (—PO(OR)₂), phosphinate (—PO(OR)R), phosphine oxide (—P(O)R₂), phosphonamides (—PO₂(NR₂)⁻, —PO(NR₂)₂, —PO(OR)(NR₂)), phosphines (—PR₃), nitrile, nitro, hydroxyl, aryloxy, a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring, and combinations thereof, (ii) together with one or both R substituents on an adjacent carbon in the same Y unit, form a mono- or poly-substituted or unsubstituted saturated or unsaturated ring of which two carbons in the ring are adjacent carbons in the same Y unit, (iii) joining with its paired R substituent together with one or both R substituents on an adjacent carbon in the same Y unit, form a mono- or poly-substituted or unsubstituted saturated or unsaturated ring of which two carbons in the ring are adjacent carbons in the same Y unit, (iv) together with a paired R bound to the same carbon, atom form a substituted or unsubstituted cycloalkyl or substituted or unsubstituted cycloalkenyl ring, (v) together with an R' substituent on an adjacent Z in the same Y unit, form a mono- or poly-substituted or unsubstituted saturated or unsaturated ring, (vi) joins with its paired R substituent and the R' substituent on an adjacent Z in the same Y unit to form a mono- or poly-substituted or unsubstituted saturated or unsaturated ring, (vii) together with a substituent on an adjacent E in the same Y, unit form a mono- or poly-substituted or unsubstituted saturated or unsaturated ring, (viii) joins with its paired R substituent and a substituent on an adjacent E in the same Y unit to form a mono- or poly-substituted or unsubstituted saturated or unsaturated ring.

$Y_2$ is a unit joining the adjacent D atoms comprised of:
(i)

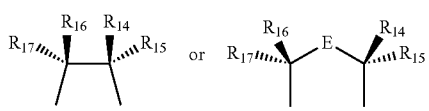

wherein $R_{14}$ through $R_{17}$ are the same or different and are H or deuterium, alkyl, aryl, halogen, halogenated alkyls, halogenated aryls, CF₃, CH₂CF₃, cycloalkyl, cycloalkenyl, alkynyl, alkylaryl, alkoxy, phenoxy, oxylic, phenyl, or amino, substituted amino, amido (—NHCOR, —NRCOR, —NHSO₂R, —NRSO₂R, —NHPO₂R⁻, —NRPO₂R⁻, —NHPO(OR)R, NRPO(OR)R), nitro, fully oxidized or partially oxidized or substituted or unsubstituted carboxylic acid derivatives including, but not limited to, carboxylate (—CO₂), carboxylic acids (—CO₂H), esters (—CO₂R), amides (—CONH₂, —CONHR, —CONR₂), and combinations thereof, fully oxidized or partially oxidized substituted or unsubstituted sulfur substituents including, but not limited to, sulfonates (—SO₃⁻, —SO₂(OH), —SO₂OR), sulfones (—SO₂R), and sulfonamides (—SO₂(NH₂), —SO₂(NHR), —SO₂(NR₂)), fully oxidized or partially oxidized substituted or unsubstituted phosphorus substituents including, but not limited to, phosphates (—PO₃²⁻, —PO₂(OH)⁻, —PO(OH)₂), alkyl phosphate (—PO₂(OR)⁻), phosphonate (—PO(OR)₂), phosphinate (—PO(OR)R), phosphine oxide (—P(O)R₂), phosphonamides (—PO₂(NR₂)⁻, —PO(NR₂)₂, —PO(OR)(NR₂)), phosphines (—PR₃), nitrile, nitro, hydroxyl, aryloxy, and combinations thereof, or may combine to form a cycloalkyl, cycloalkenyl or aromatic ring or rings including polycyclic aromatic systems, which may contain at least one ring atom that is not carbon, or (ii) an aryl group wherein two adjacent positions are attached to two adjacent Ds of Compound 2 including

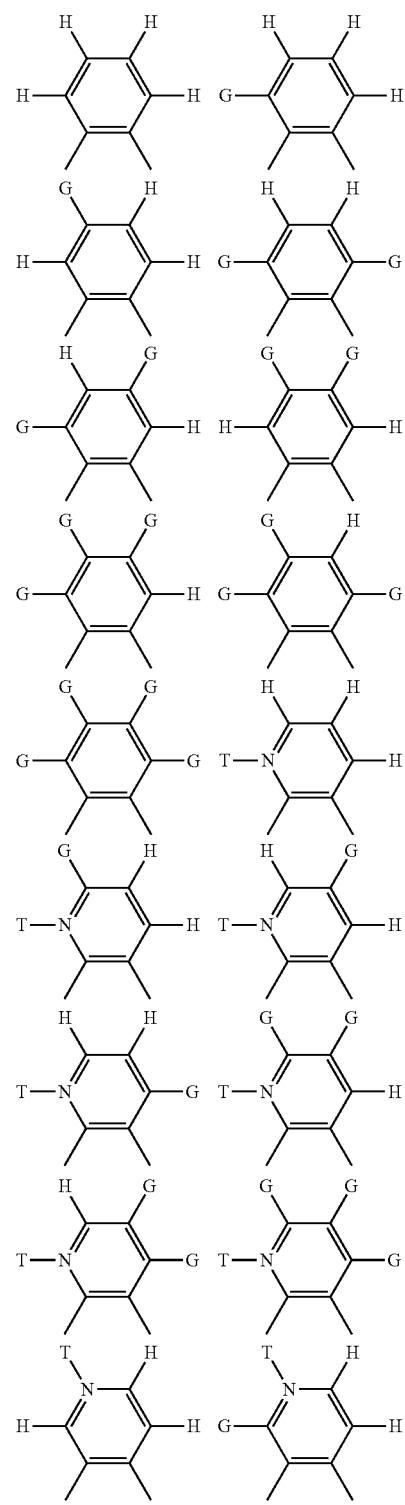

-continued

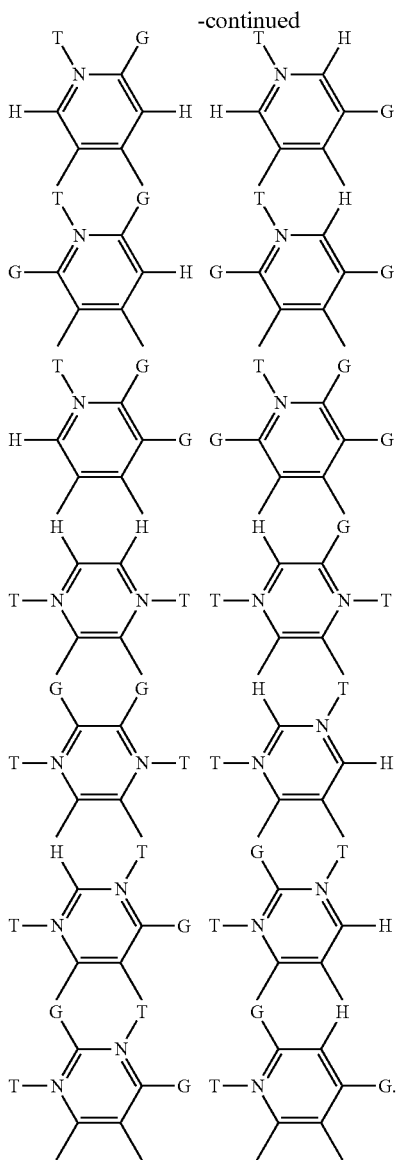

Each T in the foregoing benzene and substituted benzene structures listed for the $Y_2$ aryl group is the same or different and is one of an unoccupied position, or is occupied with one of a hydrogen, alkyl, or haloalkyl.

Each G of the aryl group listed for $Y_2$ is the same or different and comprises halogen, hydrogen, alkyl, cycloalkyl, alkenyl, cycloalkenyl, alkynyl, aryl, polycyclic aryl which may contain at least one ring atom that is not carbon, alkylaryl, phenoxy substituents, amino, substituted amino, or amino, substituted amino, amido (—NHCOR, —NRCOR, —NHSO$_2$R, —NRSO$_2$R, —NHPO$_2$R$^-$, —NRPO$_2^-$, —NHPO(OR)R, NRPO(OR)R), fully oxidized or partially oxidized or substituted or unsubstituted carboxylic acid derivatives including, but not limited to, carboxylate (—CO$_2^-$), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR) (NR$_2$)), phosphines (—PR$_3$), nitrile, nitro, hydroxyl, alkoxy, aryloxy, siloxy, and combinations thereof, or combine to form a cycloalkyl, cycloalkenyl or aromatic ring or rings including polycyclic aromatic systems, which may contain at least one ring atom that is not carbon, (ii) together with one or more G substituents on adjacent carbons, form a mono- or poly-substituted or unsubstituted saturated or unsaturated ring, (iii) joins with an R substituent of one or more G substituents forms a mono- or poly-substituted or unsubstituted saturated or unsaturated ring (iv) together with an R' substituent on an adjacent Z in an adjacent Y unit, form a mono- or poly-substituted or unsubstituted saturated or unsaturated ring, (v) joins together with a substituent on an adjacent E in an adjacent Y unit, form a mono- or poly-substituted or unsubstituted saturated or unsaturated ring.

The R as used in phosphate (—PO$_2$(OR)$^-$), phosphonate (—PO(OR)$_2$), phosphinate (—PO(OR)R), phosphine oxide (—P(O)R$_2$), sulfones (—SO$_2$R), sulfonamides (—SO$_2$(NH$_2$), —SO$_2$(NHR), —SO$_2$(NR$_2$)), phosphonamides (—PO$_2$(NR$_2$)$^-$, —PO(NR$_2$)$_2$, —PO(OR) (NR$_2$)) herein may be any of the other R substituents designated for $R_5$ through $R_{17}$ in any of the variations of the compounds herein, and preferably a substituted or unsubstituted alkyl group.

The compounds of the present invention form robust, long-lived oxidation catalysts and precatalysts that are far superior in technical performance to TAML activators such that large-scale objectives in oxidation technology, including the removal of micropollutants and pathogens from water, become significantly more achievable. For the sake of convenience, and without limiting the scope of the invention, "catalyst" will be used herein to include precatalyst, resting catalyst, and active catalyst complexes, where the latter is the species that carries out the oxidation. The compounds may also function as activators for initiation of the catalytic reaction. In many cases, while much is known about the general mechanism which one can assert based on scientific evidence, the precise details of the catalytic mechanism are not known and thus the precise role of the chelate system and compounds of the present invention in any given reaction may not be known.

As used herein, "robust oxidation catalyst" means that when the catalyst itself or a form of it that is confined to a solid surface is added to a solvent in the presence of an oxidant, such as a peroxide or any oxygen transfer agent, or an electrode with or without a mediator in its oxidized state that is generated or regenerated by the electrode, the time in which half of the metal complex decomposes or degrades (half-life) is at least 30 minutes or more. In practice, the half-life is usually much longer than this, unless a site of vulnerability has been deliberately incorporated to limit the catalyst lifetime.

The design of preferred embodiments of the new robust compounds differs from the prior art compounds by at least one, preferably two, three, or most preferably, four substitutions of the four amido-N constituent groups common to TAML activators with four amido-N ligands with a Nucleophile Resistant Functionality (herein abbreviated as "NuRF"). Substituting at least one amide of the prior compounds with a NuRF generates catalysts having a more favorable balance of Techperps including increased resistance to hydrolysis, perhydrolysis or other forms of nucleophilic attack at the site of substitution due to the resistance of these NuRFs to nucleophilic addition, and increased $k_{II}$ activity due to the increase in electron-withdrawing capacity of these NuRFs. Thus, substitution of an amido-N group with a sulfonamide or a phosphonamide or a related species with heavier elements from the oxygen (Group 16) and nitrogen (Group 15) families of the periodic table in the structure is the key to a new class of more reactive and ultimately much longer-lived oxidation catalysts.

Understanding (1) the ligand structural components being replaced, (2) the identity of the functional groups chosen to replace them, (3) the impacts on catalyst lifetime associated with such replacements, and (4) the anticipated increases in $k_{II}$ activity requires an examination of our previous and current knowledge of the processes that make up the productive catalytic cycle and those that compromise it, especially the novel findings of processes that result in inactivation of the active form of TAML catalysts including nucleophilic attack and formation of an carbanion at a position of the chelate ligand other than D which have lead to these new inventions.

Figure 3:
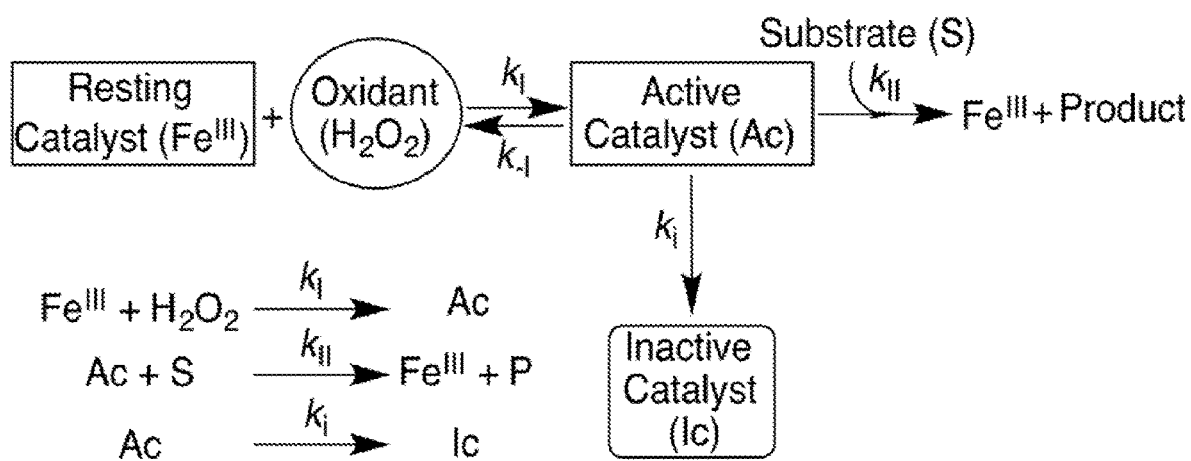
FIG. 3 illustrates the stoichiometric steps and labels of the associated rate constants that describe TAML catalysis under turnover conditions and the peroxide independent and peroxide dependent pathways that lead to the inactivation of active TAML catalysts.

Catalysis with the amido-N macrocyclic tetraamido activators typically follows the stoichiometric mechanism shown in FIG. 3A. The resting catalyst is activated by an oxidant, such as hydrogen peroxide, to generate an active catalyst in a process with rate constant $k_I$. The active catalyst then either oxidizes a substrate ($k_{II}$) or undergoes irreversible inactivation ($k_i$). The relationship between $k_i$ and $k_{II}$ of critical importance to the amido-N macrocyclic tetraamido activator technical performance.

Early studies of the lifetime of functioning TAML catalysts were conducted under basic conditions of pH 11 and above. These studies were qualitative in nature. As such, it is not possible to define the relationship between $k_i$ and $k_{II}$ numerically from them. However, the operation of a process that causes the inactivation of functioning TAML catalysts is evident. A self-inactivation pathway was identified by generating the active catalyst in acetonitrile at low temperatures and observing its decay product. These studies demonstrated that the ethyl groups in the $R_1$ and $R_2$ positions of prior art complexes undergo self oxidation by the oxo ligand of the active catalyst leading to degradation of the chelate ligand and loss of catalytic activity. Incorporation of oxidation resistant functionalities in the $R_1$ and $R_2$ positions of prior art complexes led to complexes which qualitatively appear to function for longer periods of time at high pH. From these studies it was concluded that the main catalyst inactivation pathway was oxidative and this formed the basis of the TAML design trajectory. This trajectory was geared at replacing oxidatively sensitive functionalities with those known to be resistant to oxidation. See the Collins' Group Patents. These complexes have proven to be capable of transforming large numbers of substrate molecules as the rate of catalyst inactivation is less than that of the productive catalysis. The resulting macrocyclic tetra-amido activators described in the Collins' Group Patents and sold commercially as TAML® activators are catalysts having oxidatively resistant ligand systems that are long lived.

Later advances in theory enabled the development of a method for parameterizing catalyst lifetime numerically, but it relies on mathematical assumptions that are only certain to be valid for describing catalytic processes at high pH (Chanda, A.; et al., *Chem. Eur. J.*, 2006, 12, 9336). Consequently, this method was not utilized to study catalysis at pH 7, conditions of critical importance for water treatment applications. Employment of this model at pH 11 demonstrated that a negative correlation exists between log $k_i$ and log $k_{II}$ for eight catalysts such that catalysts displaying high $k_{ii}$ values also have lower $k_i$ values here. At high pH, the properties of these catalysts vary such that catalysts obtained by appending electron-withdrawing substituents to the aromatic ring of Structure 1 appear to display greater $k_{II}$ values and lower $k_i$ values. These results support the earlier conclusion that the main inactivation pathway of TAML® catalysts at high pH is oxidative in nature since catalysts displaying greater $k_{II}$ values have less electron-density in the ligand structure which would also be expected to confer resistance to oxidation upon them resulting in slower oxidative inactivation and increased catalytic lifetime (lower $k_i$ values). These and several other observations of oxidative inactivation pathways were made at high pH where the concentrations of the nucleophilic species $OH^-$ and $HOO^-$ are high. As a result, it was assumed that at pH 7 catalyst inactivation would be oxidative as well since the concentrations of these species are lower at neutral pH.

More recent work resulted in the development of a protocol for evaluating $k_i$ under any one set of conditions, including at and near pH 7, (See Maria Emelianenko et al., "Estimation of rate constants in nonlinear reactions involving chemical inactivation of oxidation catalysts," *J. Math. Chem.*, 2014, 52, 1460-1476 DOI 10.1007/s10910-014-0322-4). This protocol was able to provide $k_i$, $k_I$, and $k_{II}$ for one TAML catalyst from a limited data set with reasonable accuracy. However, the approach was not able to generate $k_i$, $k_I$ and $k_{II}$ values of high enough accuracy to facilitate definitive comparisons of reactivity between several closely related catalysts. A more accurate approach was required. By coupling this new tool for calculating $k_i$ at neutral pH with more reliable methods of measuring $k_I$ and $k_{II}$ which required more data, a set of very accurate pH 7 $k_i$ and $k_{II}$ values for catalysis of the oxidation of a model substrate by most existing room temperature active TAML catalysts was generated. Surprisingly, at neutral pH the $k_i$ and $k_{II}$ values vary in a manner that is the exact opposite of the trend observed at pH 11. This correlation identifies what is referred to herein as "a stability wall". All modifications made to the ligand structure of the previous TAML catalyst observed to increase $k_{II}$ and decrease $k_i$ at pH 11 have been determined to increase both $k_{II}$ and $k_i$ at pH 7.

In total, the pH 7 data unexpectedly indicate that one or more common structural features that are neither the aromatic ring nor the geminal substituents of the malonamide tail are the location of the pH 7 lifetime-limiting, non-oxidative catalyst inactivation pathway or pathways. Since the iron center and the amido-N ligands are the only structural features common to all of the catalysts assayed, these stand out as possible sites of catalyst inactivation. The analytical form of the line of best fit to the pH 7 data is represented by Equation 1 below. The positive correlation between log $k_i$ and log $k_{II}$ indicates that the main inactivation process at neutral pH is not oxidative and is instead likely to be nucleophilic attack.

$$\log k_i = (0.9 \pm 0.1) \times \log k_{II} - (6.7 \pm 0.4) \tag{1}$$

Figure 2:
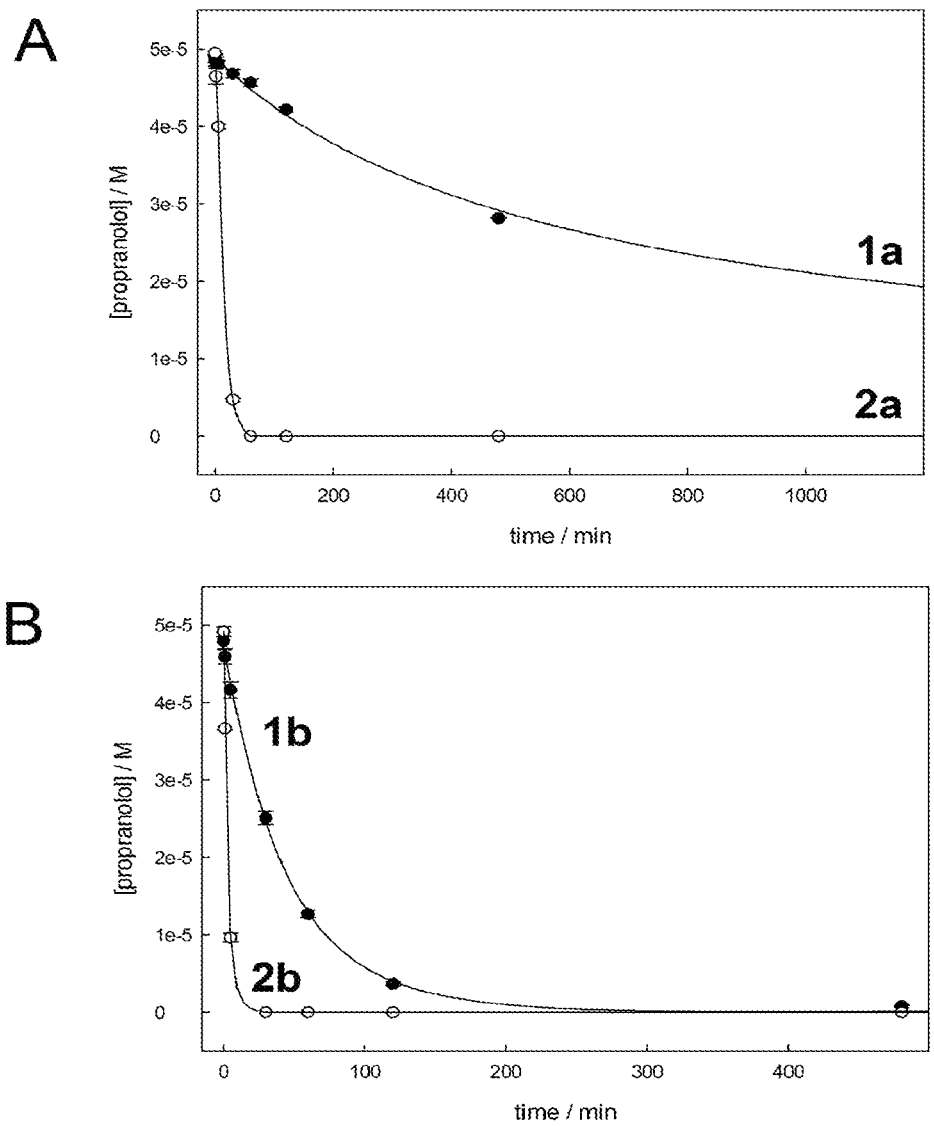
FIGS. 2A and B show the differential performance between the macrocyclic tetraamido catalysts of FIG. 1 (Structure 1, 1a: G=H, R=CH$_3$, 1b: G=NO$_2$, R=CH$_3$) and the improved macrocyclic sulfonamide catalysts of FIG. 1 (Structure 2, 2a: G=R=H, 2b: G=NO$_2$, R=H) in the degradation of propranolol at pH 7 (0.01 M Phosphate) at 25° C., wherein the initial [propranolol]=50 mM, [H$_2$O$_2$]=5 mM, and [catalyst 1 or 2]=1 μM. Substitution of the nucleophile resistant functionality E into the prototype catalyst 1 framework results in catalysts 2a and 2b. (A) compares the performances of 1a and 2a. Catalyst 2a is capable of completely degrading the target micropollutant propranolol in 30 minutes whereas catalyst 1a achieves only a 60% reduction in 1,200 minutes. (B) compares the performances of 1b and 2b, NO$_2$-substituted versions of 1a and 2a. Catalyst 1b is capable of completely degrading the target micropollutant propranolol in 500 minutes whereas catalyst 2b requires only 5 minutes. Substitution of two sites of catalysts 1a and 2a with nucleophile resistant functionalities to generate 1a and 2b results in approximately 100-fold greater performance.

This nucleophilic degradation pathway was entirely unexpected. The precise reason for the stark contrast between the mechanisms of inactivation observed at neutral pH and those observed at high pH is still unknown. Nonetheless, since the functionality most susceptible to nucleophilic attack is the carbonyl carbon the decision was made to reduce the susceptibility of the atom at this position to such an attack by substituting a NuRF sulfonamide or phosphonamide or related functionality for at least one amido carbonyl carbon containing E. Doing so has been found to greatly enhance catalyst performance. The superior performance of the new compounds has been clearly demonstrated through comparative tests conducted on embodiments of the prior TAML and new catalysts. For example, the performance of TAML activators (Structure 1) was compared to that of the new macrocyclic compounds (Structure 2) as shown in FIG. 1. Substitution of two nucleophile resistant functionalities into the prior catalyst framework results in an embodiment of the new catalyst, Structure 2. As shown in FIG. 2A, the new catalyst designated Structure 2a is capable of completely degrading the target micropollutant propranolol in 30 minutes whereas catalyst 1a achieves only a 60% reduction in 1,200 minutes. As shown in FIG. 2B, the new catalyst 2b, a $NO_2$-substituted version of 2a, is capable of completely degrading propranolol in 5 minutes whereas 1b, the $NO_2$-substituted version of 1a, requires 500 minutes. Substitution of two sites of Structure 1 catalysts with nucleophile resistant functionalities to generate catalysts of Structure 2 results in an approximate 100-fold increase in performance.

After employment in certain targeted applications, such as any water treatment process, a method of inactivating the catalyst is desirable as it would remove concerns of low-dose adverse affects corrupting the environment on release of a very powerful and persistent catalyst. In the process of investigating the reactivities of the catalysts depicted in Structure 2 (FIG. 1), we have discovered a novel and unanticipated catalyst inactivation pathway, which has never been observed for the amido-N macrocyclic activators. This pathway occurs when $R_1$ and/or $R_2$ are H or D and appears to be associated with acid dissociation of $H^+$ or $D^+$ to give a carbanion rendering a much less stable catalyst system. Moreover, this "kill switch" is most turned on in the activated form of the catalyst and becomes more evident with increasing pH. Thus, the catalysts of Structure 2 when $R_1$ and/or $R_2$ are H or D decay more rapidly when in the activated state and at elevated pH than expected by the comparative behavior of all other catalysts. Because the catalysts of Structure 2 are so reactive in water, this "kill switch" is an overall positive factor in the embodied compositions, bringing added safety for release of such catalysts to the environment. At elevated pHs, the inactivation of Structure 2 catalysts is very rapid, prescribing a method for catalyst disposal when necessary.

Collins' Catalysts Syntheses

Methods of synthesizing tetraamido complexes include the wide based synthetic route to macrocyclic tetraamido ligands described in Uffelman, E. S., Ph.D. Thesis, California Institute of Technology, (1992), and any of the synthetic routes described in the Collins' Group Patents. The compounds of the present invention can be synthesized by a new synthetic route that permits the generation of variants which cannot be synthesized via the prior methods. In varying the macrocycle, however, it is desirable to preserve the general framework of the compound. The macrocycle will be made up of 5- and 6-membered chelate rings, in a 5,5,5,5 pattern, a 5,5,5,6 pattern, a 5,6,5,6, pattern, a 5,6,6,6 pattern, or a 6,6,6,6 ring pattern discussed in more detail below.

The new synthetic method proceeds generally as shown in sequences 1, 2, and 3 below. Specific examples of the application of the new method to the synthesis of some macrocycles containing nucleophile resistant (NuRF) functionalities are shown in sequence 4.

For convenience of classification herein, the starting materials that are composed of diamine functionalities are sometimes referred to as "Bridges" (B), the starting materials composed of diacid functionalities are sometimes referred to as "Linkers" (L), and the starting materials composed of amine/acid functionalities are sometimes referred to as "Arms" (A).

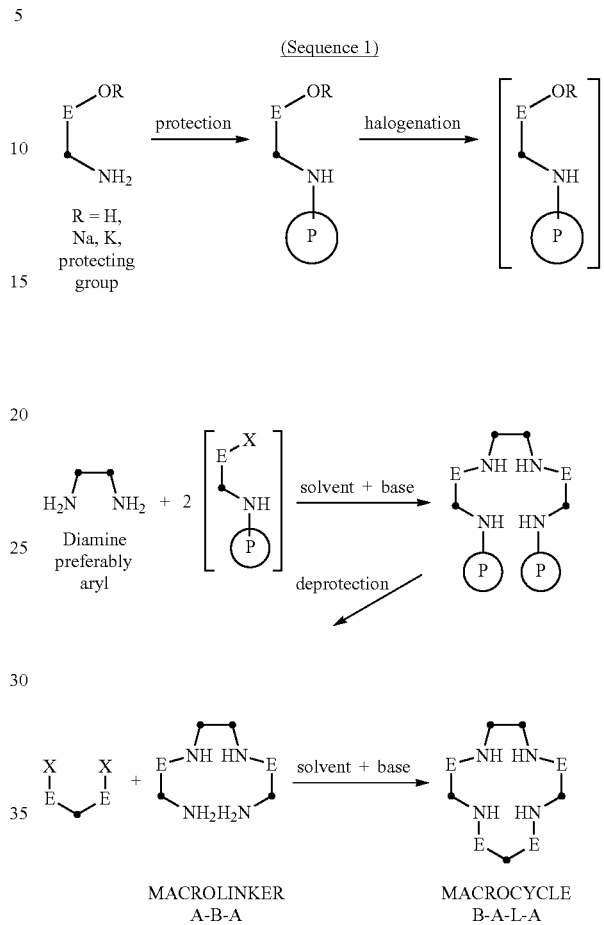

Sequence 1 is a generalized synthesis of NuRF functionality E containing tetradentate macrocycles having a (B-A-L-A-) configuration, from α-amino acids via the new synthetic method. The term "α-amino acids" as used herein refers to α-amino carboxylic, sulfonic, sulfinic, phosphonic, or phosphinic acids. For some α-amino acids, use of protecting group R may be desirable. A diamide diamine-containing intermediate, sometimes referred to herein by the short hand designation, "macro linker intermediate" or simply the "intermediate" (A-B-A) is prepared via a selective double coupling reaction wherein an activated amino acid, the arms (A), and a diamine, the bridge (B), are placed in solvent which may be heated with base to form the macro linker intermediate. The macro linker intermediate is then coupled to an activated diacid linker, L, in another selective double coupling reaction that employs a solvent and a base, and which may be heated. The term "diacids" as used herein refers to dicarboxylic, disulfonic, disulfinic, diphosphonic, or diphosphinic acids or combinations thereof. The synthetic methodology is highly streamlined and tolerates a wide range of functional groups. A wide range of amide, sulfonamide, sulfinamide, phosphonamide, and phosphinamide containing tetradentate macrocycles bearing substituents having widely varied electronic and/or steric properties can be prepared in this manner.

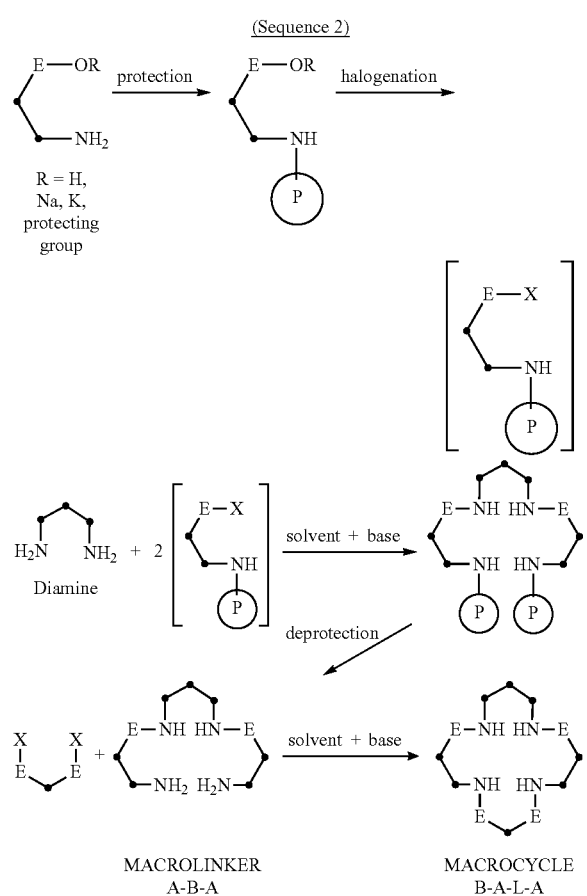

(Sequence 2)

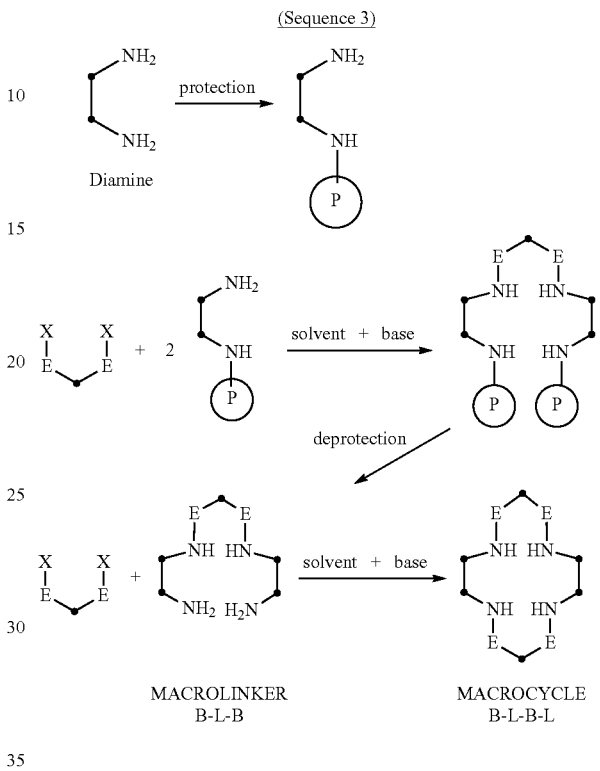

(Sequence 3)

Sequence 2 is a generalized synthesis of a NuRF functionality containing tetradentate macrocycle having a (B-A-L-A-) configuration, from β-amino acids via a modified version of the basic, or primary, synthetic method. The term "β-amino acids" as used herein refers to β-amino carboxylic acids, β-amino sulfonic or sulfonic acids, or (β-amino phosphonic or phosphinic acids. The basic approach employed with α-amino acid starting materials is applied to β-amino acid starting materials. For some β-amino acids, use of protecting group R may be desirable. A macro linker intermediate (A-B-A) is prepared via a selective double coupling reaction wherein an activated β-amino acid arm (A), and a diamine bridge (B), are heated in solvent with base to form the intermediate, which, after deprotection, can then be coupled to the activated diacid linker (L), in another selective double coupling reaction to yield a wide variety of substituted NuRF containing macrocyclic tetradentates with an expanded ring size compared to those that have been prepared from α-amino acids. Again, term diacids as used herein refers to dicarboxylic, disulfonic, disulfinic, diphosphonic, or diphosphinic acids or combinations thereof.

Sequence 3 is a generalized synthesis of a NuRF functionality containing tetradentate macrocycle having a (B-L-B-L-) configuration via a modified version of the basic, or primary, synthetic method. The basic approach employed with arm (A) starting materials is applied to bridge (B) starting materials. For some bridges, use of protecting group R may be desirable. A macro linker intermediate (B-L-B) is prepared via a selective double coupling reaction wherein bridge (B) and activated diacid linker (L) are heated in solvent with base to form the intermediate, which, after deprotection, can then be coupled to a second activated diacid linker in another selective double coupling reaction to yield a wide variety of substituted NuRF containing macrocyclic tetradentates with a different ring configuration compared to those that have been prepared from amino acids. Again, term diacids as used herein refers to dicarboxylic, disulfonic, disulfinic, diphosphonic, or diphosphinic acids or combinations thereof.

(Sequence 4)

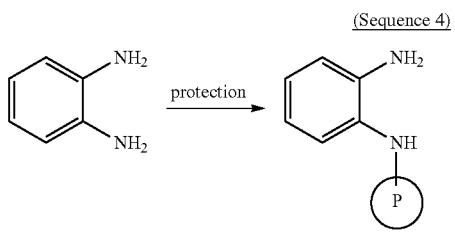

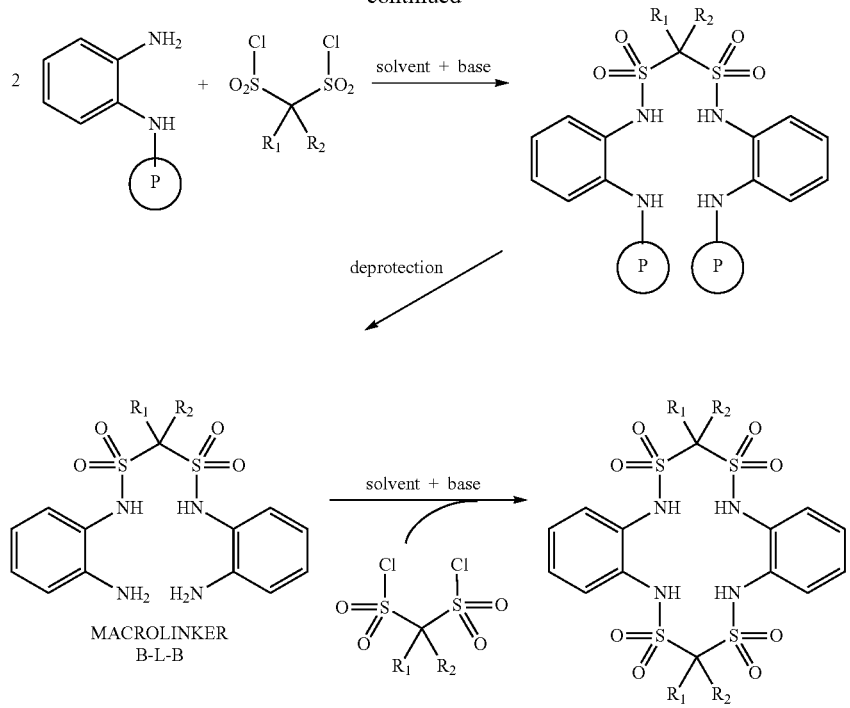

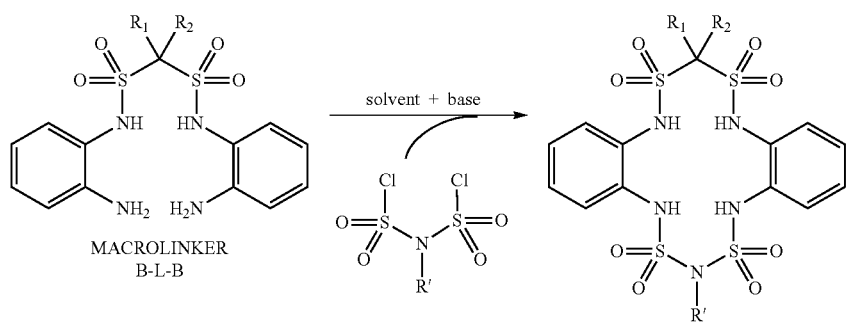

Sequence 4 is a specific example of the preparation of a macrocyclic tetrasulfonamide having a (B-L-B-L-) configuration from disulfonic acid dichloride starting materials. The amino terminus of o-phenylenediamine is first protected. The protected diamine is mixed with disulfonic acid dichloride linker, preferably a biuret or malonyl analog with R', $R_1$, and $R_2$ as defined above, in solvent with a base, preferably triethylamine or pyridine. After the selective double coupling reaction is complete, the macro linker intermediate (B-L-B) is deprotected. A second disulfonic acid chloride linker, preferably a biuret or malonyl analog with R', $R_1$, and $R_2$ as defined above, is added to a solution of the macro linker intermediate in the presence of a base, preferably triethylamine or pyridine. The ring closure, a double coupling reaction, is allowed to proceed for 24-72 hours and followed by isolation of the desired sulfonamide containing macrocycle.

In an alternative embodiment, the method of the invention uses a synthesis pathway similar to the method described in U.S. Pat. No. 6,051,704 via an Arm-Linker-Arm intermediate.

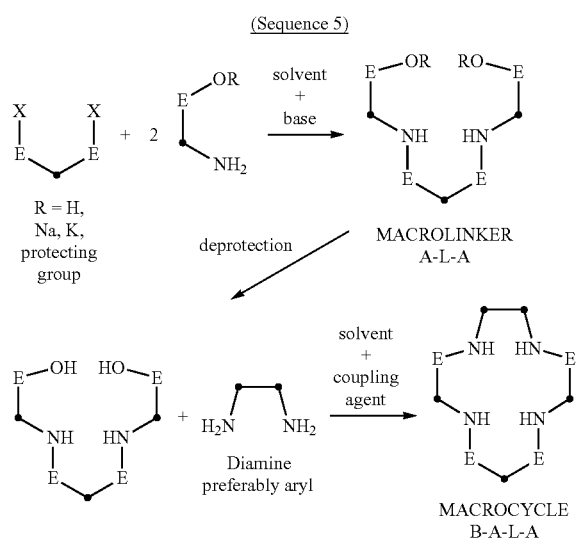

-continued

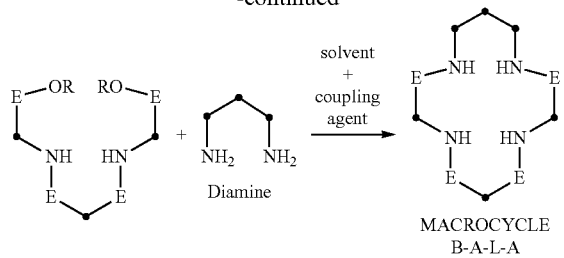

MACROCYCLE
B-A-L-A

Sequence 5 is a generalized synthesis of NuRF containing tetradentate macrocycles having a (B-A-L-A-) configuration, from α-amino acids via a route similar to the prior synthetic method. For some amino acids, use of a protecting group R may be desirable. An Arm-Linker-Arm (A-L-A) macro linker intermediate is preformed via a selective double coupling reaction wherein a protected amino carboxylic ester arm (A), and an activated acid linker (L), in solvent are heated to form the A-L-A intermediate, which, after deprotection, can then be coupled to the diamine bridge (B), in another selective double coupling reaction to yield a wide variety of substituted NuRF functionality E containing tetradentate macrocycles.

All embodiments of the method of the invention rely heavily on the amine and acid based starting materials hereinafter listed in Table 1. Table 1 lists several forms of the starting materials in what are designated as the parent, protected/activated and hidden forms of the amine and acid functionalities in a general sense. Table 2 utilizes these categories in conjunction with chelation ring size constraints (5- and 6-membered chelate rings are preferred) in order to identify useful starting materials for the synthesis of chelating NuRF containing tetradentate macrocycle compounds having the desired five- or six-membered ring.

As used herein "parent groups" (shown in italics in Table 1) define a preferred synthetic functionality. "Protected/activated groups" refers to those groups that contain an easily recognizable portion of the parent group. "Hidden groups" as used herein refers to those groups that need not contain an easily recognizable portion of the parent group but which are capable of ready conversion to the parent group or to a protected/activated form of the parent group. More detailed examples may readily be found in Greene and Greene, "Protective Groups in Organic Synthesis", John Wiley and Sons, New York (1981). An extensive list of protecting/activating groups particularly suitable for peptide synthesis may be found in G. A. Fletcher and J. H. Jones, "A List of Amino-Acid Derivatives Which are Useful in Peptide Synthesis", Int. J. Peptide Protein Res. 4, (1972), p. 347-371.

TABLE 1

| Protected/<br>Activated<br>Amines | Hidden<br>Amines | Protected/<br>Activated<br>Carboxylic Acids | Hidden<br>Carboxylic Acids |
|---|---|---|---|
| N-alkyl amines | azides | activated esters | nitriles |
| amides | azo compounds | acyl halides | oxazolines |
| amino acetals | imides | amides | hydroxyl |
| N-benzyls | isocyanates | anhydrides | terminal alkene |
| carbamates | isothiocyanates | hydrazides | |
| enamines | nitriliumions | O-acyl oximes | |
| hydrazines | nitro compounds | oxazolidines | |
| imines | phosphazos | oxazalones | |
| N-oxides | | phosphite esters | |
| N-phosphinyls | | silyl esters | |
| N-phosphoryls | | stannyl esters | |
| N-Metal derivatives | | substituted benzyl esters | |
| silyl amines (N—Si) | | substituted ethyl esters | |
| N-Sulfenyls | | substituted methyl esters | |
| sulfonamides | | sulfonyl esters | |
| N-Sulfonyls | | sulfenyl esters | |
| urea derivatives | | | |

| Protected/<br>Activated<br>S-containing Acids | Hidden | Protected/<br>Activated<br>P-containing Acids | Hidden |
|---|---|---|---|
| Thiols | | phosphines | |
| Sulfides | | alkyl phosphines | |
| Disulfides | | phosphoniums | |
| Sulfoxides | | phosphine oxides | |
| sulfenic acids | | phosphenic acids | |
| sulfones | | phosphonic acids | |
| sulfonic acids | | phosphite esters | |
| sulfonic acids | | phosphate esters | |
| sulfite esters | | phosphonamides | |
| sulfate esters | | phosphinamides | |
| sulfonamides | | phosphoramides | |
| sulfinamides | | phosphoramidates | |
| Thiones | | phosphoramidites | |

Structure 3 is used herein to define the shorthand notation shown in Table 2 and Table 3 (See FIGS. 4A-V) that specifies the chelate ring sizes (including the metal ion) that are formed when a given macrocyclic ligand is coordinated to a transition metal center.

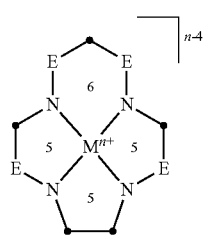

Structure 3

In the Tables, amine is designated by "a", and NuRF or amido functionality by "e". Dashes (—) indicate amide bonds. Every dash must connect a trailing "a" to a leading "e" or vice versa, the final dash wraps around to the beginning. Structure 3 illustrates a (5,5,6,5) macrocyclic ligand shown in metal coordinated form with chelate ring sizes (including the metal ion) indicated. Using a counter-clockwise rotation starting from the bottom, the specific macrocycle employed in Structure 3 is 5aa-5ea-6ee-5ae- (or any cyclic permutation thereof).

The parent (=) forms of the functional groups for each starting material are shown pictorially in Table 2 below, while possible combinations of protected/activated (p/a) or hidden (h) forms for each starting material are shown in tabular form. Variable positions are marked with a bullet (•). The underlined side captions are in a shorthand notation that refers to chelation ring sizes formed when the particular starting material is incorporated into a macrocycle and coordinated to a metal center. (See Structure 3)

TABLE 2

| 5ae | 1-E | 2-N | 1-E | 2-N | 1-E | 2-N |
|---|---|---|---|---|---|---|
| | = | = | p/a | = | h | = |
| | = | p/a | p/a | p/a | h | p/a |
| | = | h | p/a | h | h | h |

| 5aa | 1-N | 2-N | 1-N | 2-N | 1-N | 2-N |
|---|---|---|---|---|---|---|
| | = | = | p/a | = | h | = |
| | = | p/a | p/a | p/a | h | p/a |
| | = | h | p/a | h | h | h |

| 6ee | 1-E | 3-E | 1-E | 3-E | 1-F | 3-E |
|---|---|---|---|---|---|---|
| | = | = | p/a | = | h | = |
| | = | p/a | p/a | p/a | h | p/a |
| | = | h | p/a | h | h | h |

| 6ae | 1-E | 3-N | 1-E | 3-N | 1-E | 3-N |
|---|---|---|---|---|---|---|
| | = | = | p/a | = | h | = |
| | = | p/a | p/a | p/a | h | p/a |
| | = | h | p/a | h | h | h |

TABLE 2-continued

| 6aa | 1-N | 2-N | 1-N | 2-N | 1-N | 2-N |
|---|---|---|---|---|---|---|
| | = | = | p/a | = | h | = |
| | = | p/a | p/a | p/a | h | p/a |
| | = | h | p/a | h | h | h |

Figure 4A:
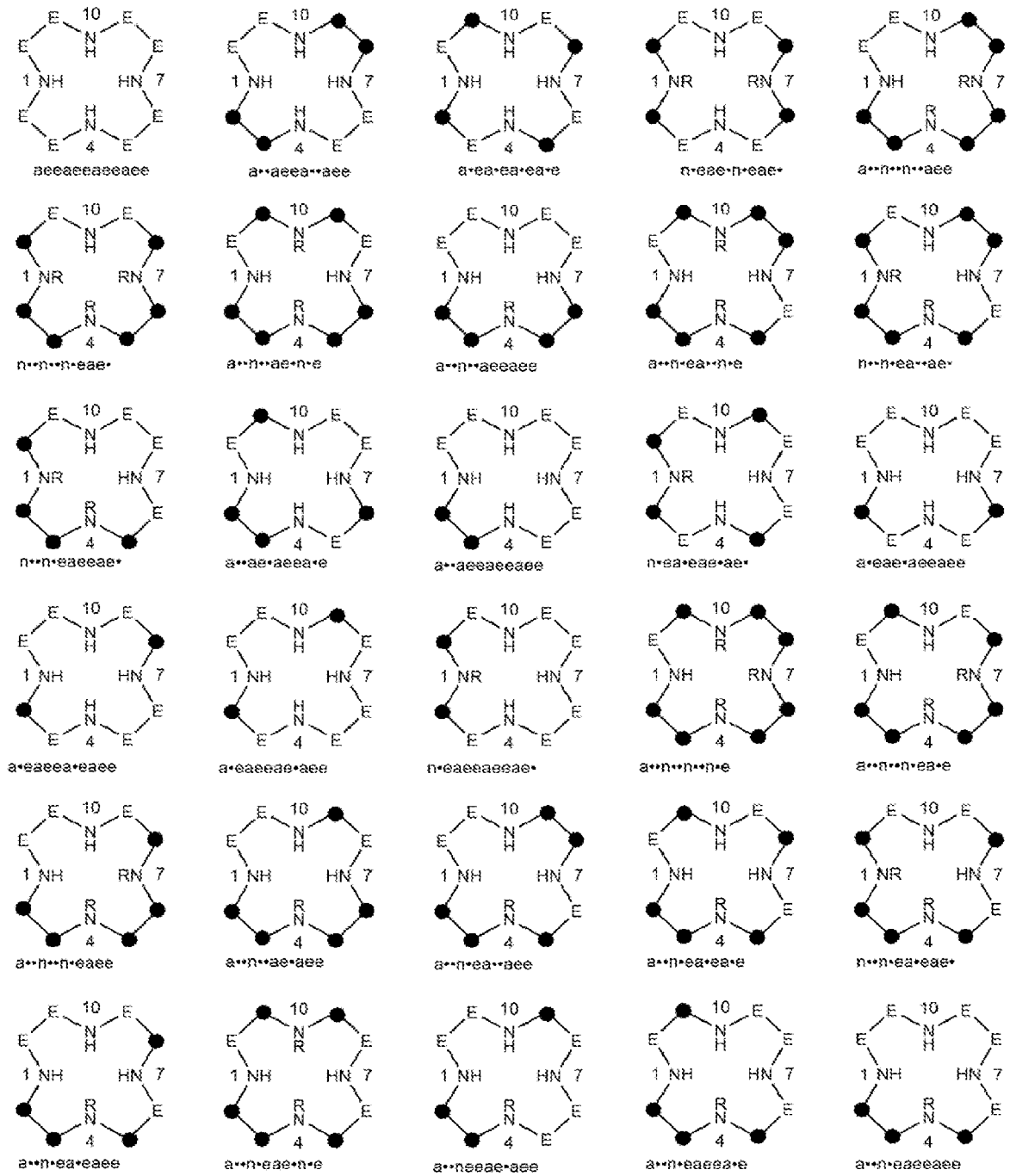
FIGS. 4A-V represent Table 3 showing the possible variations in macrocyclic structure for Compound 1 with, for example, the donor atom D as N in the ligand framework.
Figure 4B:
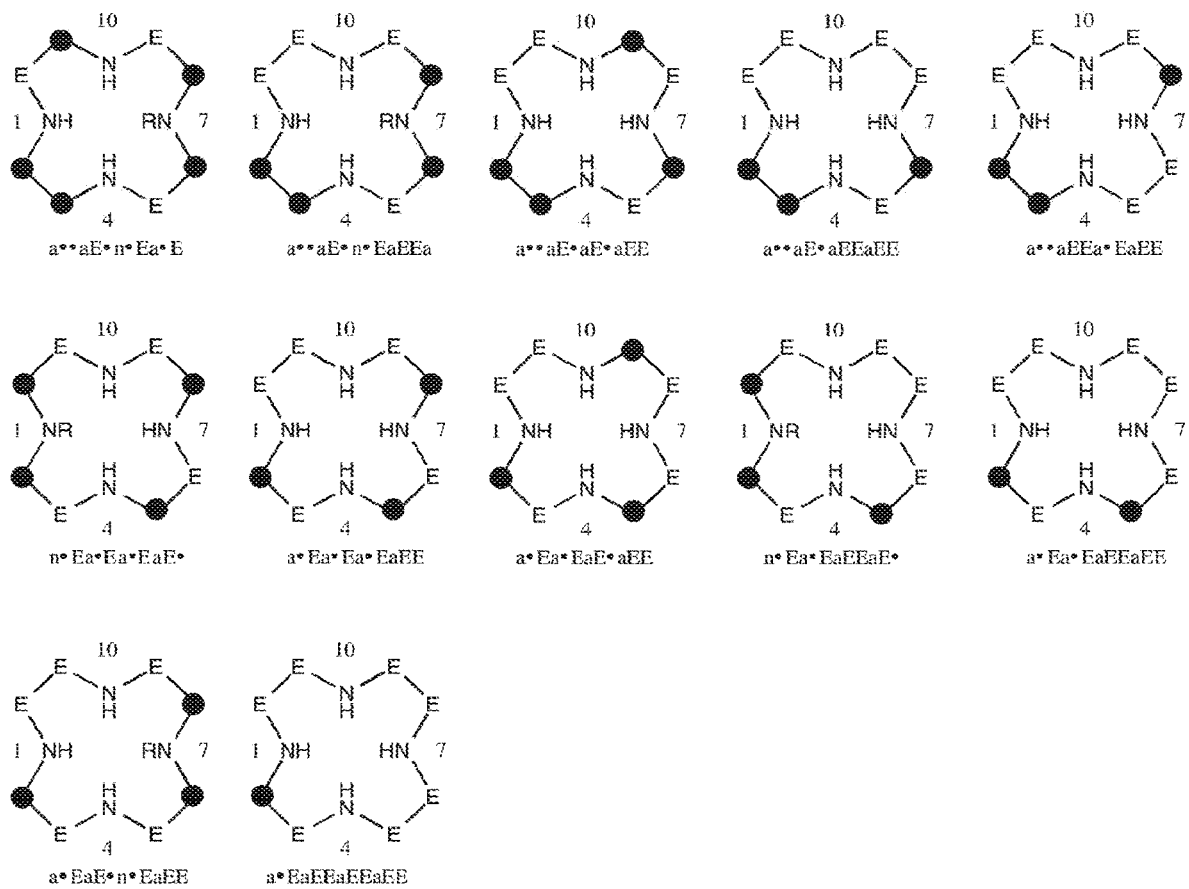
Figure 4C:
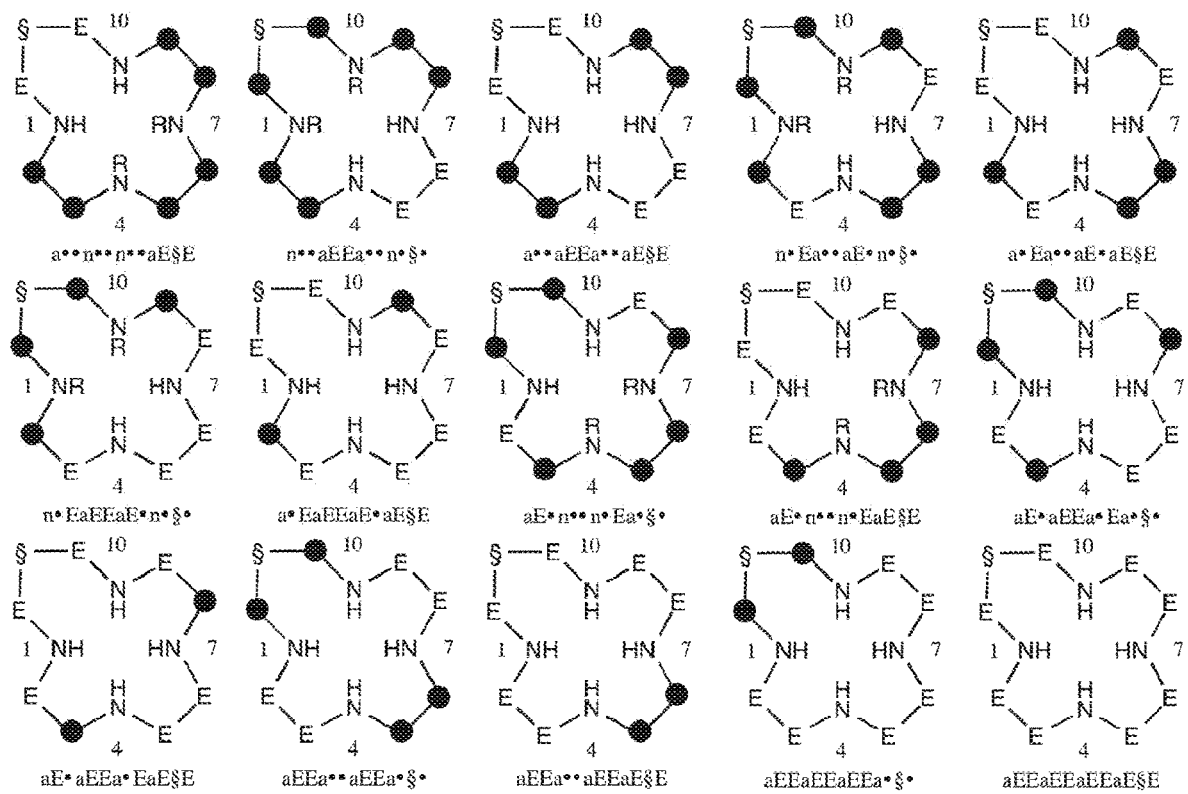
Figure 4D:
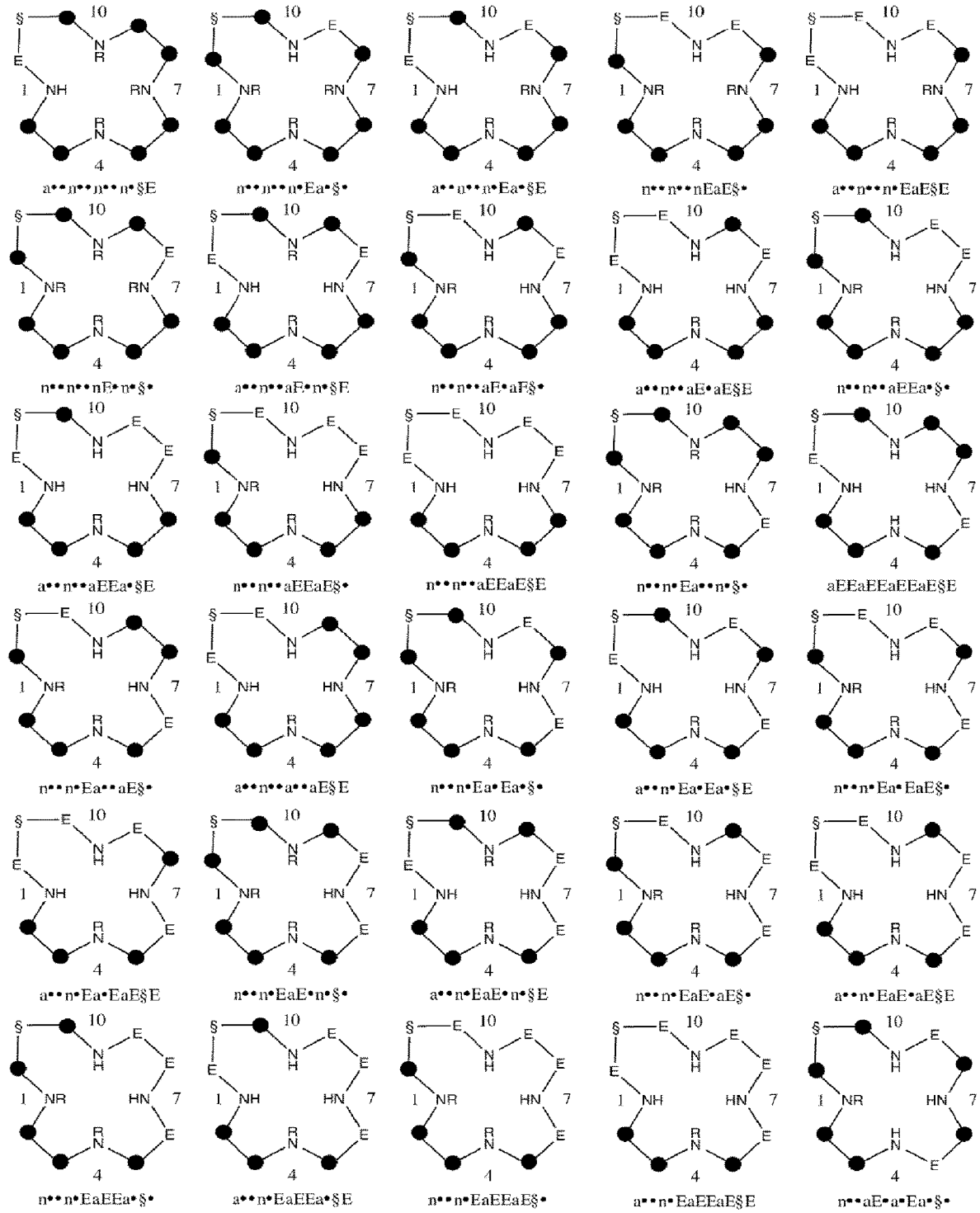
Figure 4E:
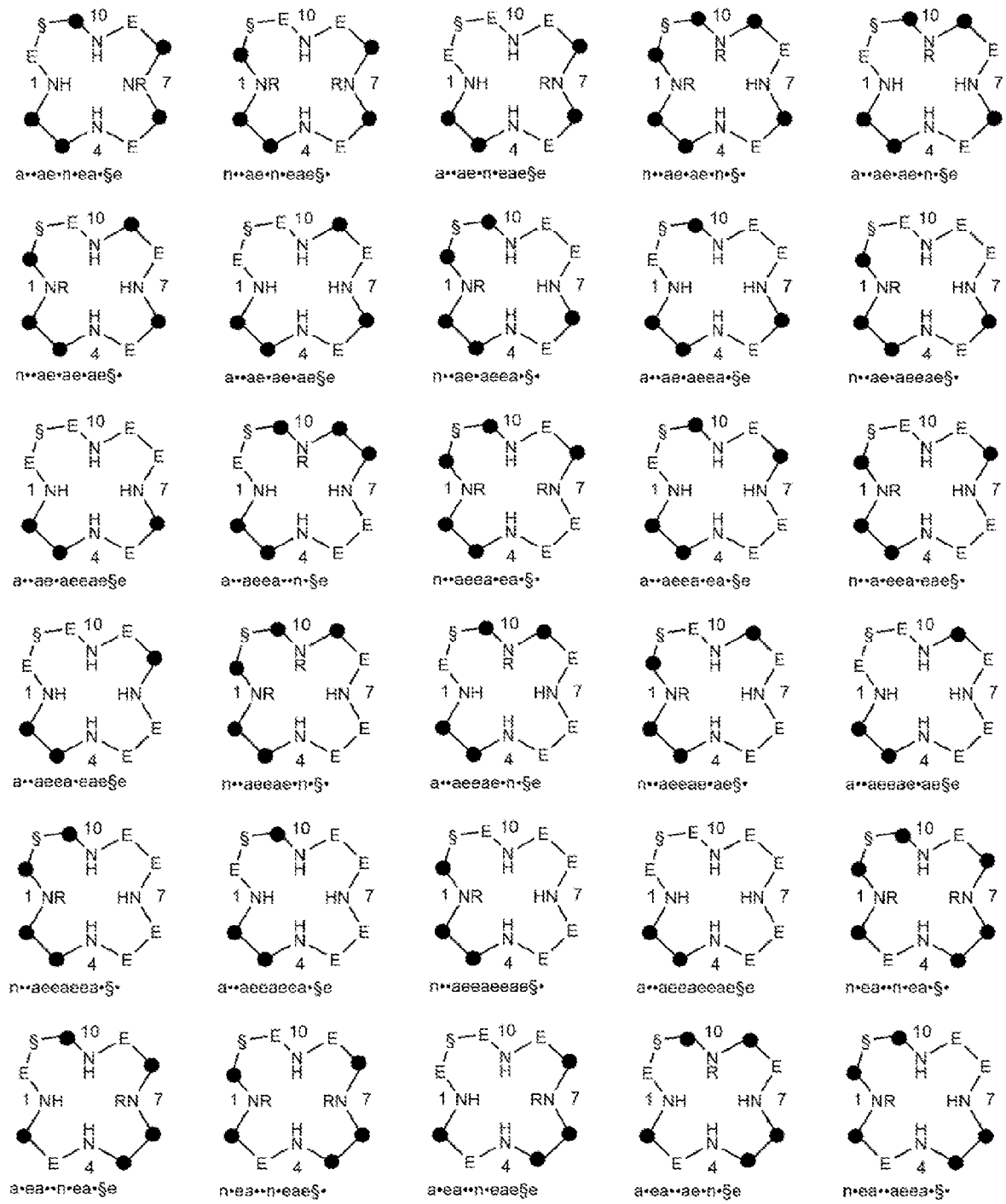
Figure 4F:
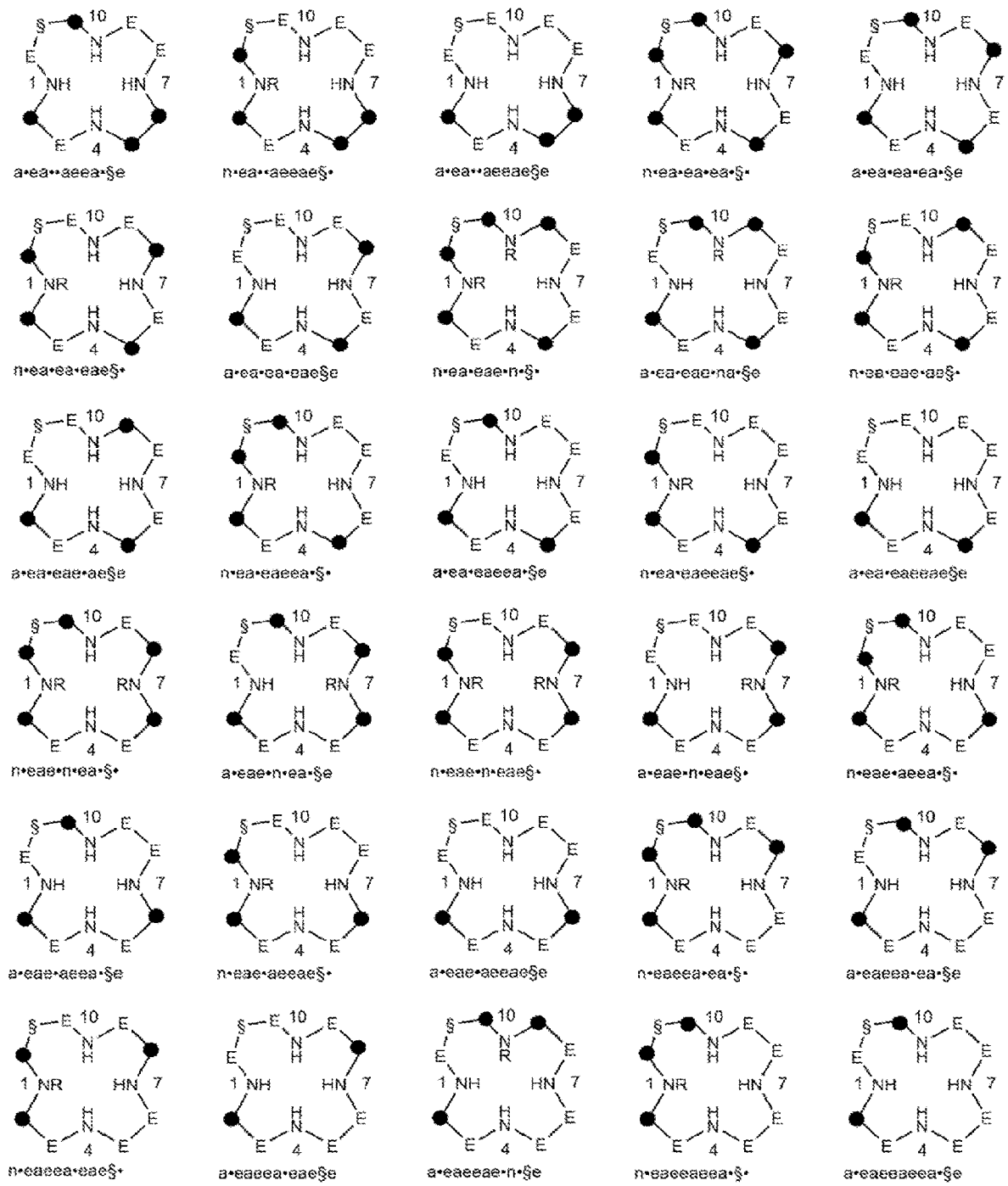
Figure 4G:
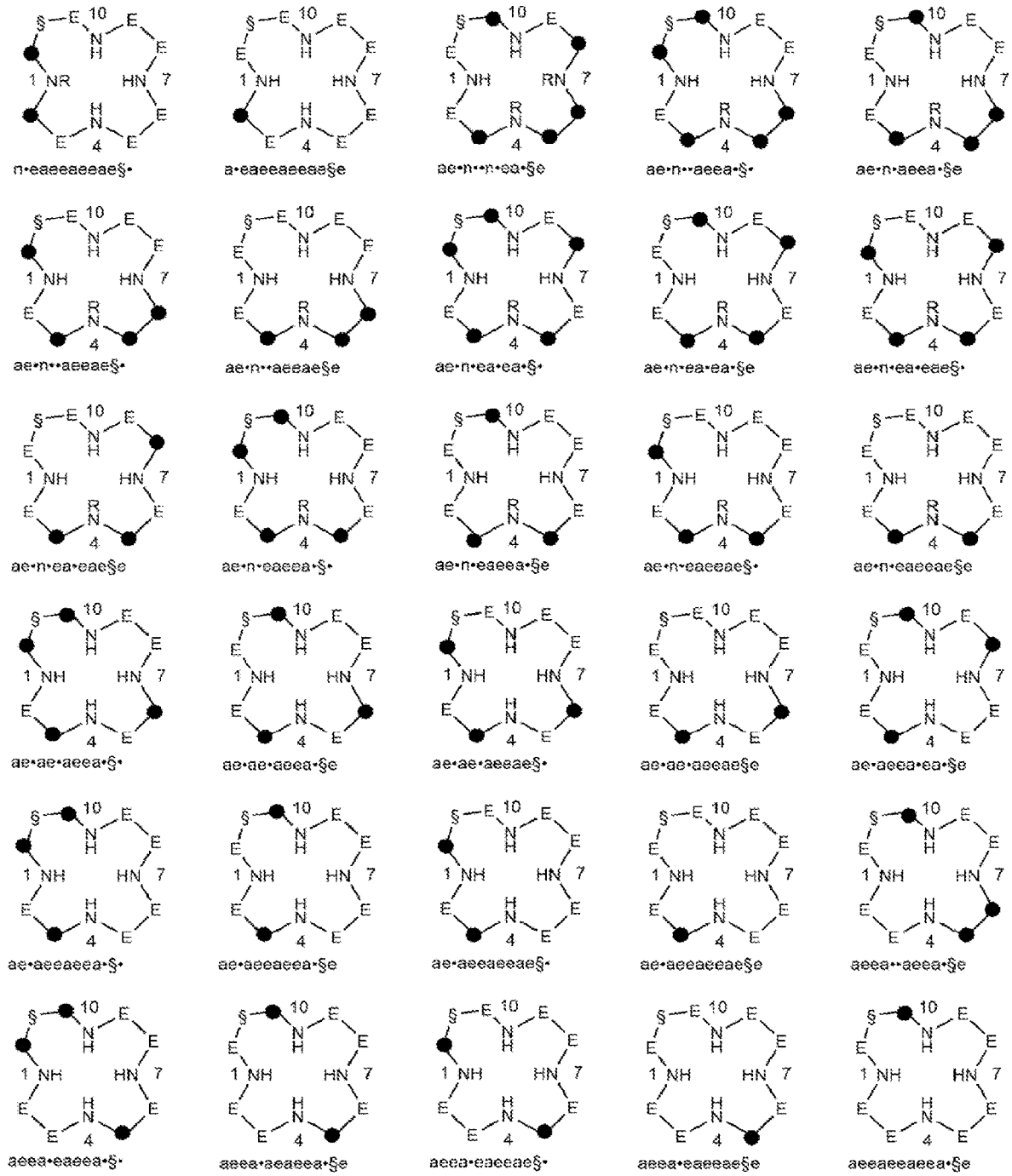
Figure 4:
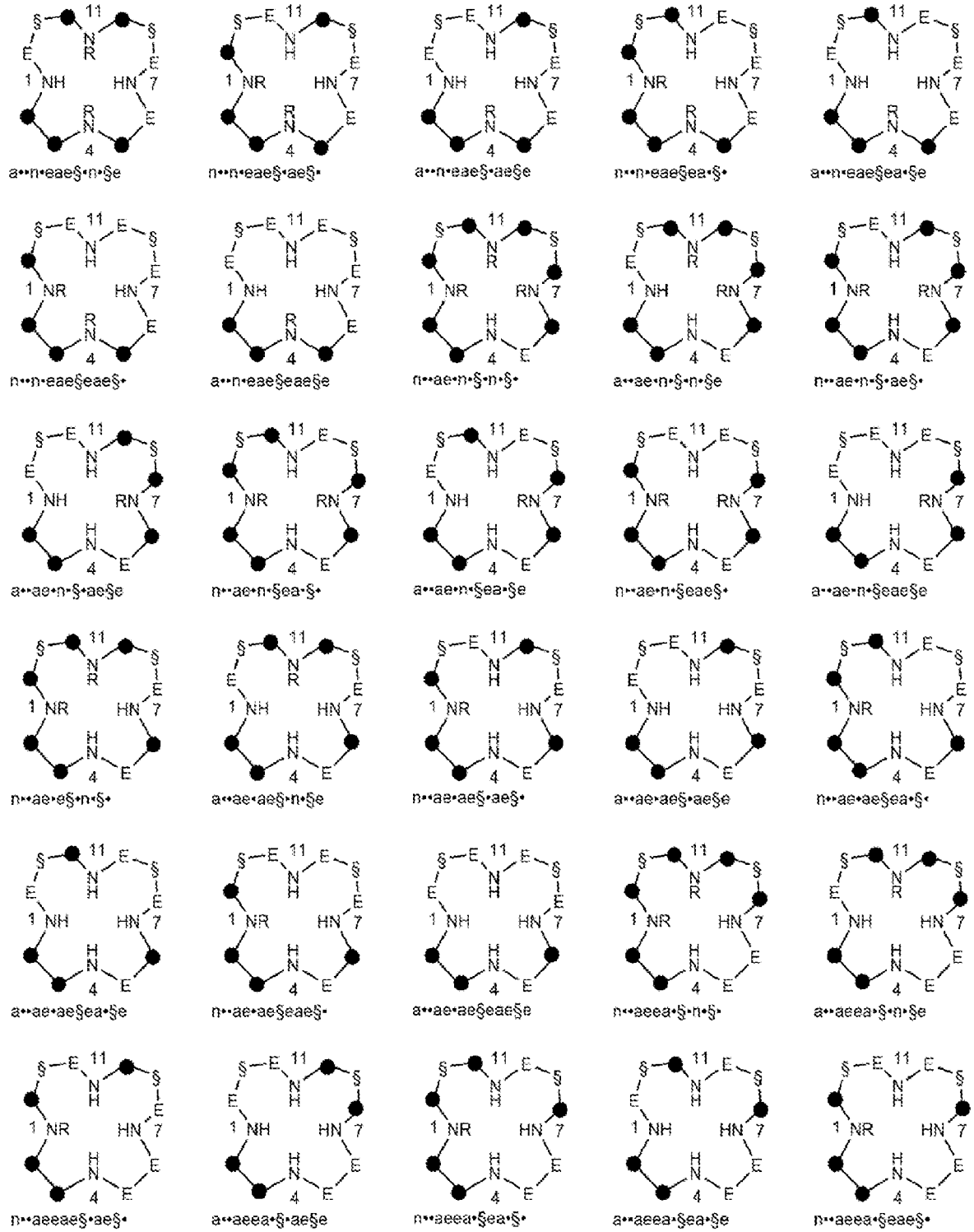
Figure 4I:
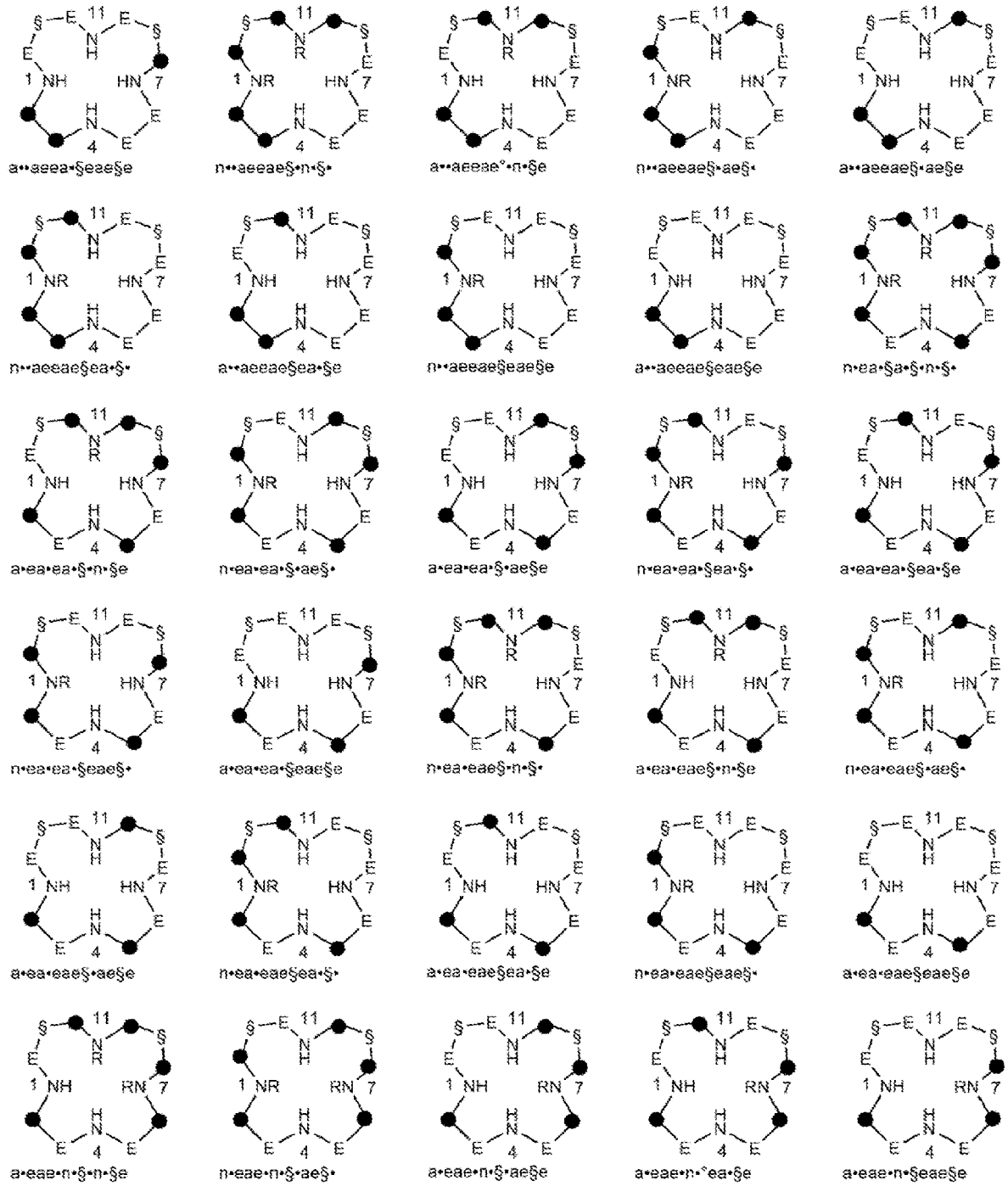
Figure 4J:
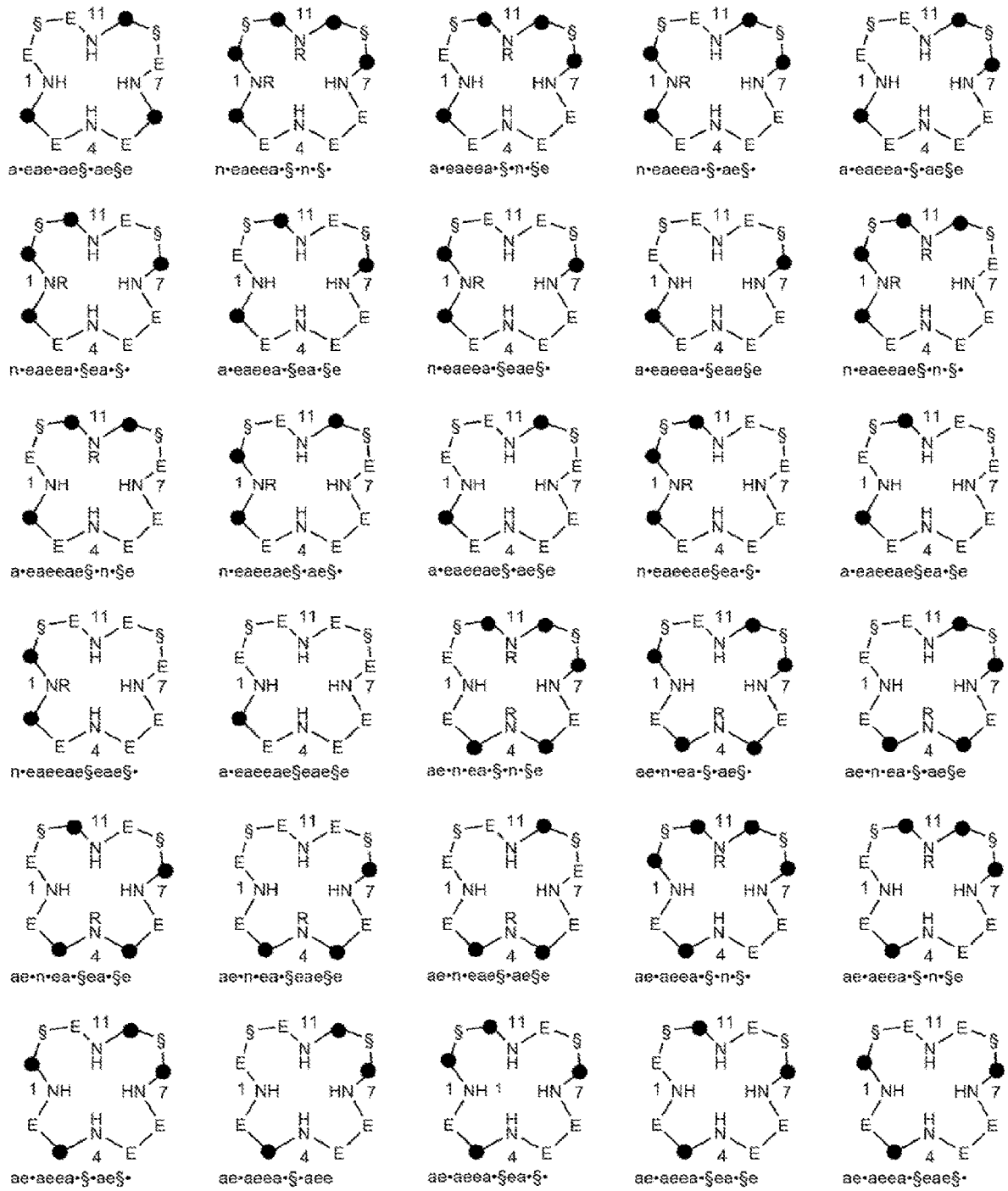
Figure 4K:
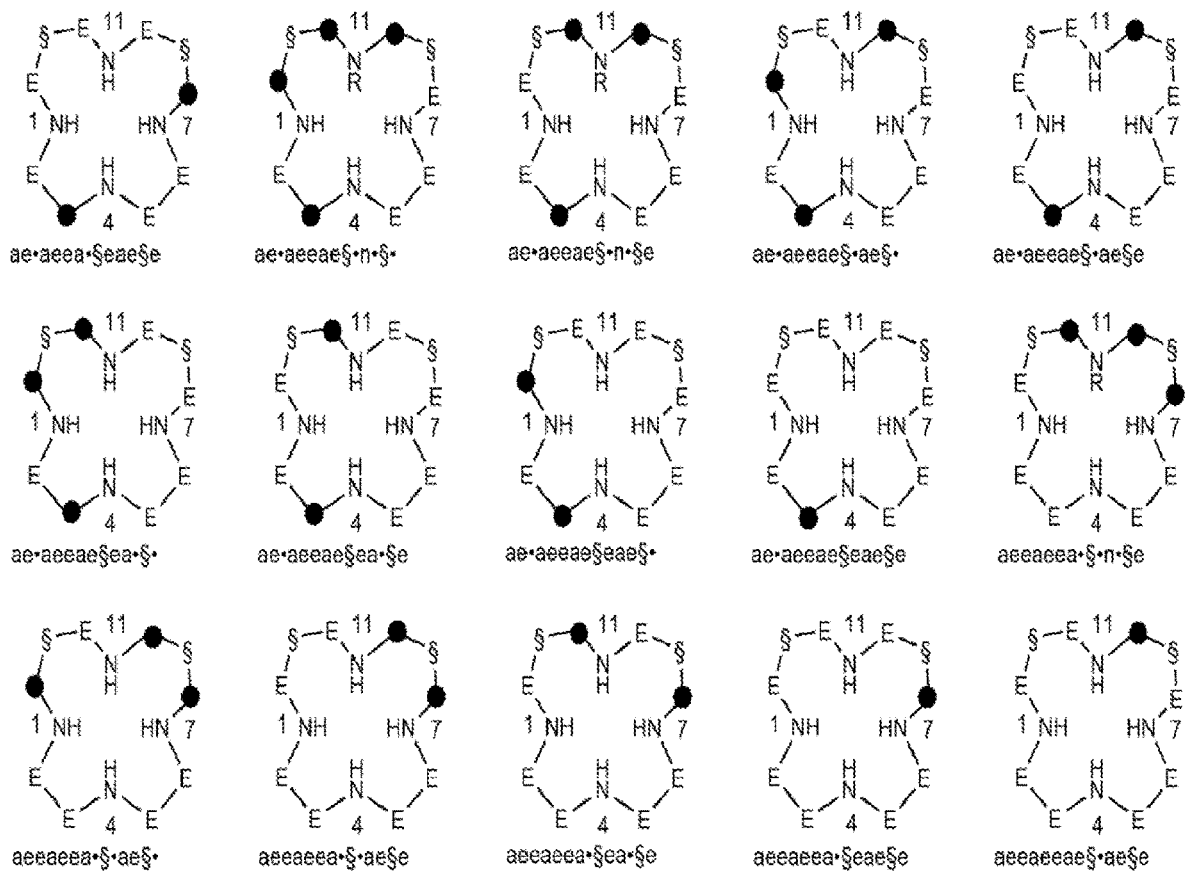
Figure 4L:
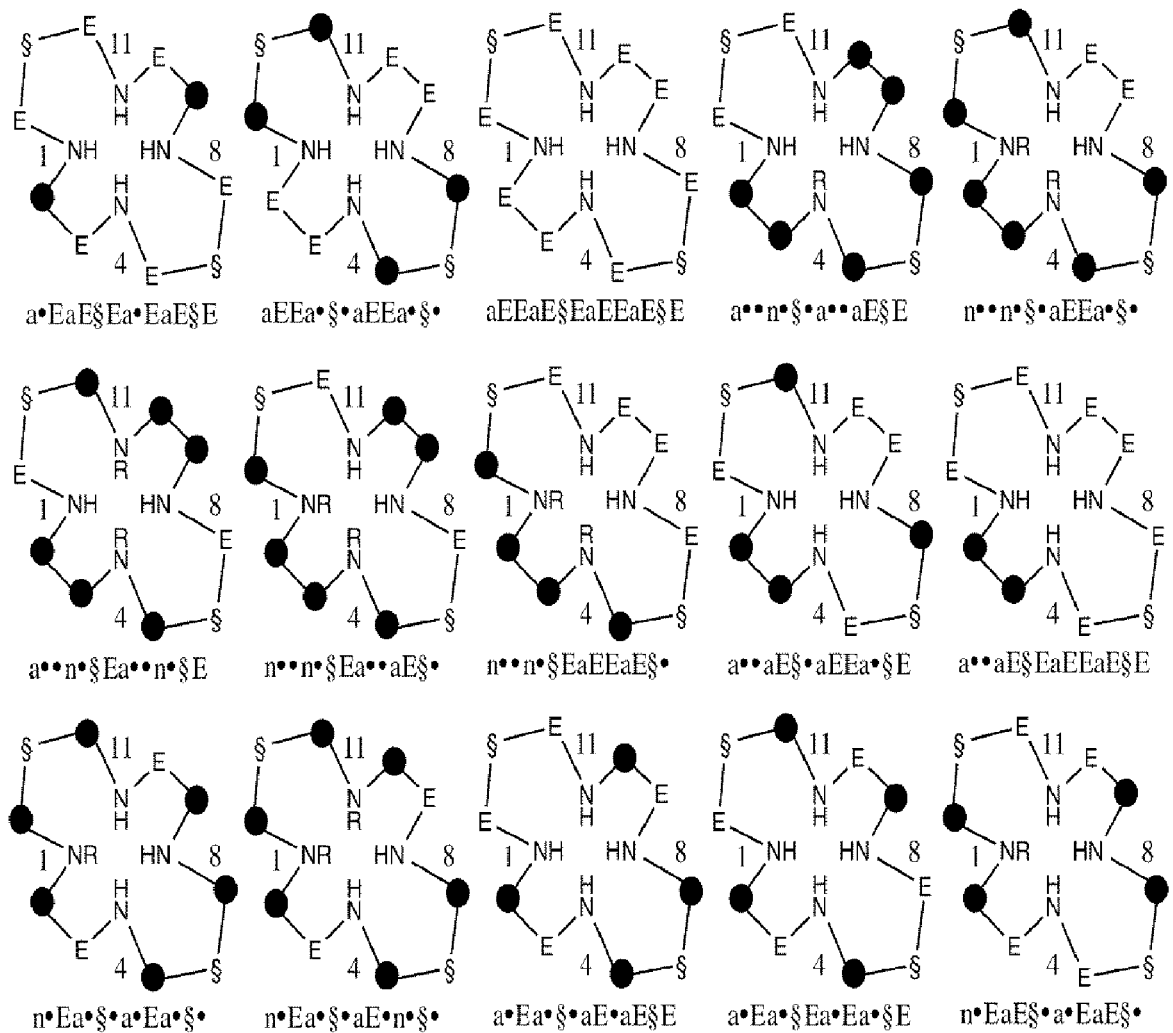
Figure 4M:
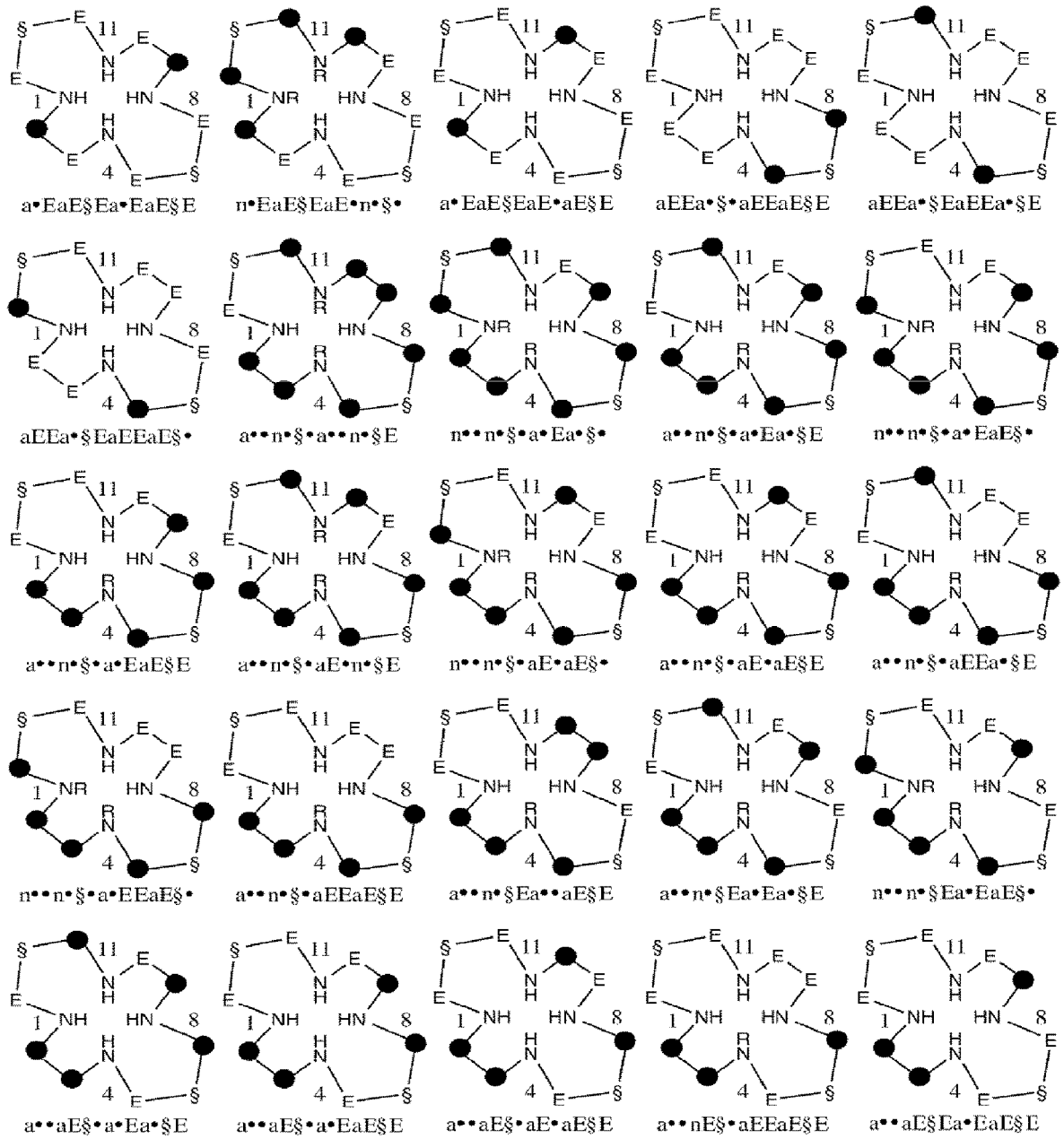
Figure 4N:
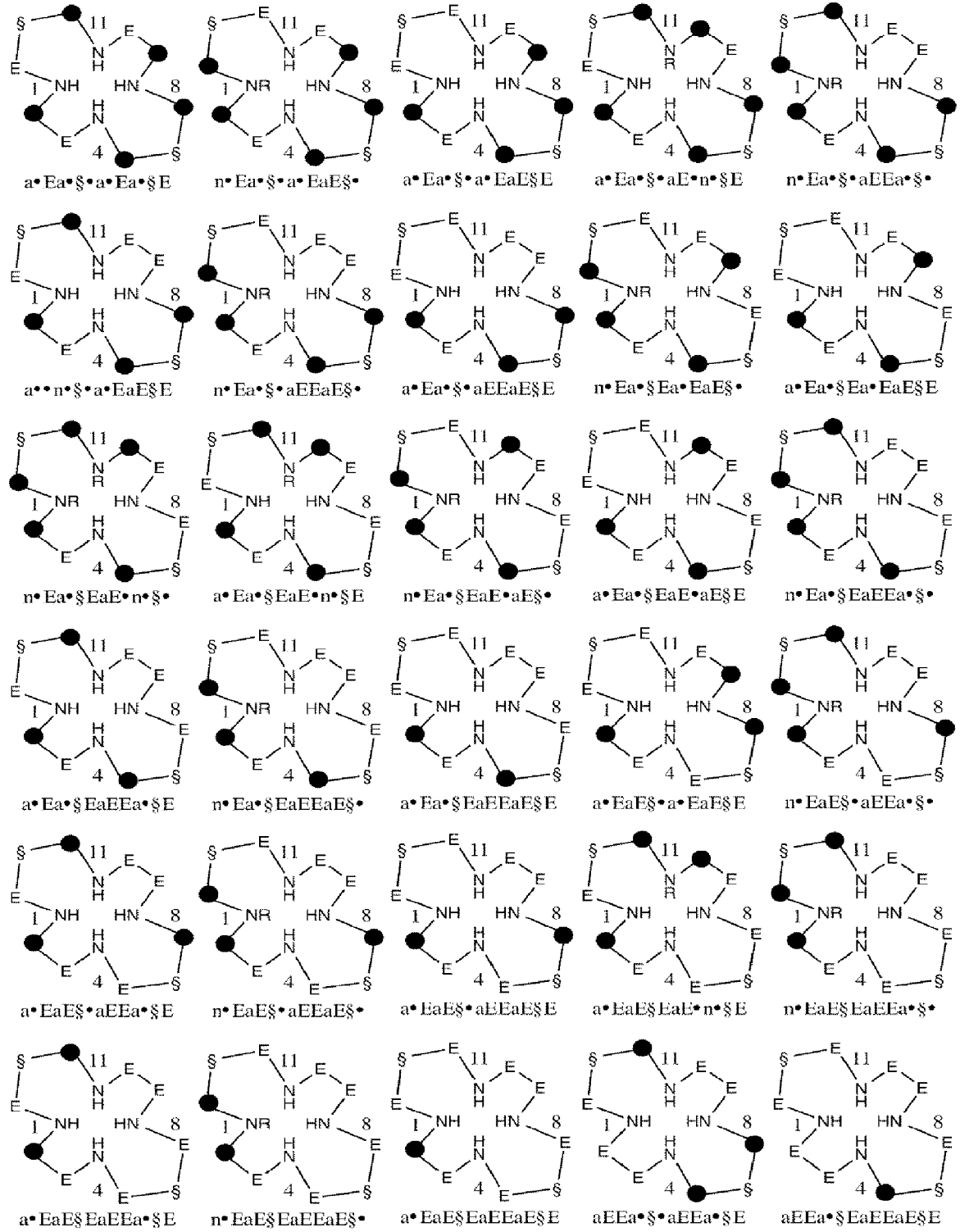
Figure 4O:
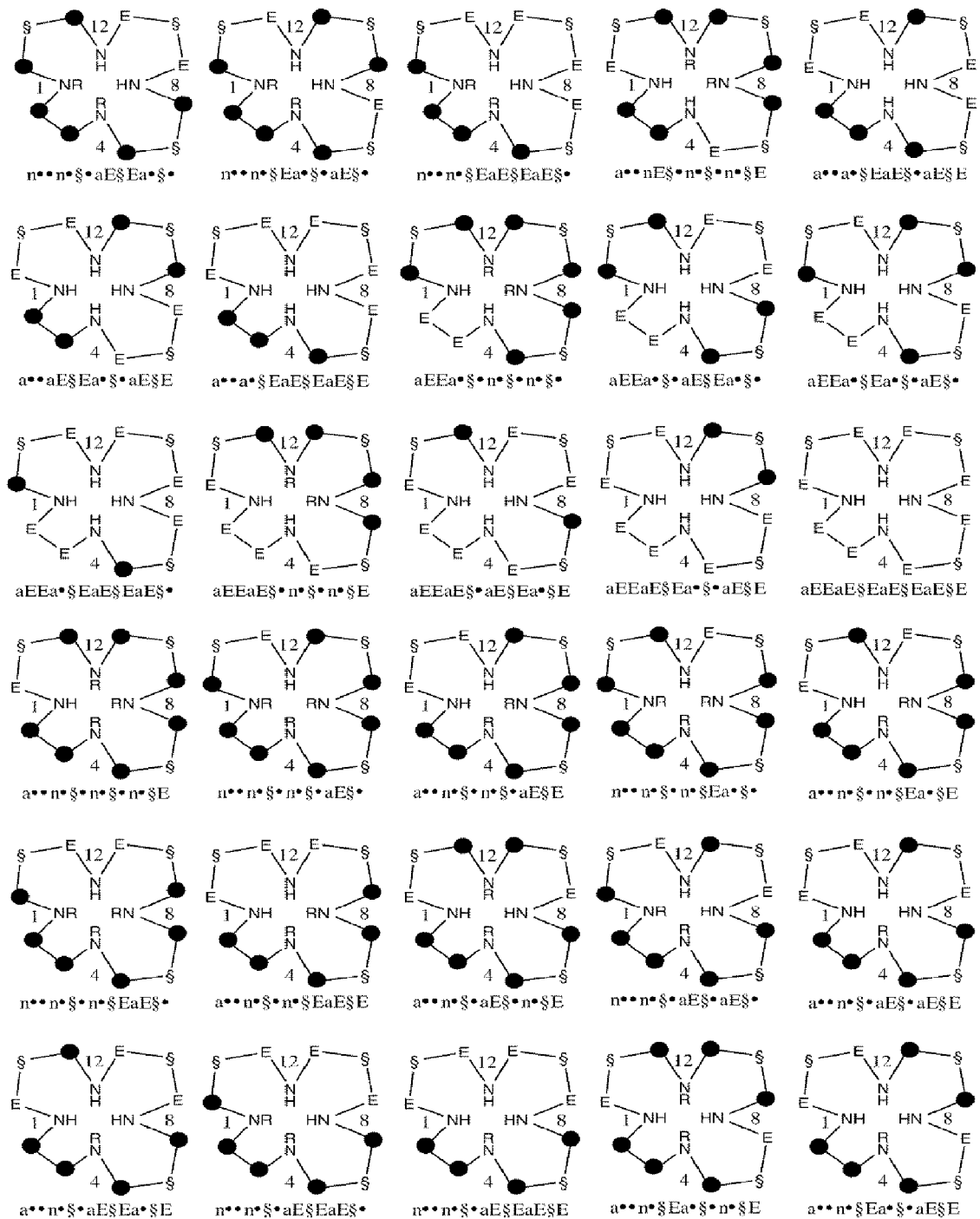
Figure 4P:
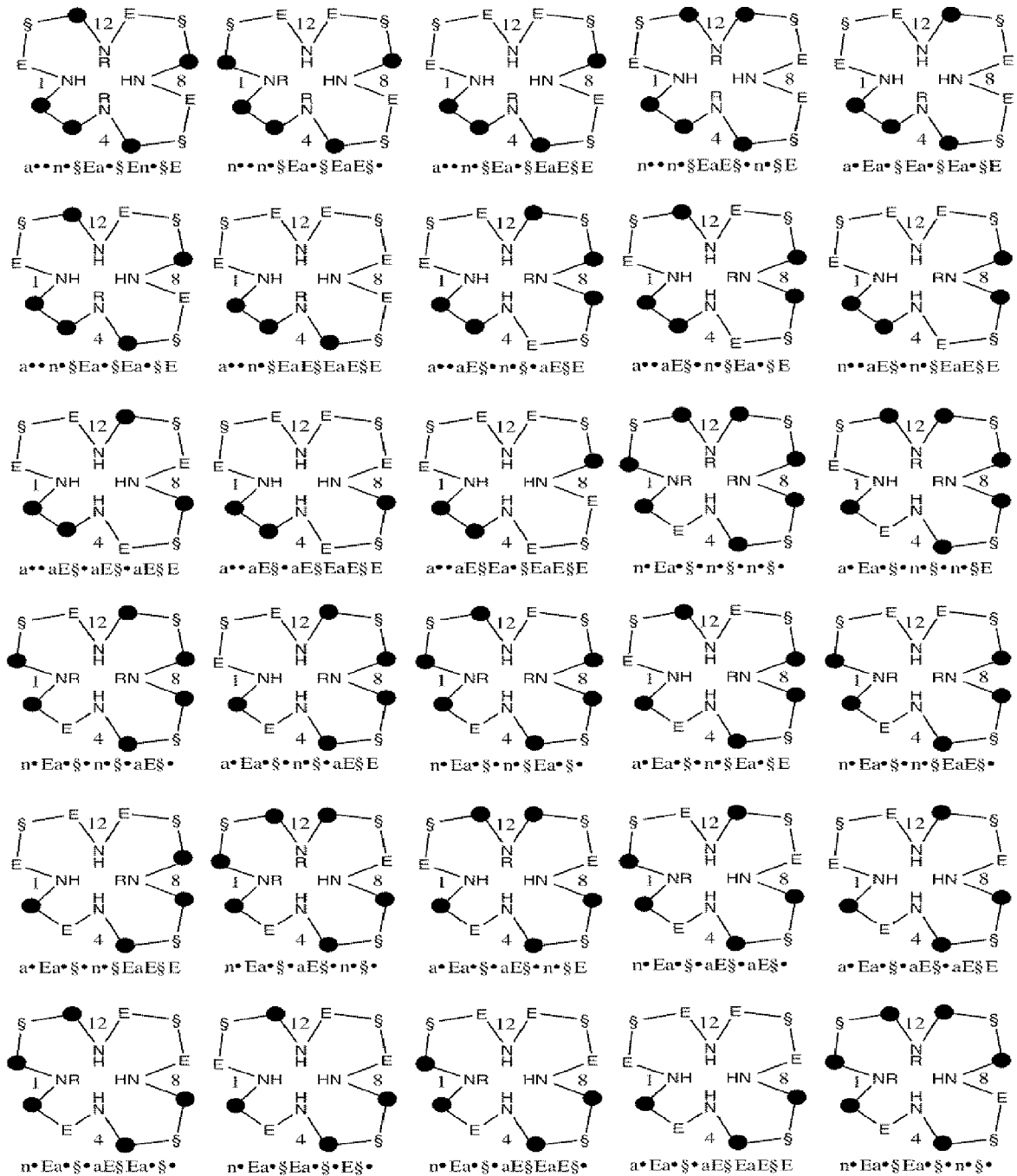
Figure 4Q:
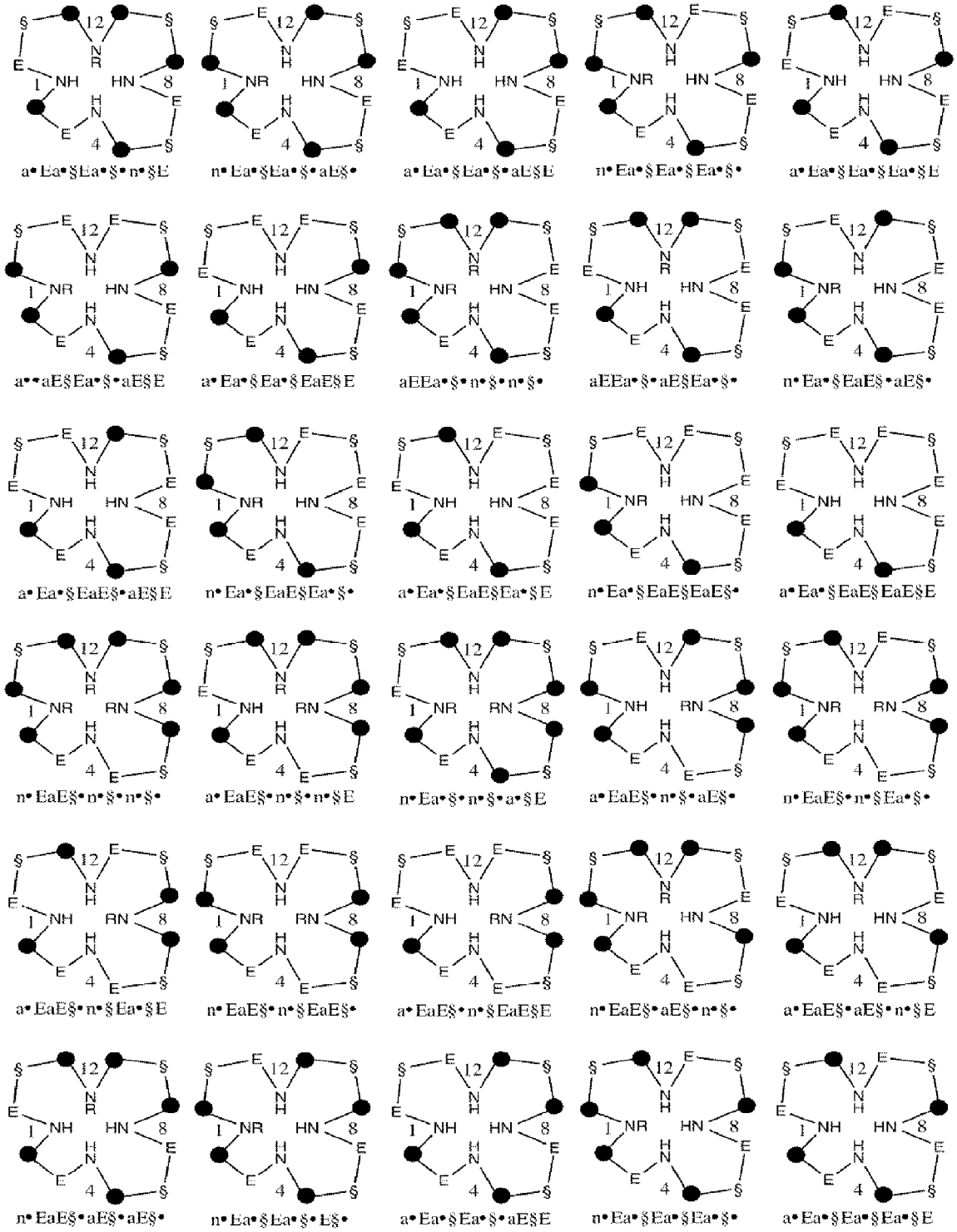
Figure 4R:
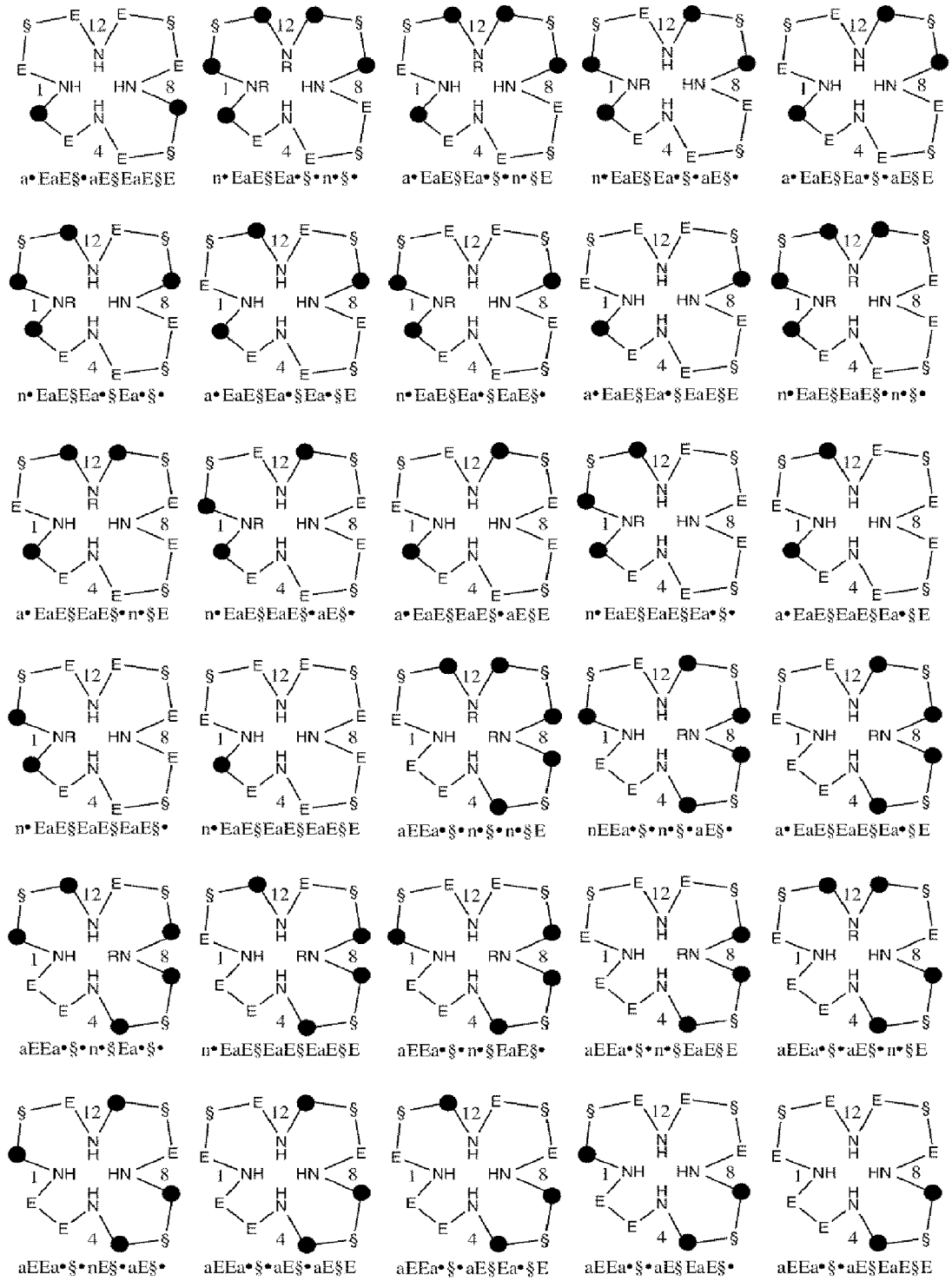
Figure 4S:
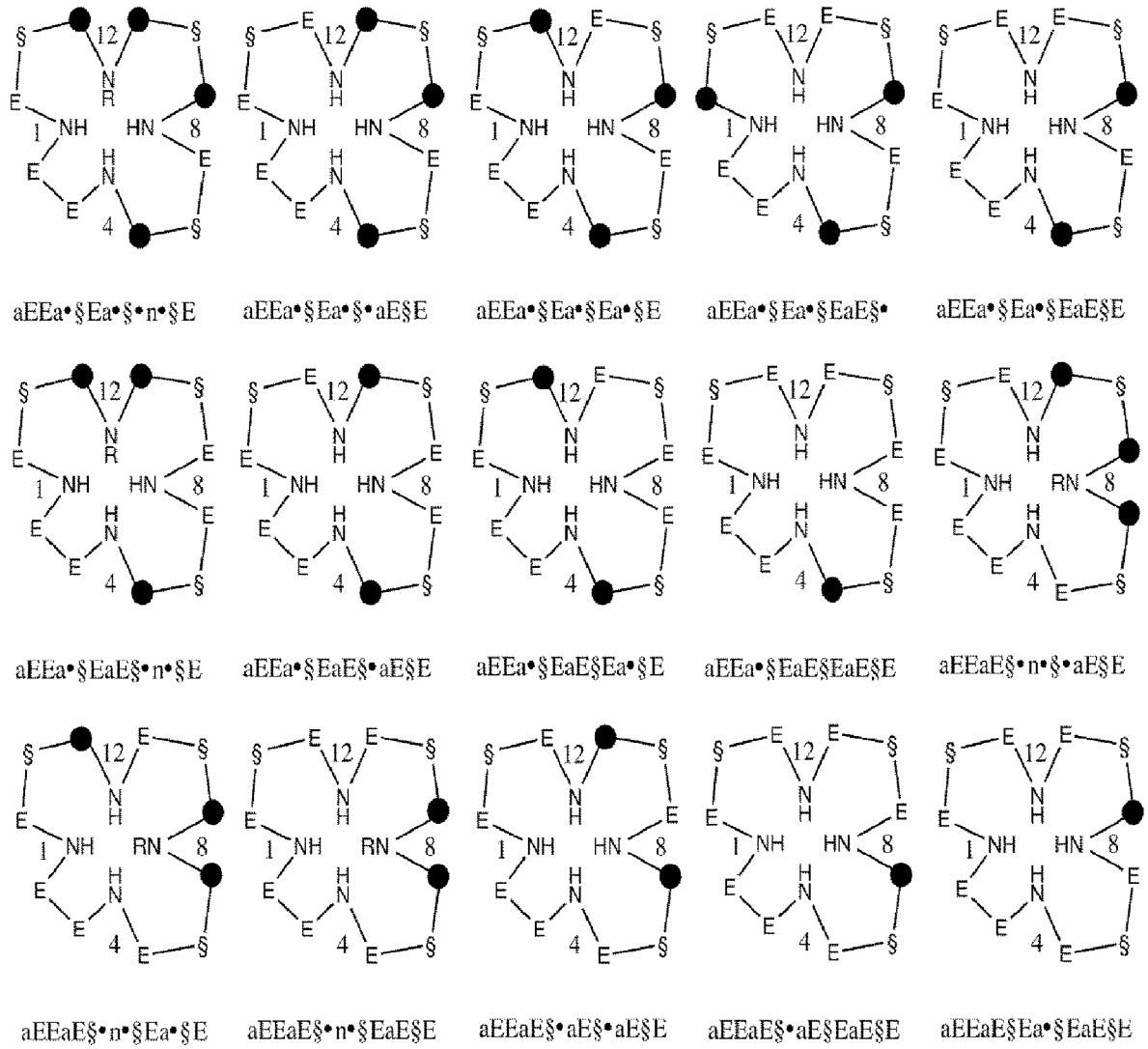
Figure 4T:
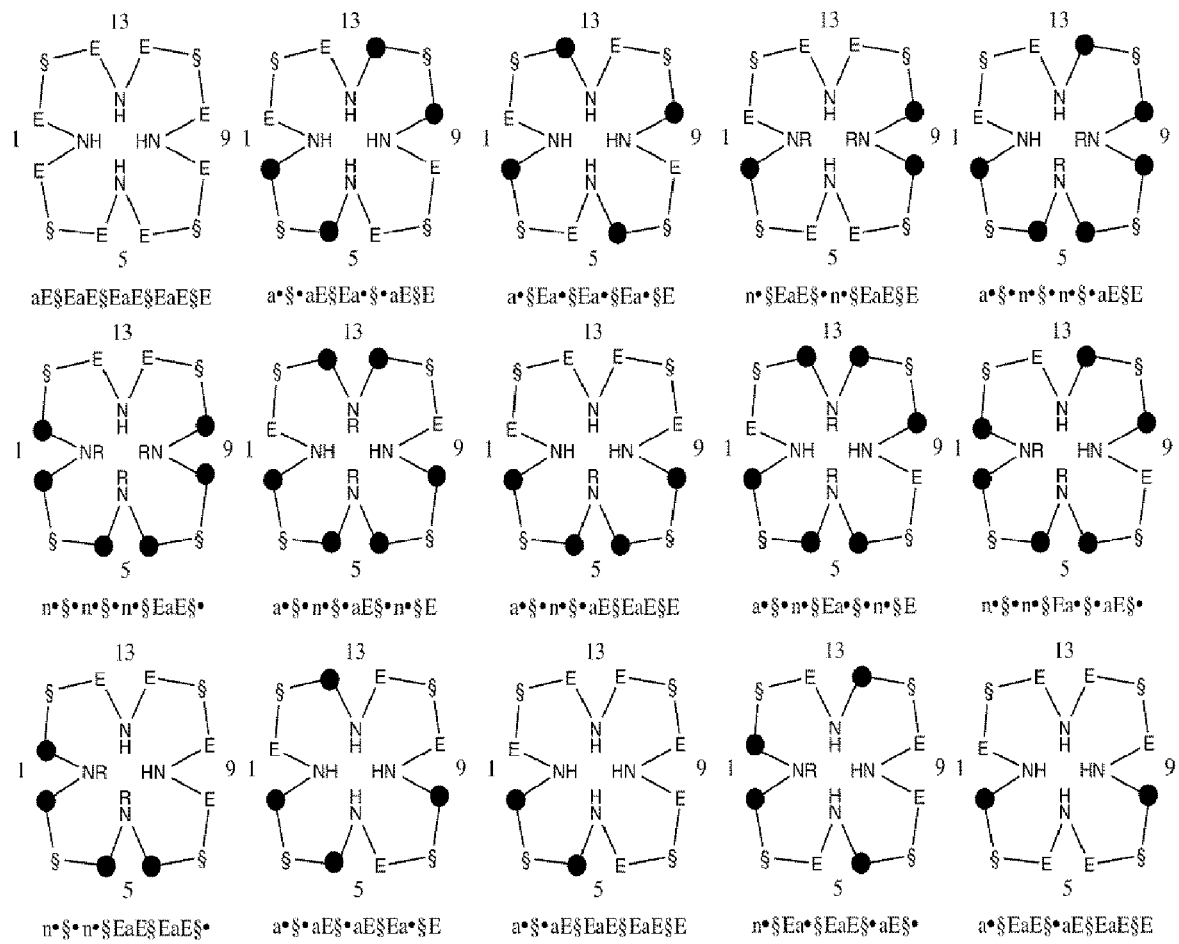
Figure 4U:
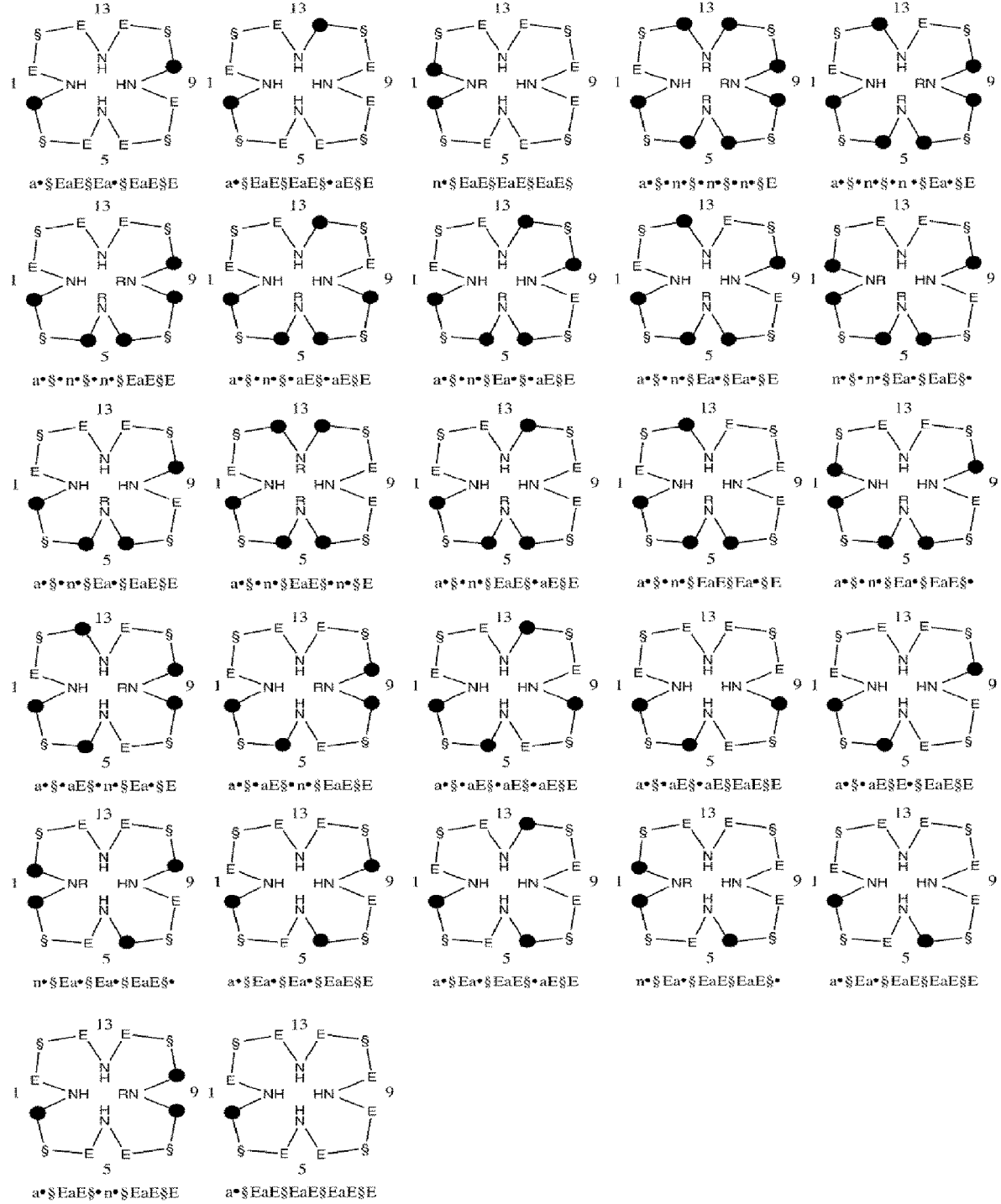
Figure 4V:
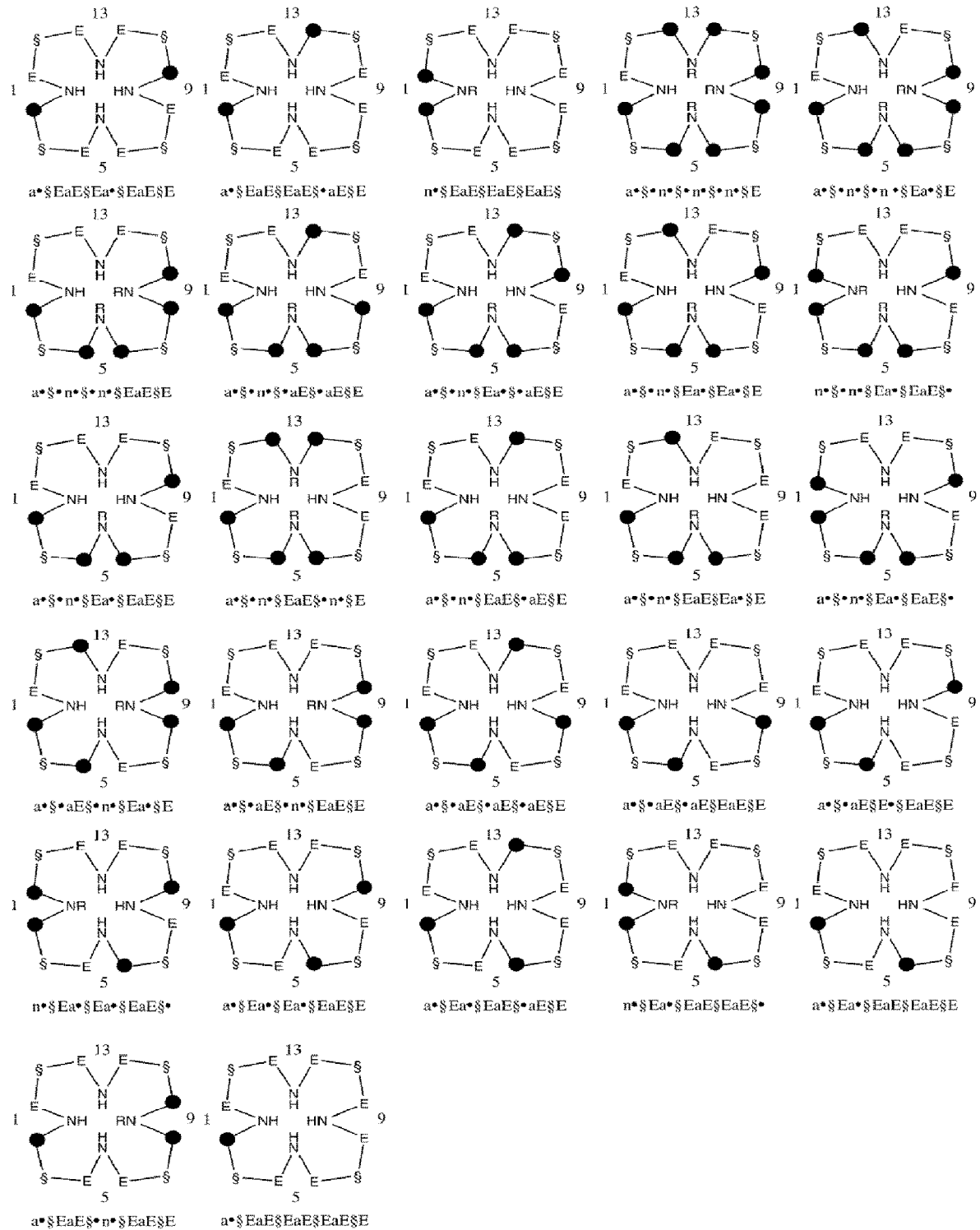

The complete range of amide containing macrocyclic compounds able to be synthesized from the starting materials identified in Table 2 and those that can be generated according to the procedures discussed below is shown in general terms in Table 3, shown in FIGS. 4A-V. Each unique combination has been listed pictorially and labeled with the shorthand notation of Structure 3 defined above.

The individual Bridge, Arm and Linker starting materials can either be obtained commercially or synthesized by standard techniques. Examples of syntheses for a few non-commercially available starting materials are provided herein and in the Experimental Section. A powerful alternative route for the preparation of substituted and unsubstituted malonates has been reported by A. P. Krapcho, E. G. E. Jahngen, Jr. and D. S. Kashdan: "α-carbalkoxylations of carboxylic acids. A general synthetic route to monoesters of malonic acids", Tet. Lett. 32, p. 2721-2723 (1974). The oxidatively robust NuRF containing tetradentate macrocycles shown in Table 3 may be synthesized without having to resort to the use of species that contain high energy N—N bonds, such as azides, hydrazines and azo constituents.

Schematics 1 to 3 below pictorially demonstrate substitution at the variable positions shown in Table 3. The remainder of this section discusses how to choose R substituents in general terms, and lists some representative examples of substituted Bridge, Arm and Linker starting materials in tabular form.

Single Node Substitution

Starting materials containing only one variable position may be substituted by a carbon atom bearing two R groups, a —C($R_a$)($R_b$)— unit, (in this context the dashes (—) refer to single bonds as opposed to amide bonds, and $R_a$ and $R_b$ are generic for any of the variable numbered R substituents in the schematics).

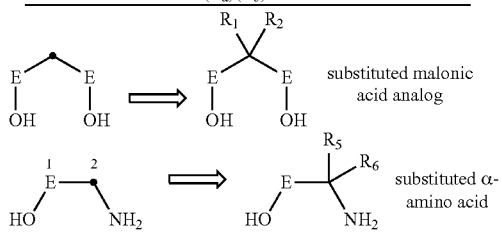

Schematic 1: Replacement of single variable position by a —C($R_a$)($R_b$)— unit.

For substitution at any single variable position the R groups on the —C($R_a$)($R_b$)— unit may be the same or different and are selected from the group consisting of hydrocarbons and heteroatom (e.g., halogen, N, O, Si, P, S) substituted hydrocarbons. Specific choices for the R groups other than $R_1$, $R_2$, $R_5$, and $R_6$ are from the following types/subtypes either singly or in combination (e.g. for R=arylsilylester, only aryl, esters and siloxanes are listed); H, ketones, aldehydes, carboxylic acids, hidden or protected/ activated carboxylic acids (see Table 1), esters, ethers, amines, hidden or protected/activated amines (see Table 1), imines, amides, nitro, sulphonyls, sulfones, sulfates, phosphoryls, phosphates, silyl, siloxanes, alkyl, alkenyl, alkynyl, halo, aryl, and compounds chosen from biological systems e.g. natural or unnatural amino acid side chains, heterocyclic rings, lactams, lactones, alkaloids, terpenes (steroids, isoprenoids), lipid or phospholipid chains. For single node substitution, fusion of the $R_a$ and $R_b$ groups at a position that is not the site of substitution, but α to the site of substitution yields a species doubly bonded to the node such as an oxo (═O), imine (═NR$_a$), or a substituted vinyl group (═CR$_a$R$_b$). Formation of imines or substituted vinyl groups constitutes a form of nodal migration. If the original $R_a$ and $R_b$ groups are fused at a site that is not the site of substitution and is not α to the site of substitution then a cyclic ring structure is formed. Fusion to R groups on E also results in cycles. If such cyclic groups are formed, additional R substituents on the cyclic groups are chosen in the same manner as for normal single node or multi node substitution (including the possibility of further R group fusions at one or more nodes to yield additional oxo, imine, substituted vinyl groups, or spiro, benzo, substituted benzo, heterocyclic, substituted heterocyclic, cycloalkyl, substituted cycloalkyl, cycloalkenyl or substituted cycloalkenyl ring structures). Preferred spiro/cyclic ring sizes are three-, four-, five- or six-membered rings.

Multi Node Substitution

Connection of nodes via R group fusion at sites that are not the points of attachment or a combination of sites that are not adjacent leads to the formation of cyclic structures, such as spiro, benzo, substituted benzo, heterocyclic, substituted heterocyclic, cycloalkyl, substituted cycloalkyl, cycloalkenyl or substituted cycloalkenyl ring structures. Five- and six-membered rings are preferred.

If cyclic groups are formed, or if there are residual R groups remaining from combination at adjacent sites, the residual R groups and the substituents on the cyclic groups are chosen in the same manner as for normal single node or multi node substitution (including the possibility of further R group fusions to yield additional spiro, benzo, substituted benzo, heterocyclic, substituted heterocyclic, cycloalkyl, substituted cycloalkyl, cycloalkenyl or substituted cycloalkenyl ring structures). If the cyclic groups formed are aromatic, G groups may be chosen as defined above.

An important point is that the definitions for both single node and multi node substitution can function recursively, e.g. substituted o-phenylene diamine=>substituted heterocyclic o-phenylene diamine=>substituted spiro-cycloalkyl heterocyclic o-phenylene diamine etc.

Schematic 2:
Replacement at two variables positions can be two —C($R_a$)($R_b$)— units or the two variable positions can be combined to make up part of an aryl or heterocyclic ring structure.

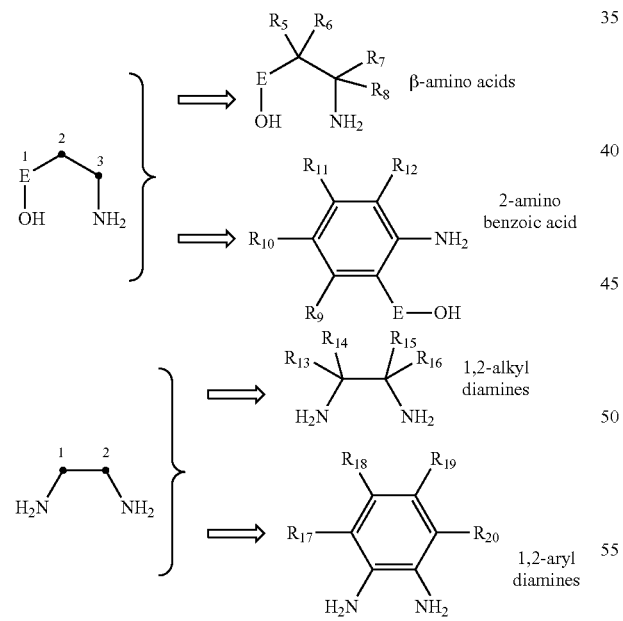

For multiple node substitution individual —C($R_a$)($R_b$)— positions are substituted identically as for single node substitution (see above). In addition to the types of substitution found for single nodes, it is also possible to combine or connect multiple nodes together via fusion of the R groups located on different nodes at sites that either are (combination), or are not (connection), the sites of attachment. Combination of sites that are adjacent leads to ethylenic units (—C($R_a$)═C($R_b$)—) a form of R group elimination.

Schematic 3:
Replacement as three variable positions can either be by three —C($R_a$)($R_b$)— units or two of the variable positions can be combined to make up part of an aryl or heterocyclic rings structure with the third position being replaced by a —C($R_a$)($R_b$)— unit or the three variable positions can all be combined to form part of a fused diaryl, fused aryl heterocyclic, or fused diheterocyclic ring structure.

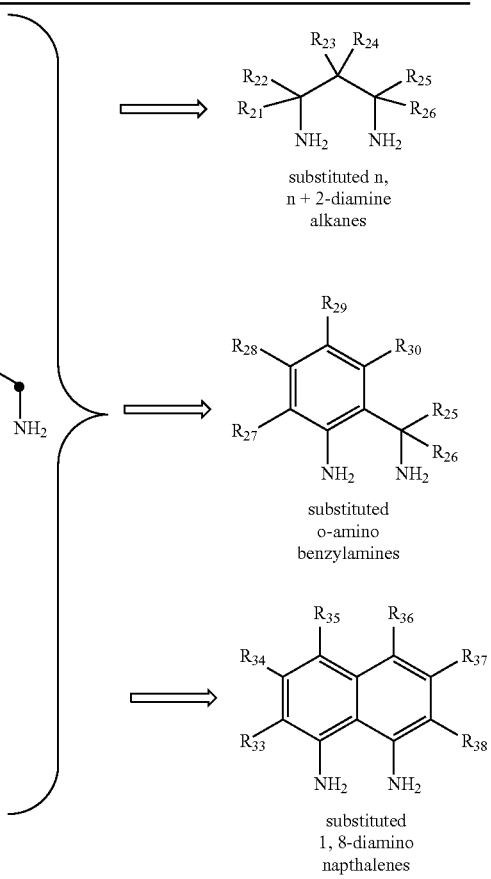

Additional potential oxidatively robust macrocyclic ligands are based on replacing the cyclic carbon of the six-membered ring of the metalated macrocycles described above with a heteroatom Z selected from Group 15 of the Periodic Table, preferably N, P or As, shown below.

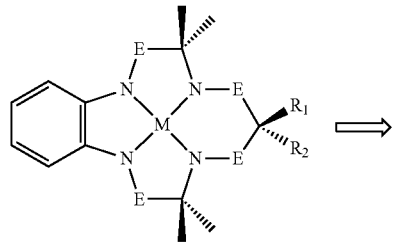

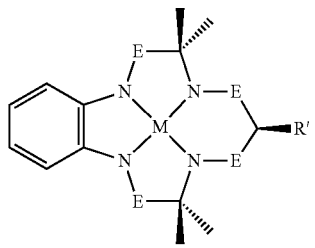

The metal containing macrocyclic ligand with a carbon at the central position of the six membered ring is shown on the left. A metal containing macrocyclic ligand with a Group 15 heteroatom, Z, at the central position of the six membered ring is shown at the right.

Complexes of the present invention must contain at least one E that is more stable towards nucleophilic attack than C=Q from the group consisting of S(=Q)$_2$, S(=Q)R'$_2$, S(=Q), P(=Q)R', PR'$_3$ and may include C=Q, where Q is oxygen or ZR' in one or more locations which may be the same or different. An example of a tetradentate macrocycle with 2 C=Q and 2 S(=Q)$_2$ is shown below as Structure 4 alongside two with S(=Q)$_2$ only, Structures 5 and 6. Representative carboxylic acids (including parent, hidden, and protected/activated forms) for preparation of C=Q containing macrocycles are included in Tables 1, 4, and 5. See U.S. Pat. No. 5,847,120.

Three exemplary complexes wherein E is S(=Q)$_2$ and Q is oxygen follow:

Structure 4

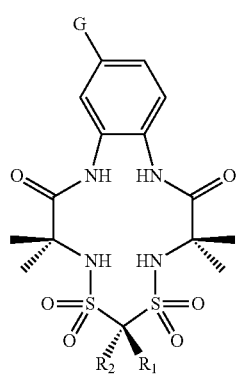

Structure 5

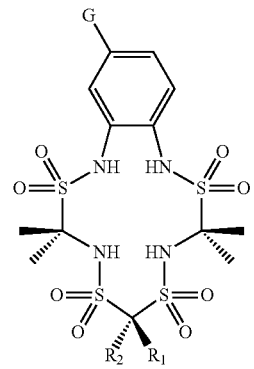

Structure 6

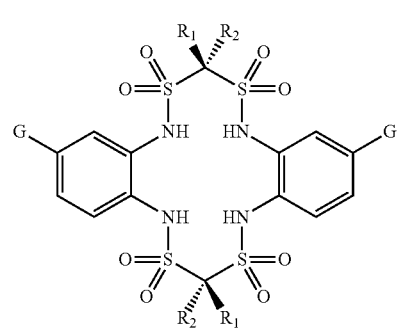

By way of example, the ligands shown as Structure 4 with G=H, R$_1$=R$_2$=H and G=NO$_2$, R$_1$=R$_2$=H (FIG. 1) and Structure 6 with G=H, R$_1$=R$_2$=H have been synthesized and metalated with iron to form examples of this entirely new class of catalyst. Structure 4 incorporates two sulfonamide NuRFs and both the G=H and G=NO$_2$ exhibit a phenomenal 100-fold increase in performance in the degradation of the target substrate over that of the parent catalysts containing four C=Q groups as detailed in FIG. 2B.

Starting from the basic tetradentate macrocycles, the macrocycles in Table 3 contain additional N or O substituents. Some representative synthetic approaches and starting materials are shown below. Malonic and oxalic acid derivatives, including sulfur and phosphorous containing derivatives (see Table 4), are first converted to terminal amides, then the terminal amides are reacted with an activated molecule to form an imide containing macrocyclic linker. Once the macrocyclic linker is obtained it is coupled with a diamine to form an imide containing macrocycle. This approach can generate a wide variety of imide containing macrocycles.

Malonic and oxalic acid derivatives including sulfur and phosphorous containing derivatives useful in the synthesis of imide containing macrocycles are shown in Sequence 6 below.

(Sequence 6)

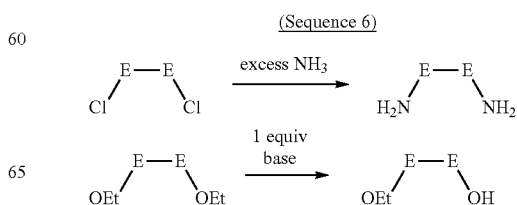

-continued

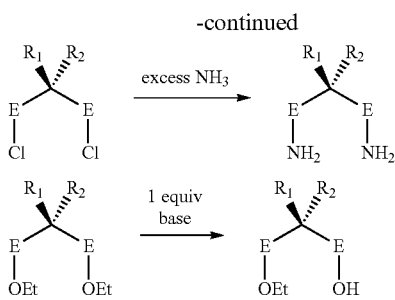

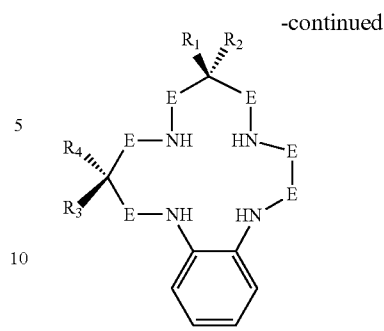

The synthesis of an asymmetrically substituted imide containing macrocycle by an extension of the synthetic methodology shown in Sequence 5 is shown below in Sequence 7.

Starting materials for N-substituted macrocycles are not as abundant commercially as for the corresponding O-substituted macrocycles. However, this problem can be overcome by taking advantage of the reactivity of the N group to synthesize the required starting materials. Standard synthetic techniques well known to those skilled in the art will yield a variety of N-substituted starting materials. For example, starting from a desired NR group, e.g. methylamine, aniline, N-trifluoro amine then N-alkylation or N-acylation can be employed to generate useful N-substituted synthetic intermediates as shown below in Sequence 7.

Synthesis of Asymmetrically Substituted Imide Containing Macrocycles by an Extension of the Existing Macrocyclic Synthetic Pathways.

N-Alkylation

N-alkylation can generate useful portions of the macrocyclic framework as shown below, Sequence 8.

(Sequence 8)

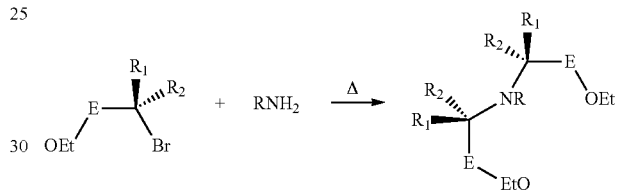

N-Acylation

Acylation of the amino acid with imidodisulfuryl chloride, Sequence 9, is expected to proceed in a straightforward manner.

(Sequence 7)

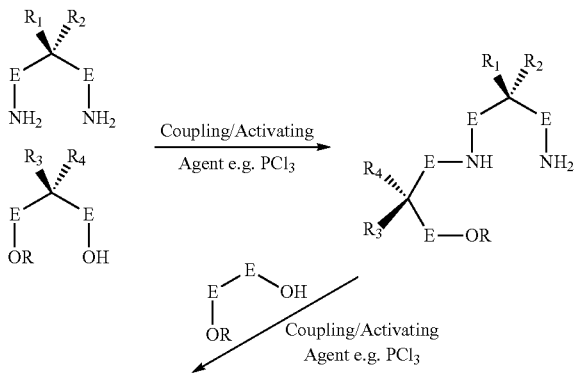

(Sequence 9)

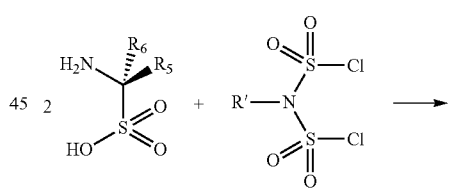

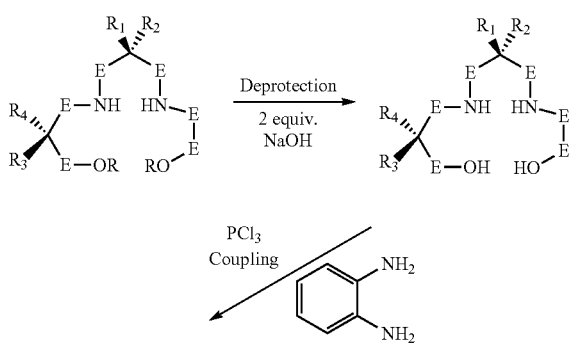

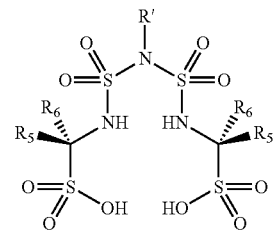

Acylation of an N-substituted imidodisulfuryl chloride is used in Sequence 4. An analogous reaction between imidodisulfuryl chloride N,N'-dimethylurea has been reported by Thielemann et al. Zeitschrift fur Anorg. and Allg. Chemie 1964, 329, 235-243, Sequence 10.

(Sequence 10)

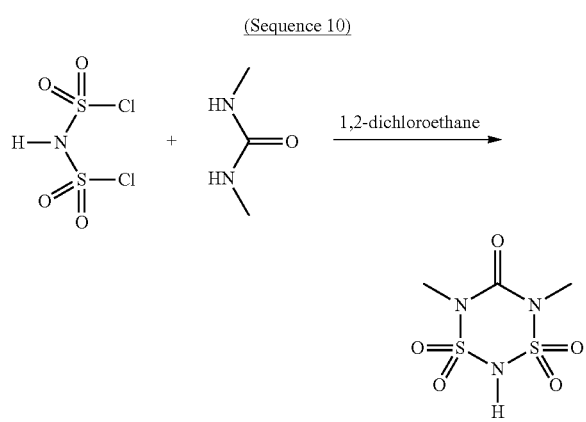

The synthetic methodology uses components that are similar to those reagents described as useful starting materials for the synthesis of the metallated macrocycles described above.

The N-substituted imidodisulfuryl chloride necessary for the synthesis is shown in Sequence 9. Imidodisulfuryl chloride can be readily prepared following the method of Beran (Zeitschrift fur Anorg. and Allg. Chemie 2005, 631, 55-59) and, with care, further converted into N-methyl imidodisulfuryl chloride with $CH_2N_2$ in benzene (Sapper, E. Zeitschrift fuer Naturforschung, Tl. B Anorg. Chemie, Org. Chemie, Biochem. Biophys. Biol. 1970, 25, 1490-1491.).

The possible variations in macrocyclic structure for Compound 1 with N and O substitution in the ligand framework are shown in Table 4 below.

The possible variations in macrocyclic structure for Compound 1 showing, for example, N substitution in the ligand framework are shown in Table 3.

Explanation of Symbols for Table 3:

The macrocyclic ligands shown in Table 3 are grouped into 6 families based on the sizes of the chelate rings formed upon metal coordination. For instance, a 5555 macrocycle consists of four five-membered metal containing chelate rings. Below each picture is the textual description of the substituents that form the particular macrocycle. The symbols start at the first position, indicated in the structures of Table 3 by a 1, and then progress around the ring in an anti-clockwise direction; it is implicit in the notation that the last position of the text string is connected to the first position in order to form the macrocycle. The meanings of the symbols are as follows:

"•" represents a carbon containing node able to be substituted as described previously with a pair of $R_1$, $R_2$, $R_5$, $R_6$, $R_7$, $R_8$, $R_9$, $R_{10}$, $R_{11}$, $R_{12}$, $R_{13}$, $R_{14}$, $R_{15}$, $R_{16}$ and $R_{17}$ as shown for variations of Compounds 1 and 2.

"a" represents an NH group.

"n" represents a DX group, wherein each D is a donor atom such as N and each X is a position for addition of a labile Lewis acidic substituent such as (i) H, deuterium, (ii) Li, Na, K, other alkali metals, (iii) alkaline earth metals, transition metals, rare earth metals, which may be bound to one or more than one D, (iv) or is unoccupied with the resulting negative charge being balanced by a nonbonded countercation of any description.

The X group may also form connections to other nearby substitutable (• or X) positions of the molecule to allow the formation of 4, 5 and 6 membered heterocyclic ring systems. X may be nothing as a special case, as shown below, which allows additional multiple bonding to take place between the D group and an adjacent carbon atom, but preserves the presence, for example, of the nitrogen lone pair as a donor to the metal ion.

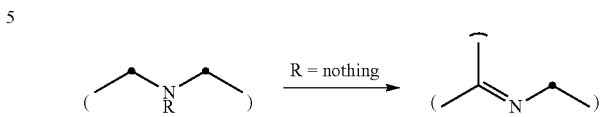

"e" represents one of the groups consisting of $S(=Q)_2$, $S(=Q)R_2'$, $S(=Q)$, $P(=Q)R'$, $PR_3'$ and $C=Q$, where Q is oxygen or ZR', wherein at least one E is more stable towards nucleophilic attack than $C=Q$ and is selected from the group consisting of $S(=Q)_2$, $S(=Q)R_2'$, $S(=Q)$, $P(=Q)R'$ or $PR_3'$ and is directly attached to one D.

"§" represents a special substitutable position, where the § group is chosen from •, ZR', $ZR_1'R_2'$, E, or ZH. Z is selected from the group consisting of O, N, P, As, or S. When Z is S, R' is optional. In other words, S may be bound to R' or may be unbound. R' is selected from the group consisting of (i) H, deuterium, (ii) Li, Na, K, or other alkali metals, (iii) alkaline earth metals, transition metals, or rare earth metals, (iv) oxygen, hydroxyl, phenoxy, halogen, a nitrogen containing group, or a carbon containing group selected from alkyl, alkenyl, alkynyl, aryl, alkoxy, phenoxy, halogenated alkyl, halogenated aryl, halogenated alkenyl, halogenated alkynyl, perhaloalkyl, perhaloaryl, or a substituted or unsubstituted cycloalkyl ring, a substituted or unsubstituted cycloalkenyl ring, a substituted or unsubstituted saturated heterocyclic ring, a substituted or unsubstituted unsaturated heterocyclic ring containing oxygen or any other Periodic Table Group 16 element or nitrogen, any other Periodic Table Group 15 element, or a substituted or unsubstituted unsaturated heterocyclic ring containing any such elements. $R_1'$ and $R_2'$ are the same or different, linked or nonlinked, and each is independently selected from the group consisting of substituents which are unreactive, form strong bonds intramolecularly within said $R_1'$ and $R_2'$ and with the Z of the Y unit to which each is bound, are unable due to size to interact with a metal center when X is occupied by a metal, and may also be sterically hindered and/or conformationally hindered to further restrict oxidative degradation of a metal complex of the compound when the complex is in the presence of an oxidizing agent, or together with an R substituent or two R substituents on an adjacent carbon, E or Z in the same Y unit, form a mono- or poly-substituted or unsubstituted saturated or unsaturated ring. By way of example, $R_1'$ and $R_2'$ may be selected from hydrogen or deuterium, which may be labile to acid dissociation, alkyl, aryl, halogen, haloalkyl, perhaloalkyl, haloaryl, perhaloaryl, particularly methyl, ethyl, $CF_3$, amino, substituted amino, amido (—NHCOR, —NRCOR, —$NHSO_2R$, —$NRSO_2R$, —$NHPO_2R$, —$NRPO_2R$), fully oxidized or partially oxidized or substituted or unsubstituted carboxylic, sulfonic, and phosphonic acid derivatives including, but not limited to, carboxylate (—$CO_2^-$, —CONHR, —$CONR_2$—$SO_2OH$, —$SO_2R$, —$SO_2NH_2$, —$SO_2NHR$, 13 $SO_2NR_2$, —$PO(OH)_2$, —$PO(OR)_2$, —$PR_3'$), and combinations thereof, or may form, together with the carbon atom to which both are bound, a substituted or unsubstituted three-, four-, five- or six-membered ring, such as a substituted or unsubstituted-cyclopropyl, -cyclobutyl, -cyclopentyl including but not limited to dibenzocyclopentyl, or -cyclohexyl.

Some representative examples of commercially available and/or synthetically versatile Linker, Arm and Bridge starting materials are shown in Tables 4, 5, and 6, respectively.

A macrocyclic amide containing compound having the desired chelate ring configuration shown in Table 3, i.e., 5555, 5556, 5566, 5656, 5666 or 6666, and variations thereof, can be constructed by reference to the general choice and combination of starting materials for various chelate configurations shown in Table 2, i.e., parent, protected/activated or hidden, followed by the choice of the specific starting materials from Tables 4, 5, and 6 or the materials synthesized by Sequences 5-10. Use of those functionally and structurally similar starting materials in the new synthetic method will provide a macrocyclic NuRF containing compound having a chelate ring configuration and substituent array suited to a particular end use. The symbol * in Tables 4, 5, and 6 indicates a substituent that is comparatively robust towards oxidation. The symbol ***‡ in the Tables indicates substituents that are very oxidatively robust.

Table 4 identifies some representative acid malonate derivatives, i.e. Linkers, of interest for the preparation of macrocyclic NuRF containing compounds, either † in parent, hidden, or protected/activated forms.

TABLE 4

The Malonates

Derivatives of Oxalic Acid (5ee)

| Registry # | Compound Name | Registry # | Compound Name |
| --- | --- | --- | --- |
| 79-37-8 | *Oxalyl Chloride | | |
| Sulfur and phosphorous derivatives of oxalic acid | | | |
| 14970-71-9 | Dithionic acid | 16346-26-2 | P,P'-diethyl ester hypophosphoric acid |
| 72889-77-1 | Disulfonyl chloride | 679-37-8 | P,P,P',P'-tetraethyl ester hypophosphoric acid |
| 15959-26-9 | Dithionous acid | 33486-47-4 | P,P'-diphenyl hypophosphonic acid |
| 7803-60-3 | Hypodiphosphoric acid | | |
| 44630-51-5 | Dimethyl hypophosphonic acid | | |
| 4342-00-1 | P,P'-dimethyl ester hypophosphoric acid | | |
| Derivatives of Malonic Acid (6ee) | | | |
| Disubstituted malonates | | | |
| 31696-00-1 | *Diethyl butylethyl-malonate | | *Diethyl di-n-octyl-malonate |
| 00596-76-9 | *Diethyl butylhexyl-malonate | 24251-93-2 | *Diethyl di-n-pentyl-malonate |
| 00083-27-2 | *Diethyl butylmethyl-malonate | | *Diethyl di-2-propenyl-malonate |
| | *Diethyl butylethyl-malonate | 03195-24-2 | *Diethyl di-n-propyl-malonate |
| | *Diethyl butylpentyl-malonate | | *Diethyl ethylheptyl-malonate |
| | *Diethyl butylpropyl-malonate | | *Diethyl ethylhexyl-malonate |
| | *"2,2-Diethyl-butyric acid" | 00133-13-1 | *Diethyl ethyl (1-methyl butyl) malonate |
| 18719-43-2 | *Diethyl "1,1-cyclo-butane dicarboxylate" | | *Diethyl ethylmethyl-malonate |
| 53608-93-8 | *Diethyl "1,1-cyclo-propane dicarboxylate" | 02049-70-9 | *Diethyl ethyl (1-methyl-propyl) malonate |
| 01559-02-0 | *Diethyl decylethyl-malonate | | *Diethyl ethylnonyl-malonate |
| 05077-96-3 | *Diethyl decylmethyl-malonate | 05408-35-5 | *Diethyl ethyloctyl-malonate |
| | *Diethyl diallyl-malonate | 00076-67-5 | *Diethyl ethylpentyl-malonate |
| 00597-55-7 | *Diethyl di-n-butyl-malonate | | *Diethyl ethylphenyl-malonate |
| 00596-75-8 | *Diethyl di-n-decyl-malonate | 71691-56-0 | *Diethyl ethylpropyl-malonate |
| | *Diethyl diethyl-malonate | | *Diethylmethyl(2-methyl-butyl) malonate |
| | *Diethyl di-n-heptyl-malonate | | *Diethyl methyl(2-methyl-propyl) malonate |
| | *Diethyl di-n-hexyl-malonate | 34009-61-5 | *Diethyl methylnonyl-malonate |
| | †Diethyl dimethyl-malonate | 01575-67-3 | †Diethyl methylphenyl-malonate |

TABLE 4-continued

| | The Malonates | | |
|---|---|---|---|
| 01619-62-1 | *Diethyl di-n-nonyl-malonate | 58447-69-1 | *Diethyl methylpropyl-malonate |
| | *"1,1-cyclopropane dicarboxylate" | 00083-27-2 | *Diethyl methyl-iso-propylmalonate |
| | *"1,1-cyclopentane dicarboxylate" | | *"1,1-cyclobutane dicarboxylate" |
| | †ditrifluoromethyl malonic acid | | *"1,1-cyclohexane dicarboxylate" |
| | †difluoro malonic acid | | †ditrifluoroethyl malonic acid |
| | | | †dichloro malonic acid |

Sulfur and phosphorous derivatives of malonic acid
Including acid, acid chloride, and ester forms and the following substituents (where applicable)

| | | | |
|---|---|---|---|
| | 1,1-dichloro- | | 1-fluoro- |
| | 1,1-difluoro- | | 1-chloro- |
| | 1,1-ethane- | | 1-alkyl- |
| | 2,2-propane- | | 1-phenyl- |
| | 1,1,1,3,3,3-hexafluoropropane-2,2- | | |
| | 2,2,2-trifluoroethane-1,1- | | |
| | 1-fluoro-1-chloro- | | |
| 5799-68-8 | Methane disulfonyl dichloride | 503-40-2 | Methanedisulfonic acid |
| | Methanedisulfinyl dichloride | 1984-15-2 | P,P'-methylenebis-phosphonic acid |
| 247090-64-8 | P,P'-dimethyl ester methylenebis-phosphonic acid | 81050-37-5 | P,P'-methylenebis-phosphinic acid |
| 73300-71-7 | 1-phosphono-methanesulfonic acid | 99591-77-2 | 1,1-Ethanedisulfonyl dichloride |
| 86107-36-0 | Methanetrisulfonyl trichloride | | |

Other reactants may be synthesized according to the literature. For example, 1-chloro-methanedisulfonyl dichloride and 1,1-methanedisulfonyl dichloride can be prepared from methane disulfonyl dichloride following the method of Fild and Rieck (Chemiker-Zeitung (1976), 100(9), 391-2). Preparation of $R_1R_2C(SO_2Cl_2)_2$ (alkyl-methanedisulfonyl dichloride) is described in Murakami et al, Japanese Patent No. 2014062076, A to Sumitomo Seika Chemicals Co., Ltd. Those skilled in the art will understand that there are 200 or more variations of starting materials in the listed subcategories (for example, 1-chloro-methanedisulfonyl dichloride, 2,2-propane disulfonyl dichloride) that may be prepared from their parent compound or de novo following methods such as those of Fild and Rieck (for halogenation) or Murakami (for alkylation).

Table 5 identifies some representative α and β-amino acids, i.e. Arms, of interest for the preparation of macrocyclic tetradentates, either in parent, hidden, or protected/activated form.

TABLE 5

The Amino Acids

Derivatives of α-Amino Carboxylic Acids (5ae)

| | |
|---|---|
| *R(−)-2-amino-2-methyl butanedioic acid | *S(−)-2-amino-2-methyl-4-pentenoic acid monohydrate |
| *S(+)-2-amino-2-methyl butanedioic acid | *2-amino-2-norbornane carboxylic acid |
| *S(+)-2-amino-2-methyl butanoic acid hydrate | *R(−)-2-amino-2-phenylbutyric acid |
| *2-amino-2-methyl butyric acid | *1-aminocyclopropane-1-carboxylic acid |
| 2-amino-2-methyl glutaric acid | *1-aminocyclobutane-1-carboxylic acid |
| *R(−)-2-amino-2-methyl-3-hydroxy propanoic acid | *1-aminocyclopentane-1-carboxylic acid (cycloleucine) |
| *S(+)-2-amino-2-methyl-3-hydroxy propanoic acid | *1-aminocyclohexane-1-carboxylic acid |
| *(S)-2-amino-2-methyl-4-phosphonobutanoic acid | *S(+)-2-amino-2-methyl-3-phenyl propanoic acid |
| †±,±-diphenyl glycine | †±-phenyl alanine ((+/−)a-methyl-a-phenyl glycine) |
| †±-amino-sobutyric acid (a-methyl alanine) | *S(+)-2-amino-2-phenylbutyric acid |
| *cis-1-amino-3-(2-phosphonoacetyl) cyclobutane-1-carboxylic acid | |

TABLE 5-continued

The Amino Acids

Sulfur and phosphorous derivatives of α-amino acids

| | | | |
|---|---|---|---|
| 13881-91-9 | Aminomethane sulfonic acid | | Dichloro aminomethanesulfonic acid |
| 1636-31-3 | 1-amino-ethanesulfonic acid | | Difluoro aminomethanesulfonic acid |
| 120766752-4 | 2-amino-2-propanesulfonic acid | | Ditrifluoro aminomethanesulfonic acid |
| 118201-3-5 | Aminomethanesulfinic acid | | 1-amino-ethanesulfinic acid |
| | 2-amino-2-propanesulfinic acid | | Difluoro aminomethanesulfinic acid |
| 56146-83-9 | methyl (chlorosulfonyl)acetate | | ethyl 2-(chlorosulfonyl)-2-methylpropanoate |
| | chlorosulfonyl acetic acid ethyl ester | | |
| 996-28-1 | (Aminomethyl)-phosphinic acid | | Chlorocarbonylphosphinic acid |
| 74333-44-1 | P-(1-aminoethyl)-phosphinic acid | | Fluorocarbonylphosphinic acid |
| | P-(2-amino-2-propyl)-phosphinic acid | | |
| 15901-11-8 | P-(aminomethyl)-P-methyl-phosphinic acid | | Chlorocarbonyl (methyl)phosphinic acid |
| | (1-aminoethyl)(methyl) phosphinic acid | | Fluorocarbonyl (methyl)phosphinic acid |
| | (2-aminopropan-2-yl)-(methyl)phosphinic acid | | |
| 1066-51-9 | P-(1-aminomethyl)-phosphonic acid | | chlorocarbonylphosphonic acid |
| 5035-79-0 | P-(1-amino-1-methylethyl)-phosphonic acid | | |
| 14561-07-0 | (1-amino-1-methylethyl)-phosphonic acid monoethyl ester | 745718-87-0 | (aminocarbonyl)-phosphonic acid mono methyl ester |
| 99305-71-2 | P-(aminomethyl)-phosphonic acid mono methyl ester | | |

Derivatives of β Carboxylic Acids (6ae)

*† The β-amino acids derived from 2-amino-benzoic acid (anthranilic acid) are quite oxidatively robust

| Registry # | Compound containing 2-amino-benzoic acid, 2-aminobenzenesulfinic acid, 2-aminobenzenesulfonic acid, (2-aminophenyl)phosphonic acid and its esters, (2-aminophenyl)(alkyl) phosphinic acid and its esters | Registry # | Compound containing 2-amino-benzoic acid, 2-aminobenzenesulfinic acid, 2-aminobenzenesulfonic acid, (2-aminophenyl)phosphonic acid and its esters, (2-aminophenyl)(alkyl) phosphinic acid and its esters |
|---|---|---|---|
| | †(o-amino-benzoic acid, anthranilic acid) | | †(o-amino-benzoic acid, anthranilic acid) |
| | †4-nitro- | | *3-methoxy- |
| | †5-nitro- | | *5-methoxy- |
| | *3-methyl- | | *5-hydroxy- |
| | *4-methyl- | | *3-hydroxy-hydrochloride |
| | *5-methyl- | | †4-fluoro- |
| | *6-methyl- | | †5-fluoro- |
| | *3,5-diiodo- | | †6-fluoro- |
| | *4,5-dimethoxy- | | *4-chloro-5-sulfamoyl- |
| | *3,4-dimethyl- | | †3-chloro- |
| | *3,5-dimethyl- | | †4-chloro- |
| | *3,6-dimethyl- | | †5-chloro- |

TABLE 5-continued

The Amino Acids

| | †3,5-dichloro- | | †6-chloro- |
| | *3,5-dibromo- | | *3-bromo-5-methyl- |
| | 3,5-dibromo-6-fluoro- | | |
| | 3,5-dinitro- | | †3,4,5,6-tetrafluro- |
| | | | *3,4,5-trimethoxy- |

| Registry # | Other β-amino carboxylic acids | Registry # | Other β-amino carboxylic acids |
|---|---|---|---|
| | | 5959-52-4 | †3-amino-2-naphthoic acid |
| 5434-20-8 | *3-amino-pthalic acid | 5345-47-1 | *2-amino-nicotinic acid (2-aminopyridine-3-carboxylic acid) |
| 614-19-7 | *β-amino-hydrocinnamic acid (D,L-3-amino-3-phenyl-propionic acid) | 82-24-6 | †1-amino-anthraquinone-2-carboxylic acid |
| 52834-01-2 | *2-amino-4,6-dimethyl-3-pyridinecarboxylic acid hydrochloride | 1664-54-6 | *3-amino-3-phenyl-propionic acid |
| 54711-21-6 | *5-amino-4-cyano-1-methyl-pyrazole | 50427-77-5 | *5-amino-1-phenylpyrazole-4-carboxamide |
| 698-29-3 | *4-amino-5-cyano-2-methyl pyrimidine | 72-40-2 | *5(4)-aminoimidazole-4(5)-carboxamide hydrochloride |
| | *4-amino-5-cyano-2-methoxy pyrimidine | 68302-09-0 | *2-amino-7-ethyl-5-oxo-5H-[1]benzopyrano[2,3-b]pyridine-3-carbonitrile |
| 41680-34-6 | *3-aminopyrazole-4-carboxylic acid | 22603-53-8 | *2-amino-3,5-dinitrobenzonitrile |
| 87550-19-4 | *3,6-dinitrophthalic acid pyridine salt | | *5-amino-4-cyano-1-(4-chlorophenyl)pyrazole |
| 5424-01-1 | *3-amino pyrazine-2-carboxylic acid | | *5-amino-4-cyano-1-(4-nitrophenyl)pyrazole |
| 10312-55-7 | *2-amino terepthalic acid | 16617-46-2 | *5-amino-4-cyano pyrazole |
| | | 6375-47-9 | *3-amino-4-acetamido anisole |

Other sulfur and phosphorous derivatives of β-amino acids

| Registry # | | Registry # | |
|---|---|---|---|
| 2041-14-7 | (2-aminoethyl)phosphonic acid | | (2-aminoethyl)(alkyl) phosphinic acid |
| 107-35-7 | 2-aminoethane-1-sulfonic acid (taurine) | 300-84-5 | 2-aminoethane-1-sulfinic acid |
| 60-23-1 | 2-amino-ethanethiol | 342613-81-4 | 3-amino-2,3-dimethyl-butanethiol |
| 1207667-50-2 | 3-amino-2,3-dimethyl-2-butanesulfonic acid | | |
| 1355450-89-3 | P-(1-amino-9,10-dihydro-9,10-dioxo-2-anthracenyl)-phosphonic acid | 126764-61-2 | 3-amino-2-naphthalenethiol |
| 83-62-5 | 1-amino-9,10-dioxo-9,10-dihydroanthracene-2-sulfonic acid | 856119-86-3 | 3-amino-6-hydroxy-2-sulfo-benzoic acid |
| 581-74-8 | 3-amino-2-naphthalenesulfonic acid | 16250-07-0 | 2-amino-3-pyridinesulfonic acid |
| 1162667-35-7 | P-(2-amino-3-pyridinyl)-phosphonic acid diethyl ester | 97272-96-3 | β-amino-benzeneethanesulfonic acid |
| 59374-52-6 | (2-amino-2-phenylethyl)-phosphonic acid | 1233181-68-4 | P-(2-amino-2-phenylethyl)-phosphonic acid dimethyl ester |
| 117186-64-8 | 3-amino-benzeneethanesulfonic acid | 933719-38-1 | P-[2-(3-aminophenyl) ethyl]-phosphonic acid |
| 105513-48-2 | 5-amino-1-phenyl-pyrazole-4-sulfonic acid | 89180-11-0 | 4-amino-2-methyl-5-pyrimidinethiol |
| 1249553-91-0 | 3-amino-1H-pyrazole-4-thiol | 1533597-03-3 | 5-amino-1-methyl-pyrazole-4-thiol |
| 31613-87-3 | 3-amino-2(1H)-pyrazinethione | 31613-88-4 | 3-amino-5,6-dimethyl-2(1H)-pyrazinethione |
| 34972-19-5 | 3-amino-2(1H)-Quinoxalinethione | | |

TABLE 5-continued

The Amino Acids

| | | | |
|---|---|---|---|
| 18889-18-4 | 3-amino-4-mercapto-benzoic acid | 106206-23-9 | 3-amino-4-sulfo-benzoic acid |
| 88-64-2 | 4-(acetylamino)-2-amino-benzenesulfonic acid | | 3-chlorosulfonyl-propionic acid methyl ester |

Table 6 identifies some representative diamines, i.e. 10 Bridges, of interest for the preparation of macrocyclic tetraamides, either in parent, hidden, or protected/activated forms. Amine and protected/activated or hidden amine functionalities are used interchangeably.

TABLE 6

The Diamines

Derivatives of 1,2-Aryl Diamines (5aa)
*† all of the aryl diamines shown are comparatively robust towards oxidation.

| Registry # | Compound containing o-Phenylenediamine | Registry # | Compound containing o-Phenylenediamine |
|---|---|---|---|
| 95-54-5 | Substituents = 0 †(1,2-Benzenediamine) No. of Unique Substituents = 1 | 95-54-5 | Substituents = 0 †(1,2-Benzenediamine) No. of Unique Substituents = 1 |
| 18645-88-0 | †3-fluoro- | 21745-41-5 | †3-chloro- |
| 367-31-7 | †4-fluoro- | 95-83-0 | †4-chloro- |
| 153505-39-6 | †3,4-difluoro- | 1668-01-5 | †3,4-dichloro- |
| 2369-29-1 | †3,5-difluoro- | 5233-04-5 | †3,5-dichloro- |
| 2369-30-4 | †3,6-difluoro- | 21732-93-4 | †3,6-dichloro- |
| 76179-40-3 | †4,5-difluoro- | 5348-42-5 | †4,5-dichloro- |
| 168966-54-9 | †3,4,5-trifluoro- | 30064-28-9 | †3,4,5-trichloro- |
| 363-74-6 | †3,4,6-trifluoro- | 1962-10-3 | †3,4,6-trichloro- |
| 2993-07-9 | †3,4,5,6-tetrafluoro- | 877-12-3 | †3,4,5,6-tetrachloro- |
| 1575-36-6 | *3-bromo- | 34446-43-0 | *3-iodo- |
| 1575-37-7 | *4-bromo- | 21304-38-1 | *4-iodo- |
| 1575-38-8 | *3,5-dibromo- | 144793-03-3 | *3,6-diiodo- |
| 69272-50-0 | *3,6-dibromo- | 76179-43-6 | *4,5-diiodo- |
| 49764-63-8 | *4,5-dibromo- | | |
| | No. of Unique Substituents = 2 | | No. of Unique Substituents = 2 |
| 75293-95-7 | *4-bromo-5-chloro- | 132915-81-2 | †3-chloro-4-fluoro- |
| 16429-44-0 | *5-bromo-3-chloro- | 153505-33-0 | †3-chloro-5-fluoro- |
| 172215-94-0 | *3-bromo-4,5-dichloro- | 139512-70-2 | †4-chloro-5-fluoro- |
| 98138-54-6 | *4-bromo-3,5-dichloro- | 153505-43-2 | *5-chloro-3-iodo- |
| 74908-80-8 | *3,5-dibromo-4-chloro- | 153505-34-1 | †3-chloro-4,5-difluoro- |
| 115440-10-3 | *3-bromo-5-fluoro- | 170098-84-7 | †4-chloro-3,5-difluoro- |
| 153505-37-4 | *4-bromo-5-fluoro- | 156425-14-8 | †4-chloro-3,5,6-trifluoro- |
| 153505-35-2 | *3-bromo-4,5-difluoro- | 153505-47-6 | *4,5-dichloro-3-iodo- |
| 156425-12-6 | *4-bromo-3,5,6-trifluoro- | 18225-92-8 | †3,4,6-trichloro-5-fluoro- |
| | | 153505-45-4 | *5-fluoro-3-iodo- |

| Registry Number | Additional 1,2-Benzenediamines | Registry Number | Additional 1,2-Benzenediamines |
|---|---|---|---|
| | *4,5-dimethyl- | | *4-methyl- |
| | †4,5-dinitro- | | †4-nitro- |
| 88580-71-6 | *4,5-dimethoxy- | | *4-methoxy- |
| | *4,5-diamino- | | *4-amino- |
| | †4,5-diacetamido- | | †4-acetamido- |
| | †4,5-ditrifluoromethyl- | | †4-trifluoromethyl- |
| | †4,5-dicyano- | | †4-cyano- |
| | *4,5-dihydroxy | 615-72-5 | *4-hydr0xy (3,4-diamino-phenol) |
| | | 59649-56-8 | *3-hydroxy (2,3-diamino-phenol) |
| | Other n,n + 1-Diamines | | Other n,n + 1-Diamines |
| | †1,1,2,2-tetramethyl ethylene diamine | 452-58-4 | *2,3-diamino pyridine |
| 7598-26-7 | *2-amino-3-nitro-5-methyl pyridine | 54-96-6 | *3,4-diamino pyridine |

TABLE 6-continued

| | The Diamines | | |
|---|---|---|---|
| 6635-86-5 | *2-amino-3-nitro-4-picoline (2-amino-4-methyl-3-nitro pyridine) | | *2-amino-3-nitro-5-bromo-pyridine |
| 82039-90-5 | *5-amino-4-nitro-imidazole | | *4-amino-5-nitro-6-chlor-pyrimidine |
| | *5-amino-3-methyl-4-nitro-isoxazole | | *2-amino-3-nitro-9-fluorenone |
| | *5-amino-1,3-dimethyl-4-nitro-pyrazole | 7598-26-7 | *2-amino-3-nitro-5-methyl-pyridine |
| 6632-68-4 | *6-amino-1,3-dimethyl-5-nitroso-uracil | | *4-amino-5-nitroso-uracil |
| 22603-53-8 | *2-amino-3,5-dinitro-benzonitrile | 1672-48-6 | *6-amino-5-nitroso-2-thio-uracil |
| 3531-19-9 | *1-amino-2,4-dinitro-6-chlorobenzene | | *2-amino-5-bromo-3-nitro-pyridine |
| 5442-24-0 | *4-amino-2,6-dihydroxy-5-nitro-pyrimidine | 33685-60-8 | †9,10-dinitro-anthracene |
| | *4-amino-2,6-diketo-1,3-dimethyl-5-nitroso-pyrimidine | | *6,7-dinitro-2,3-diphenoxy-quinoxaline |
| | *1,2-dinitro-tetramethyl-benzene | 35975-00-9 | †5-amino-6-nitro-quinoline |
| | *cis-1,2-diamino-1,2-dimethyl-cyclohexane | 771-97-1 | †2,3-diamino-napthalene |
| | *cis-1,2-diamino-1,2-dimethyl-cyclopentane | 938-25-0 | †1,2-diamino-napthalene |
| 36023-58-2 | †5,6-diamino-2,3-dicyano-pyrazine | 39070-63-8 | *3,4-diamino-benzophenone |
| 5440-00-6 | *5,6-diamino-1,3-dimethyl-uracil | 68836-13-5 | †6,7-dinitro-quinoxaline |
| | *5,6-diamino-3-methyl-uracil | | *5,6-dinitro-quinoxaline-2,3-dione |
| 1758-68-5 | †1,2-diaminoanthraquinone | 2379-57-9 | *6,7-dinitro-quinoxaline-2,3-dione |
| 6968-22-5 | *3-amino-4-nitro-benzoic acid | 52057-97-3 | *3,4-diamino-5-hydroxy-pyrazole sulfate |
| 13754-19-3 | †4,5-diamino-pyrimidine | 1672-50-0 | *4,5-diamino-6-hydroxy-pyrimidine |
| 3240-72-0 | *4,5-diamino-uracil (5,6-diamino-uracil) | | |

| | Derivatives of n,n + 2 Diamines (6aa) | | |
|---|---|---|---|
| Registry # | n,n + 2-diamines | Registry # | n,n + 2-diamines |
| | *2-amino-2-(2-aminophenyl)-propane | | †2,4-diamino-2,4-dimethyl-pentane-3-one |
| | *1,3-diamino-1,3-dimethylcyclohexane | | *2,4-diamino-2,4-dimethyl-pentane |
| 479-27-6 | †1,8-diaminonapthalene | | |

The list of n, n+2-Diamines is significantly shorter than the lists for the other derivatives, in large part because the syntheses of the required n, n+2 diamines are more complex than those for the n, n+1 diamines.

Some specific examples of bridge, arm and linker starting materials are shown in Table 7. In each case the amide bonds have been retrosynthetically decomposed to form an amine equivalent (amine, nitro, azide, isocyanate, etc. see Table 1) and a carboxylic, sulfonic, sulfinic, phosphonic, or phosphinic acid equivalent (acid, ester, acyl chloride, nitrile etc. see Table 1). The bridges and linkers of Table 7 conserve local two fold symmetry while all of the arms shown in these examples lead to 5-membered chelate rings.

TABLE 7

A

TABLE 7-continued

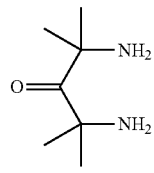

B

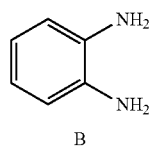

B

TABLE 7-continued

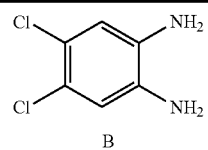
B

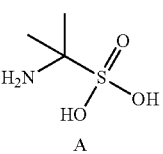
A

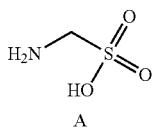
A

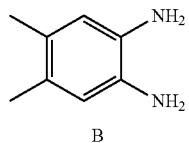
B

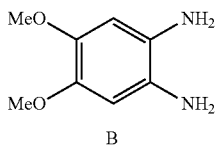
B

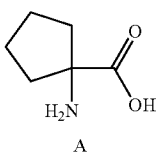
A

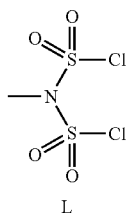
L

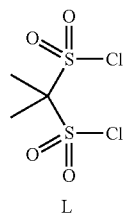
L

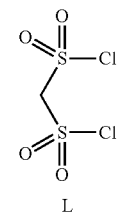
L

Table 7 shows some specific Bridge, B, Arm, A, and Linker, L, starting materials.

The R groups do not participate in the synthesis reaction so numerous variations are possible. However, as discussed in U.S. Pat. No. 5,847,120, to form the oxidatively robust compound and catalyst, there are certain restrictions placed on the $R_1$ and $R_2$ groups. There is considerable evidence that hydrogen atom abstraction occurs between the linker's $R_1$ and $R_2$ substituents and the axial ligand bound to the central metal atom of the ultimate chelate system. This abstraction then is believed to lead to oxidative degradation, as shown in the Collins' Group Patents. To avoid H-atom abstraction and consequent degradation, the R groups of the preferred macrocyclic compounds should be those that will slow down the H-atom abstraction reaction and thereby slow down oxidative degradation. To accomplish this, the $R_1$ and $R_2$ groups of the compound of the present invention are those that have a good bond strength or which are not accessible to the axial ligand, such as those which are too small to reach the axial ligand (hydrogen or deuterium, for example, which may be labile to acid dissociation) or are groups which are sterically or conformationally hindered. Any one or combination of these attributes may be employed. As used herein, good C—H bond strength means more than 94 Kcal·mol$^{-1}$ or more than 85 Kcal·mol$^{-1}$ for sterically inaccessible C—H bonds. C—H bonds are rendered sterically inaccessible by reducing the conformational freedom of the $R_1$ and $R_2$ groups so that they cannot adopt a structure in which they are close enough to the metal bound axial ligand to react. Preferred $R_1$ and $R_2$ groups include hydrogen, deuterium, fluorine, chlorine, methyl, halogen (preferably fluorine or chlorine), $CF_3$ and a spiro-cyclobutyl, spiro-cyclopropyl, spiro-cyclopentyl or spiro-cyclohexyl ring in place of $R_1$ and $R_2$.

There is considerably more freedom in choosing the R substituents for the arm groups than for the linker. In the case of a amino acid arms this may be due to the inability of the five-membered chelate formed by the arm to adopt a conformation in which the oxidatively sensitive C—H bonds approach an axial oxo ligand. In the cases of both α and β amino acid arms this may result from the lack of a second E within the chelate. At any rate, these R substituents of the α and β amino acid can also be chosen to tailor the substituents of the resulting macrocycle to the desired end use. The macrocycle may be symmetrical or asymmetrical. For asymmetrical macrocycles, two different amino acid starting materials are used and the resulting macrocycles are a mixture of symmetrical and asymmetrical versions. The two versions can be separated by known separation techniques. A few examples of the compounds of the present invention are shown below.

TABLE 8

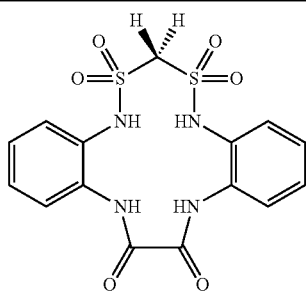

TABLE 8-continued

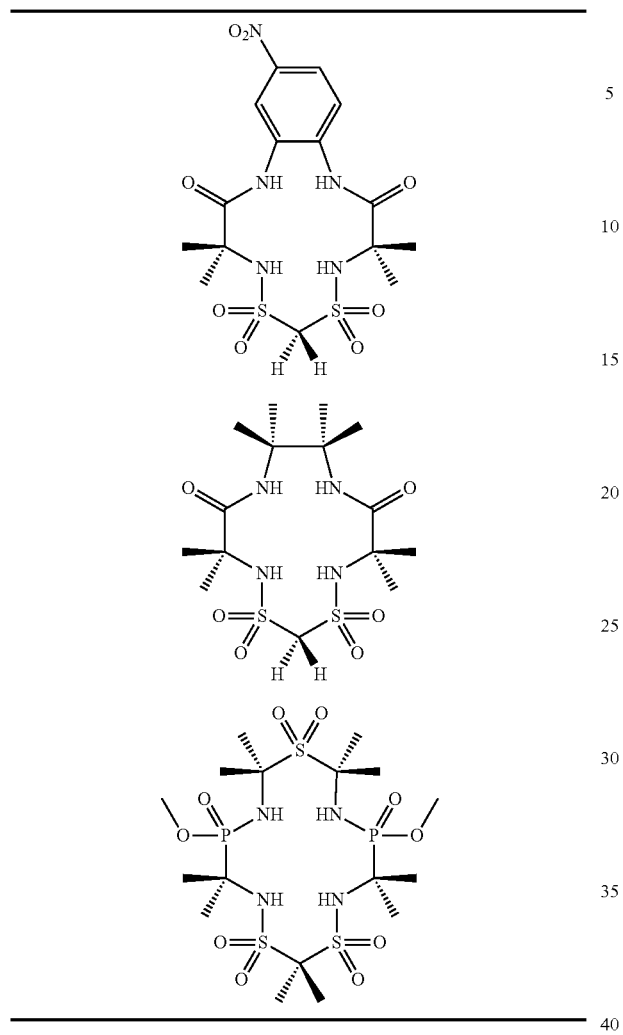

Once the macrocyclic ligand has been prepared, it may be complexed with a wide range of metal ions, preferably a transition metal from groups 3-12 of the Periodic Table of the Elements, and most preferably a group 6, 7, 8, 9, 10 or 11 metal, to form a chelate complex of the formula

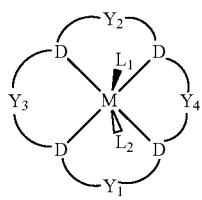

wherein M is the metal, and D is a donor atom, preferably N. $L_1$ and $L_2$ are optional ligands that may be the same or different, neutral or charged, and where at least one of $L_1$ and $L_2$ is labile. $Y_1$, $Y_2$, $Y_3$, and $Y_4$ are oxidation resistant components of the chelate system described above (corresponding to the Y groups of compound 1) which are the same or different and which form five- or six-membered rings with the adjacent DMD atoms.

The R substituents on adjacent carbons of $Y_2$ may be any of the R substituents described herein for comparable positions on Compounds 1 or 2, including, for example, forming a constituent selected from the group consisting of

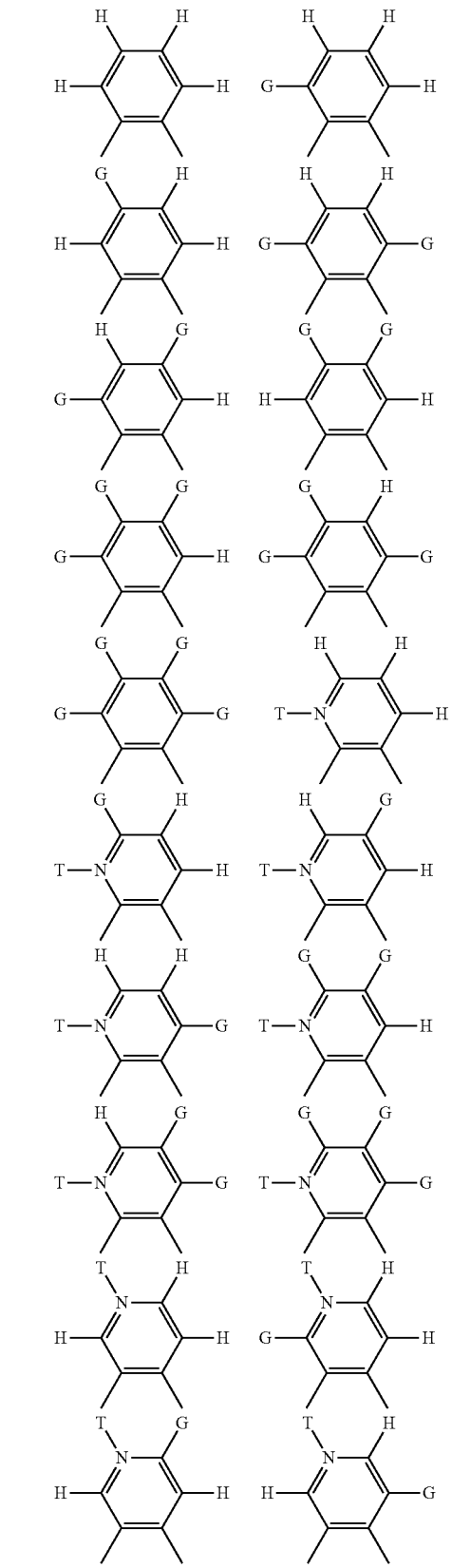

-continued

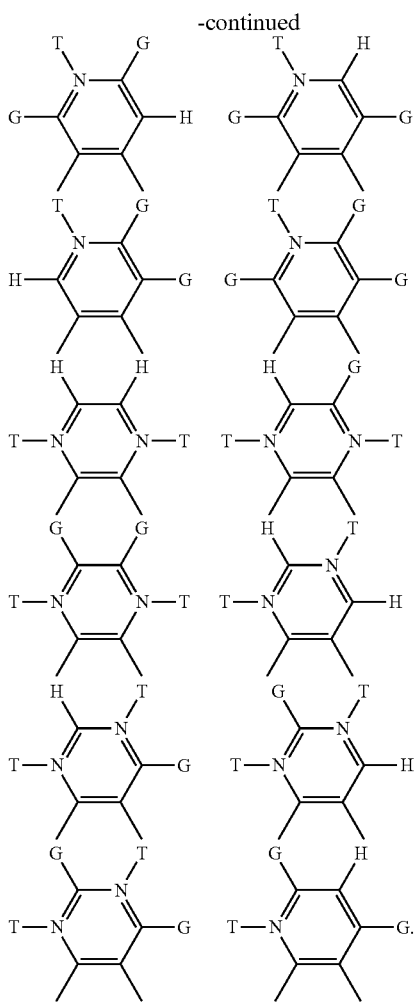

Each T in the foregoing benzene and substituted benzene structures listed for the $Y_2$ aryl group is the same or different and is one of an unoccupied position, or is occupied with one of a hydrogen, alkyl or haloalkyl.

Each G of the aryl group listed for $Y_2$ is the same or different and comprises halogen, hydrogen, alkyl, cycloalkyl, alkenyl, cycloalkenyl, alkynyl, aryl, polycyclic aryl which may contain at least one ring atom that is not carbon, alkylaryl, phenoxy substituents, or amino, substituted amino, amido (—NHCOR, —NRCOR, —NHSO$_2$R, —NRSO$_2$R, —NHPO$_2$R$^-$, —NRPO$_2$R$^-$, —NRPO(OR)R, NRPO(OR)R), fully oxidized or partially oxidized or substituted or unsubstituted carboxylic acid derivatives including, but not limited to, carboxylate (—CO$_2$—), carboxylic acids (—CO$_2$H), esters (—CO$_2$R), amides (—CONH$_2$, —CONHR, —CONR$_2$), and combinations thereof, fully oxidized or partially oxidized substituted or unsubstituted sulfur substituents including, but not limited to, sulfonates (—SO$_3^-$, —SO$_2$(OH), —SO$_2$OR), sulfones (—SO$_2$R), and sulfonamides (—SO$_2$(NH$_2$), —SO$_2$(NHR), —SO$_2$(NR$_2$)), fully oxidized or partially oxidized substituted or unsubstituted phosphorus substituents including, but not limited to, phosphates (—PO$_3^{2-}$, —PO$_2$(OH)$^-$, —PO(OH)$_2$), alkyl phosphate (—PO$_2$(OR)$^-$), phosphonate (—PO(OR)$_2$), phosphinate (—PO(OR)R), phosphine oxide (—P(O)R$_2$), phosphonamides (—PO$_2$(NR$_2$)$^-$, —PO(NR$_2$)$_2$, —PO(OR)(NR$_2$)), phosphines (—PR$_3$), nitrile, nitro, hydroxyl, alkoxy, aryloxy, siloxy, and combinations thereof, or combine to form a cycloalkyl, cycloalkenyl or aromatic ring or rings including polycyclic aromatic systems, which may contain at least one ring atom that is not carbon, (ii) together with one or more G substituents on adjacent carbons, form a mono- or poly-substituted or unsubstituted saturated or unsaturated ring, (iii) joins with an R substituent of one or more G substituents forms a mono- or poly-substituted or unsubstituted saturated or unsaturated ring (iv) together with an R' substituent on an adjacent Z in an adjacent Y unit, form a mono- or poly-substituted or unsubstituted saturated or unsaturated ring, (v) joins together with a substituent on an adjacent E in an adjacent Y unit, form a mono- or poly-substituted or unsubstituted saturated or unsaturated ring.

Complexation is achieved in a similar manner as taught in the Collins' Group Patents, as follows. The macrocyclic ligand is dissolved in a supporting solvent, usually THF, and deprotonated by treatment with a base, preferably lithium bis-trimethylsilylamide, lithium di-isopropyl amide, t-butyl lithium, n-butyl lithium, phenyl lithium, or alkoxides. Any base that removes the protons at the metal complexing site, e.g., the amide N—H protons of an amide containing compound, will suffice. Noncoordinating organic soluble bases are preferred. After the ligand is deprotonated, a metal ion is added. The resulting intermediate, a comparatively low valent ligand metal species, can then be oxidized. The oxidation step is preferably performed with air, chlorine, bromine, or benzoyl peroxide to produce the metal chelate complex usually as a lithium salt. In some cases, including that of copper, metal insertion is known to occur without the use of base. Metathesis of the resulting complex to form a tetraalkyl ammonium, tetraphenyl phosphonium, or bis(triphenylphosphoranylidene) ammonium (PPN) salt tends to yield metal chelate complexes that are easier to purify than the lithium ion containing complexes. The purified or unpurified metal chelate complex can then be used to catalyze oxidation reactions.

If the complex is then combined with a strong O-atom transfer oxidant, preferably a peroxide, such as hydrogen peroxide, t-butyl hydroperoxide, cumyl hydroperoxide or a peracid, a ligand cation-radical metal IV, ligand neutral metal V or ligand neutral metal VI oxo intermediate is produced. When oxidatively robust substituents have been employed to generate the ligand framework these robust, high oxidation state oxo containing species have sufficient lifetimes for use as reactive intermediates. We have shown that these high valent oxo containing species are the active transfer agents in catalyzing a number of oxidation reactions.

When a low valent metal species is exposed to a peroxide or other [O] containing oxidant the metal attracts and binds the oxygen from the oxidant. Depending on the metal, the bond between the metal and the oxygen will be very strong or may be only strong enough to remove the oxygen from the oxidant for subsequent transfer to another constituent.

If the metal is a metal III ion, the resulting oxo species will in general be a metal V ion. If the metal is a metal IV ion, the resulting oxo species will in general contain a metal VI ion or a metal V complex with a second oxidation site on the ligand, i.e., a ligand cation-radical. In addition to its stabilizing effect, the ligand also influences the metal properties. Due to a combination of the stabilizing effect of the macrocyclic ligand and the role of the d electron count at the metal center in controlling the degree of bonding to an oxo ligand, early transition metal complexes tend to form oxides that are stable as a result of their very strong oxygen-metal bonds. Middle and later transition metals tend to remove an oxygen atom from the oxidant and form a reactive metal oxo intermediate. In the metal ligand system produced by the new synthetic method, the middle and later transition metals tend to promote the transfer of oxygen. By controlling the metal, the electron density of the macrocycle, the charge on the complex, and the bond strength/bond order to the coordinated oxo ligand, the metal ligand complex can be fine tuned to achieve a complete range of oxygen transfer abilities, from stable oxides to high valent oxidation catalysts.

In the preferred embodiment, at least one of the axial ligands, $L_1$ and $L_2$, must labile because they occupy their positions relative to the metal until the chelate system is introduced into a solution containing an oxidant. The labile ligand(s) will dissociate and will be replaced by a solvent molecule followed by replacement by the oxidant, most generally an O-atom transfer agent, but also any general oxidant that can serve to activate the metal ion to perform catalysis. Preferred labile ligands include, but are not limited to, the $Cl^-$ anion, halide ions in general, $CN^-$, $H_2O$, $OH^-$, ROH, $NH_3$, phosphate or any amine, carboxylate, phenol or phenoxide, pyridine, ether, sulfoxide, ketone, or carbonate. The oxidation site in the metal complexes of aromatic-ring containing macrocycles can be manipulated by the choice of axial ligands as well as by the ring substituents.

Macrocycles with spiro-cyclohexyl substituents prepared in the manner described in the Collins Group Patents may be prepared for the NuRF containing compounds disclosed herein with modifications described herein for substitution with the NuRF sulfonamides or phosphonamides. These spiro-cyclohexyl substituents have been found to render TAML® macrocycles very hydrophobic and, remarkably, soluble in pentane and other light saturated aliphatic solvents. Long chain substituents, such as a dodecyl chain, or phospholipid chain will render the macrocycle soluble in membranes.

The spiro-cyclobutyl, -cyclopropyl, -cyclopentyl and -cyclohexyl derivatives are sterically hindered and would exhibit slower reaction rates than the other preferred substituents, so the normal synthesis of the amide intermediate of the first step of the method of the invention would be altered, as shown in the Collins Group Patents.

EXPERIMENTAL SECTION

Syntheses of Oxidatively Robust Tetradentate Ligand.

Materials. All reagents and solvents (at least ACS reagent grade) were purchased from commercials sources and used as received, or if necessary, purified as described in the literature. Elemental analyses were performed by Midwest Microlabs, LLC. 300 MHz $^1H$ and $^{13}C$ NMR were obtained on a on a Bruker Avance™ 300. 500 MHz $^1H$ and $^{13}C$ NMR were obtained on a Bruker Avance™ 500. All NMR data were acquired and processed via the Bruker NMR Suite Software package including TopSpin 2.1 and TOPSPIN-PLOT or MestReNova v10. UV/vis spectra were obtained on an Agilent Diode Array spectrophotometer (model HP 8453) equipped with a thermostatted cell holder and automatic 8-cell positioner or a Shimadzu 1800 double beam spectrophotometer. Mass spectrometry measurements were made on a Thermo-Fisher LCQ ESI/APCI Ion Trap.

Syntheses of Macrocyclic Tetradentate-Donor Ligands

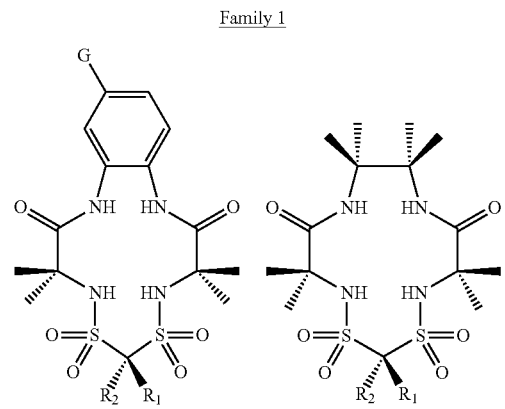

Family 1

To prepare Family 1 type ligands, the amine groups of the Arms are protected with phthalic anhydride. The acid functionality of the Arms is converted to an acid chloride and coupled to a functionalized Bridge. The protecting groups are removed to yield a diamide diamine Macro Linker Intermediate A-B-A. This intermediate is cyclized in the presence of a diacid chloride Linker.

Family 2

To prepare Family 2 type ligands, one amine group on functionalized a Bridge is protected with BOC. The free amines of two protected Bridge molecules are coupled with a diacid chloride Linker. The BOC group is removed with acid to yield a diamine Macro Linker Intermediate B-L-B. This intermediate is cyclized in the presence of a second diacid chloride Linker, the same or different.

Syntheses of Diamines not Readily Available Commercially

Example 1

A. 1,2-Diamino-4,5-Dimethoxy Benzene from 1,2-Dimethoxy Benzene (veratrole)

1,2-Dinitro-4,5-Dimethoxy Benzene: Veratrole was doubly nitrated according to the procedure of Drake et al, in "Synthetic Antimalarials. Some Derivatives of 8-Aminoquinoline", J. Amer. Chem. Soc., 1536, Vol. 68 (1946). Nitric acid (68.3 g, conc.) was added (dropwise, 1 h) to a well stirred solution of veratrole (48.3 g, 350 mmol, d=1.084) in glacial acetic acid (1450 mL) initially cooled to 15° C. The mixture needs to be held below 40° C. but above 10° C. by cooling and proper regulation of the rate of addition of the acid. Considerable mononitroveratrole separated out. Stirring was continued and additional nitric acid (212.7 mL, fuming) was added (dropwise, 1 h) while the temperature of the solution was held below 30° C. As the second nitration proceeded the mono nitroveratrole dissolved and when all the acid had been added, the solution was clear. The nitration mixture was allowed to stand for two hours and was then poured into ca. 1.5 L of ice/cold water. The precipitated dinitro compound was filtered, washed copiously with water until free from acid (pH>5), and recrystallized directly from a minimum of hot EtOH (600 mL). The yield of 1,2-Dimethoxy-4,5-dinitrobenzene was 69.0 g (87%). Characterization: m.p. 129.5-130.5° C. $^1$H NMR (CDCl$_3$) d [ppm]: 7.35 (s, 2H, ArH), 4.02 (s, 6H, OCH3). IR nujol n[cm$^{-1}$]: 3124 (s, w, Aryl CH), 3073 (s, w, Aryl CH), 1592 (s, str, Aryl ring stretch), 1535 & 1518 (s, str, ArNO$_2$). Anal. Calcd. For C$_8$H$_8$N$_2$O$_6$: C, 42.11; H, 3.53; N, 12.28. Found: C, 42.12; H, 3.54; N, 12.33.

1,2-Diamino-4,5-Dimethoxy Benzene: 1,2-Dimethoxy-4,5-dinitrobenzene (10 g, 43.8 mmol) was reduced to 1,2-Dimethoxy-4,5-diamino benzene in acidic MeOH (175 mL+2 eq. of mineral acid, (i.e., 10 mL of conc. HBr)) by catalytic hydrogenation using 10% Pd/C catalyst (24-36 h, 20-22 psi of H$_2$ was consumed from the reservoir). If more than 2 eq. of HBr are added initially the Pd/C catalyst is found to be strongly inhibited. After hydrogenation was complete an additional 4-5 eq. of conc. mineral acid was added to protect the material from oxidation by air and the mixture rotary evaporated to yield a red/purple oil. The crude material was purified by adding a small volume of Abs. EtOH, then pouring the slurry into a 600 mL volume of ice cold Et$_2$O, with storage in the freezer overnight. The red-purple product was collected by filtration, air dried briefly then stored in a desiccator to complete the drying process. Prolonged exposure of the diamine salt to air/water causes a green color to develop which appears to be indicative of irreversible oxidation. Hydrogenation yield was >>90%. Characterization of the red-purple 1,2-Dimethoxy-4,5-Diaminobenzene (dihydrobromide salt hydrate). $^1$H NMR (d$_5$ pyridine) d [ppm]: 10.35 (s, br, 7.5H, H$_2$O/py.HBr/R—NH$_2$ rapidly exchanging), 7.35 (s, 2H, ArH), 3.60 (s, 6H, ArOCH$_3$). IR (nujol/NaCl) n [cm$^{-1}$]: 3085 (br, OH), 2557 (s, str, ArNH$_3^+$), 1623 (s, w, asymmetric NH$_3^+$ bend/Aryl ring stretch), 1539, 1519 (s, m. symmetric NH$_3^+$ bend). (Anal. Calcd. for C$_8$H$_{12}$N$_2$O$_2$) (HBr)$_2$ (H$_2$O)$_{0.66}$: C, 28.09; H, 4.52; N, 8.19. Found: C, 27.82; H, 4.18; N, 8.37. Independent confirmation of hydration was obtained from IR and NMR spectroscopy.

Preparation of the anhydrous sulfate salt of 1,2-Diamino-4,5-Dimethoxy Benzene has been reported by Nakamura, M. et al. in "Fluorimetric Determination of Aromatic Aldehydes with 4,5-Dimethoxy-1,2-Diaminobenzene" Anal. Chim. Acta. (1982), 134, p. 39-45 as follows: 1,2-Diamino-4,5-Dimethoxybenzene (2 g) was dissolved in EtOH (20 mL) and mixed with H$_2$SO$_4$ (conc., ca. 2 mL). The product was recrystallized from EtOH to almost colorless needles (yield ca. 2 g). Anal. Calcd for C$_8$H$_{14}$O$_6$N$_2$S: C, 36.1; H, 5.3; N, 10.5. Found: C, 35.85; H, 5.6; N, 10.4.

B. 1,2-Diamino-4-acetamidobenzene from 1,4-diamino-2-nitrobenzene (2-Nitro-1,4-phenylenediamine)+

1-Amino-2-nitro-4-acetamidobenzene: 1,4-diamino-2-nitrobenzene (2-nitro-1,4-phenylenediamine) was selectively acetylated according to the method of McFarlane et al., J. Chem. Soc. Perkin Trans., 691 (1988) incorporated herein by reference. The amine meta to the nitro group is readily acetylated using acetic anhydride in acetone (the amine ortho to the nitro group is strongly deactivated). The yield of 1-Amino-2-nitro-4-acetamidobenzene (2-nitro-4-acetamido aniline) was >90%. Characterization: $^1$H NMR (CD$_3$OD) d [ppm]: 8.3 (m, 1H, ArH), 7.5 (M, 1H, ArH), 6.9 (M, 1H, ArH), 2.1 (s, 3H, acetyl CH3) in good agreement with McFarlane. IR (nujol/NaCl) n [cm$^{-1}$]: 3470 (s, str, HOAc), 3340-3150 (m, m/str, acetamide ArNH ArNH+ArNH$_2$), 1661 (s, str, acetamide CO), 1643 (s, str, H bonded acetamide CO), 1592 (s, m/w, aryl stretch), 1547 (s, str, ArNO$_2$) & 1512 (s, m ArNO$_2$). Anal. (Dried at 80° C.) Calcd for C$_8$H$_9$N$_3$O$_3$: C, 49.23; H, 4.65; N, 21.53. Found: C, 49.36; H, 4.55; N, 21.31.

1,2-Diamino-4-acetamidobenzene: 1-Amino-2-nitro-4-acetamidobenzene was reduced to 1,2-Diamino-4-acetamidobenzene in acetic acid (HOAc)/MeOH using catalytic hydrogenation over a 10% Pd/C catalyst. The material was isolated as the dihydrochloride salt. Yield>90%. Characterization: $^1$H NMR (CD$_3$OD) d [ppm]: 6.94 (m, 1H, ArH), 6.68 (m, 1H, ArH), 6.62 (m, 1H, ArH), 2.1 (s, 3H, acetyl CH$_3$). IR (nujol/NaCl) n [cm$^{-1}$]: 3348 (s, str, acetamide ArNH), 3226-3100 (m, m, ArNH$_2$), 2588 (s, br, str, ArNH$_3^+$), 1649 (s, str, acetamide CO), 1623 (s, str, H bonded acetamide CO). Anal. (Dried at 80° C.) Calcd for C$_8$H$_{13}$N$_3$OCl$_2$. (HCl/H$_2$O)$_{0.1}$: C, 39.45; H, 5.50; N, 17.25; Cl, 30.57. Found: C, 39.39; H, 5.53; N, 17.32; Cl, 30.37. Presence of solvate HCl/H$_2$O was confirmed by IR, and is consistent with the constant boiling 36.5-38% HCl used to generate the hydrochloride salt.

C. 2,4-Diamino-2,4-Dimethyl Pentanone from 2,4-dimethylpentanone 2,4-Dibromo-2,4-dimethylpentanone To 2,4-dimethylpentanone (85 mL, 68.5 g, 0.60 mol) in CCl$_4$ or 1,2-Dichloroethane (1 L) was added N-bromosuccinimide (NBS, 240 g, 1.35 mol, 2.26 equiv). The mixture was heated under reflux, and benzoyl peroxide (ca 20 mg) was added to the refluxing mixture. While the solution was heated under reflux (24 h), a pale orange solid (succinimide) floated to the surface of the halogenated solvent, while unreacted NBS remained at the bottom. Benzoyl peroxide was repeatedly added to the refluxing mixture (ca 20 mg; 12-24 hr intervals) until no NBS was visible, usually the reaction was complete after 24 hours. When the reaction was complete, the solids were collected by filtration and discarded, the halogenated solvent/Br$_2$ was removed from the mother liquor under reduced pressure, leaving a pale yellow oil. To remove residual halogenated solvent, 95% EtOH (100 mL) was added, solvents were again removed under reduced pressure, and a yellow slightly impure oil resulted (159.99 g, 0.59 mol, 98%). $^1$H NMR (CDCl$_3$): 2.1 (s). IR (neat/NaCl) n [cm$^{-1}$]: 3375 (s, w, impurity OH), 3014, 2978, 2933 (s, str, CH), 2858 (s, w, CH), 1701 (s, str, ketone CO).

2,4-Diazido-2,4-dimethylpentanone: A solution of 2,4-Dibromo-2,4-dimethylpentanone prepared as above or purchased from Lancaster Synthesis (89.8 g, 0.33 mol) in EtOH (1.2 L, 95%) was added to a solution of NaN$_3$ (Caution!, 47.2 g, 0.726 mol, 2.2 equiv) in water (0.6 L). The solution was heated under reflux (16 h) to give a pale orange solution. The EtOH was removed under reduced pressure until the solution became cloudy. The cloudy aqueous solution was extracted, still warm, with pentane (500 mL) three times, and the combined extracts were dried over Na$_2$SO$_4$ and concentrated to 300 mL under reduced pressure. Glacial acetic acid (100 mL) was then added, and the remaining pentane was removed under reduced pressure. This workup was required to remove any excess NaN, since the product is exposed to Pd/C in the next step, and care should be taken to avoid the formation of heavy metal azides (due to the risk of explosion). The solvent was removed from a small sample under reduced pressure to give a neat oil (<20 mg) for spectroscopic characterization: $^1$H NMR (CDCl$_3$): 1.54 (s). IR (neat) n [cm$^{-1}$]: 2115 (RN$_3$), 1720 (ketone CO). It should be noted, for safety, that the organic azides produced in this and related azide based syntheses are never isolated in concentrated forms or as solids in quantities greater than 20 mg.

2,4-Diamino-2,4-dimethylpentan-3-one: Glacial acetic acid (50 mL) was added to the HOAc solution of the dialkyl azide formed in the previous step, and this solution was added to 10% Pd/C (2.7 g). The mixture was hydrogenated at 50 psi (1 week) in a Parr hydrogenator. Because the reaction evolves one N$_2$ molecule for every H$_2$ molecule absorbed, the bomb was evacuated and repressurized 10 times with H$_2$ to 50 psi. (H$_2$ from the high pressure reservoir is not efficiently consumed.) The charcoal was removed by filtration, and HOAc was removed under reduced pressure. After HBr was added (48%, 76 mL), the mixture was dissolved in EtOH. The volatiles were removed under reduced pressure to yield a tan solid, which was washed with a mixture (200 mL) of THF (50%), EtOH (45%), and conc. HBr (5%) or with a mixture of THF (95%) and conc. HBr (5%). The resulting white powdery product was the dihydrobromide salt of 2,4-Diamino-2,4-dimethylpentan-3-one (56.2 g, 48% from 2,4-Dibromo-2,4-dimethylpentanone). Additional product may be collected from washings that have been pooled from several different preparations. The product must be stored as the dihydrobromide or dihydrochloride salt to protect the amines from oxidative degradation. Characterization: $^1$H NMR (CDCl$_3$/DMSO-d$^6$) of 2,4-diamino-2,4-dimethyl-pentan-3-one. 2 HBr: 8.62 (6H, s, br, NH$_3$), 1.77 (12H, s, Me). IR (free base, nujol mull) n [cm$^{-1}$]: 3460-3160 (RNH$_2$), 1690 (ketone CO). Anal. (Dried at 80° C.) Calcd for C$_7$H$_{16}$N$_2$O. (HBr)$_2$: C, 27.47; H, 5.93; N, 9.15; Br, 52.22. Found: C, 27.43; H, 5.91; N, 9.11; Br, 52.46.

D. 2,3-Diamino-2,3-dimethylbutane dihydrochloride from 2,3-Dimethyl-2,3-dinitrobutane 2,3-Diamino-2,3-dimethylbutane dihydrochloride was prepared according to the procedure in Sayre, R. in "The Identity of Heilpern's "Pinacolylthiourea" and the Preparation of Authentic 2-Thiono-4,4,5,5-tetramethylimidazolidine" *J. Am. Chem. Soc.* 1955, 77, 6689. 2,3-Dimethyl-2,3-dinitrobutane (6 g, 34 mmol) was suspended in 100 mL concentrated HCl and the mixture was gently warmed to 50° C. Granulated tin (68.2 g, 0.575 mol) was added in ca. 5 g batches at 10 min intervals, the mixture was refluxed for 2 h, cooled on ice, and KOH (16 M, 50 mL) was added dropwise via addition funnel to give a gray precipitate. The suspension was filtered through a bed of sand and Celite. The filtrate was distilled at atmospheric pressure until the distillate was no longer basic. The distillate was acidified to pH 2 with concentrated HCl. The remaining water was removed under vacuum to yield 3.91 g of a white solid (61%). $^1$H NMR (D$_2$O): 1.55 (s, 6H). ESI-MS: 117.1 (M+H, H$_2$O, positive mode).

Example 2

Macro Linker Intermediate (A-B-A) Synthesis, from 2-Aminoisobutyric Acid and o-Phenylenediamine i. Synthesis of 2-Methyl-2-phthalimidopropanoic acid 2-aminoisobutyric acid (25 g, 0.24 mol, 1 eq) and phthalic anhydride (58 g, 0.39 mol, 1.6 eq) were melted in a 500 ml round bottomed flask at 190° C. The compounds were mixed thoroughly with a glass rod before melting. The melt gradually turned clear with bubbles of water (side product). The reaction was assumed complete when the water bubbles ceased to form. The reaction was continued at the same temperature for 20 min longer then poured slowly into a saturated sodium bicarbonate solution (~1.5 L). The solution was filtered through a glass frit containing celite. The filtrate was cooled in an ice bath and acidified to pH 2 with concentrated HCl. The product precipitated and was isolated by filtration of the solution through a glass frit and dried under vacuum at 60° C. overnight. Yield: 83%; $^1$H NMR (d$_6$-DMSO) 12.92 (s, 1H), 7.85 (s, 4H), 1.73 (s, 6H)

ii. Synthesis of N,N'-(1,2-Phenylene)bis(2-(1,3-dioxoisoindolin-2-yl)-2-methylpropanamide)

Crude o-Phenylenediamine was dissolved in hot aqueous 1% NaHSO$_3$ with activated carbon. Upon dissolution the solution was filtered while still hot through a glass frit protected with celite. More pure o-Phenylenediamine crystallized from the filtrate upon cooling and was isolated by filtration on a glass frit. This procedure was repeated until the crystals so obtained were off white (from dark brown). Dry acetonitrile (5 mL) and SOCl$_2$ (0.33 ml) were added under Ar to a 3-neck round bottom containing 2-methyl-2-phthalimidopropanoic acid (1 g) fitted with a condenser and thermometer. The mixture was stirred at 50° C. for 90 min then cooled to 5-10° C. A solution of o-phenylenediamine (0.25 g), Et$_3$N (1.4 mL), and acetonitrile (2 ml) was added dropwise while maintaining the temperature under 20° C. Upon completion of the addition, the reaction mixture was heated to 45° C. for 90 min. Water (7 ml) was added and the mixture was stirred at room temperature for 30 min. Heptane (15 mL) was added and the mixture was stirred for 30 min. The precipitate was collected by vacuum filtration, rinsed with water and heptane, and was dried under vacuum at 50° C. Yield: 80 mg (69%). $^1$H NMR (300 MHz, CDCl$_3$) δ 8.10 (s, 2H, NH), 7.79-7.62 (m, 8H, C$_2$C$_6$H$_4$), 7.56 (m, 2H, N$_2$C$_6$H$_4$), 7.21 (m, 2H, N$_2$C$_6$H$_4$), 1.90 (s, 12H, CH$_3$).

iii. Synthesis of N,N'-(1,2-phenylene)bis(2-amino-2-methylpropanamide)

Dry N,N'-(1,2-Phenylene)bis(2-(1,3-dioxoisoindolin-2-yl)-2-methylpropanamide) (2.0 g, 3.6 mmol, dry) and absolute EtOH (40 mL) were combined in a round bottom flask fitted with a condenser. The reaction mixture was heated near to reflux then 0.34 mL of 64% hydrazine hydrate was added (POISON). The reaction mixture was heated to reflux for 6-12 hours during which the heterogeneous mixture became homogeneous followed by precipitation of a white solid. The reaction mixture was cooled to room temperature and the solvent was removed under reduced pressure to give a solid. HCl (125 mL, 2M) was added to the solid, and the suspension was heated to 80° C. for 10 min then cooled to room temperature and filtered. Concentrated NaOH was added dropwise to the filtrate until the pH was 12-13. The solution turned yellow and was extracted with dichloromethane (4×30 mL) and ethyl acetate (30 mL). The dichloromethane phases were combined; dried with $MgSO_4$, filtered, and evaporated to dryness on a rotary evaporator. The ethyl acetate phase was dried with $Na_2SO_4$, filtered, added to the solids from the dichloromethane layers and evaporated to dryness. The resulting solid was slurried in diethyl ether, isolated by filtration, and dried under vacuum at 50° C. Yield: 0.546 g (58%). NMR (300 MHz, DMSO) δ 7.60 (m, 2H, Ar), 7.15 (m, 2H, Ar), 4.71 (s, 6H, NH), 1.31 (s, 12H, $CH_3$).

Example 3

Macro Linker Intermediate (B-L-B) Synthesis, from methanesulfonic acid dichloride and o-Phenylenediamine i. Synthesis of tert-butyl (2-aminophenyl)carbamate

Recrystallized o-phenylenediamine (3.0 g, 27.8 mmol) and triethylamine (3.8 mL, 27.8 mmol) were dissolved in 50 mL dry THF in a round bottom flask. In a second flask, di-tert-butyl-dicarbonate (6.0 g, 27.8 mmol) was dissolved in 50 mL dry THF. The solutions were added dropwise simultaneously with a syringe pump to a third flask containing 60 mL dry THF at 0° C. and allowed to warm to room temperature and stir overnight. The solvent was removed from the clear solution under reduced pressure to give a brown oil. Diethyl ether (25 mL) was added to the oil and sonicated until homogeneous. The diethyl ether was removed under reduced pressure to give a brownish-pink solid. Recrystallization in hot heptane/ethanol yielded off-white flaky crystals. 1H NMR (300 MHz, $CDCl_3$): 7.30 (1H, m), 7.02 (1H, m), 6.80 (2H, m), 6.24 (br s, 1H), 3.75 (br s, 21H), 1.56 (s, 9H).

ii. Synthesis of di-tert-butyl ((methylenedisulfonyl-bis(azanediyl))bis(2,1-phenylene))dicarbamate To a three neck round bottom flask with a stir bar and dropping funnel under Ar was added tert-butyl (2-aminophenyl)carbamate (1.04 g, 5 mmol), triethylamine (0.7 mL, 5 mmol), and 30 mL of dry THF. An additional 30 mL dry THF and methanedisulfonyl dichloride (0.28 mL, 2.5 mmol) were combined in the dropping funnel and added dropwise to the flask at 0° C. The mixture was allowed to warm to room temperature and stir overnight. The reaction mixture was filtered and concentrated under reduced pressure to give an oil that was sonicated in diethyl ether giving a flaky solid that was used without further purification. 1H NMR (300 MHz, $CDCl_3$): 7.73 (dd, 2H), 7.57 (s, 2H), 7.44 (dd, 2H), 7.33 (m, 2H), 7.18 (s, 2H), 7.13 (m, 2H), 4.40 (s, 2H), 1.55 (s, 18H). ESI-MS: 555.1 m/z (100%), [M−H+]− iii. Synthesis of N,N'-bis(2-aminophenyl)methanedisulfonamide

To a 3-neck round bottom flask under Ar with a stir bar and an addition funnel was added di-tert-butyl ((methylenedisulfonylbis(azanediyl))bis(2,1-phenylene))dicarbarnate (1.77 g, 3.18 mmol) and 20 mL of dry $CH_2Cl_2$. The mixture was cooled to 0° C. and a mixture of 10 mL of trifluoroacetic acid and 20 mL of $CH_2Cl_2$ were added dropwise. The reaction solution was allowed to warm to room temperature and stirred for two hours. The clear solution was concentrated under reduced pressure to give a light brown oil. This oil was diluted with 75 mL of water and a 1 M sodium hydroxide solution was added to bring the pH of to 10. The solution was extracted with $CH_2Cl_2$ (3×20 mL) and the combined organic layers were dried with magnesium sulfate, filtered, and concentrated to yield a white product. $^1H$ NMR (300 MHz, DMSO-d6): 7.00 (in, 4H), 6.75 (m, 4H), 6.55 (m, 2H), 4.70 (s, 2H). ESI-MS: 355.1 m/z (100%), [M−H+]−.

Macrocyclization Reactions

Several synthetic routes for the preparation of macrocyclic tetradentate ligands have been developed. An organic azide based route is described in Uffelman, E. S., Ph.D. Thesis, California Institute of Technology (1992) and Kostka, K. L., Ph.D. Thesis Carnegie Mellon University (1993). Examples of several synthetic routes for the preparation of amide containing macrocycles are described in the Collins Group Patents, incorporated herein by reference. Given below are new methods of macrocyclization of linkers A-B-A and B-L-B with an activated linker.

Example 4

Synthesis of Macrocyclic Sulfonamide Ligand

A. Synthesis of Macrocyclic Hybrid Sulfonamide Ligand with NR-(1,2-phenylene)bis(2-amino-2-methylpropanamide)

A solution of N,N'-(1,2-phenylene)bis(2-amino-2-methylpropanamide) (420 mg, 1 eq), dry $CH_2Cl_2$ (40 mL), and $Et_3N$ (0.21 mL) and a separate solution of diacid dichloride linker (1 eq) and dry $CH_2Cl_2$ (40 mL) are simultaneously added dropwise via syringe pump to $CH_2Cl_2$ (400 mL) at 0° C. under argon with stirring. Upon completion of the additions, the flask is allowed to warm overnight. The reaction mixture is filtered through a fine porosity glass frit and the solvent is partially removed from the filtrate in vacuo. The residue is purified by flash chromatography (silica gel, gradient elution 80/20 EtOAc/heptane increasing to 95/5).

B. Synthesis of Macrocyclic Tetrasulfonamide Ligand with N,N'-bis(2-aminophenyl)methanedisulfonamide To a small flask under Ar is added N,N'-bis(2-aminophenyl)methanedisulfonamide (300 mg, 1 eq), dry THF (40 mL) and dry pyridine (0.27 mL). To a second flask is added diacid dichloride linker (1 eq) and dry THF (40 mL). Both solutions are added dropwise with a syringe pump to a 3-neck flask containing THF (250 mL) at 0° C. The flask is allowed to warm overnight, then filtered. The resulting solid is rinsed with additional THF and purified by column chromatography as in example A or extracted as follows. The solid is taken up into a mixture of ethyl acetate and 0.1 M HCl. The layers are separated and the aqueous layer washed with a second aliquot of ethyl acetate. The organic fractions are combined, dried with sodium sulfate, filtered, and concentrated under reduced pressure to give a powdery solid.

Synthesis of Chelate Complexes

Example 5

Synthesis of lithium and tetraalkylammonium tetrasulfonamide complexes nBuLi (0.2 mL of 1.6 M in hexane) is added to a solution of the parent macrocyclic tetradentate ligand (25 mg) in dry THF (5 mL) in a round bottom flask at 0° C. under Ar with stir. Upon completion of the addition, solid anhydrous $FeCl_3$ (25 mg) is added in one portion. The mixture is stirred at room temperature overnight then opened to air. The solvent is removed and the solids suspended in a minimum amount of water/methanol and filtered through a glass frit to remove brown iron solids. The filtrate is reduced on the rotovap and purified by flash chromatography on C-18 silica gel with 90% water/10% methanol as the eluent.

Because of variable solvation and limited solubility, the lithium salt may be converted to the tetraethylammonium or tetramethylammonium salt for further use. The lithium salt (595 mg) in $CH_3OH$ (50 mL) is loaded onto an ion exchange column (Amberlite IR-120 Hydrogen form) that is presaturated with $[Et_4N]^+$ cations, and the band is eluted with $CH_3OH$ (100 mL). The solvent is removed under reduced pressure. The product can be further purified by a second C-18 column with a minimum amount of methanol in the mobile phase. Concentration of the red fractions under reduced pressure gives a red solid. X-ray quality crystals may be obtained by vapor diffusion of ether into a solution of the complex in acetonitrile.

Some examples of specific applications of various embodiments of the macrocyclic compounds of the present invention are disclosed in the Collins Group Patents. See for example, U.S. Pat. Nos. 5,847,120 and 6,051,704.

Example 6

A method for synthesis of the phosphinamide catalyst, wherein E is P(=Q)R' or PR'$_3$ and Q is oxygen follows.

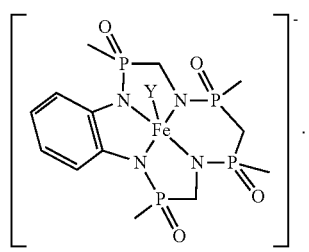

i. Synthesis of Cbz-protected methylene methylphosphinic diamide (1)

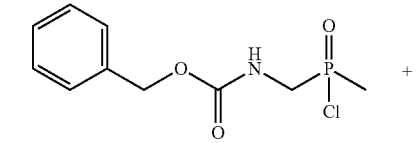

(N-Carbobenzoxyaminomethyl)methylphosphinic chloride

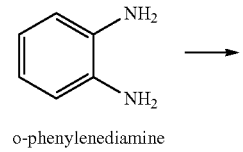

o-phenylenediamine

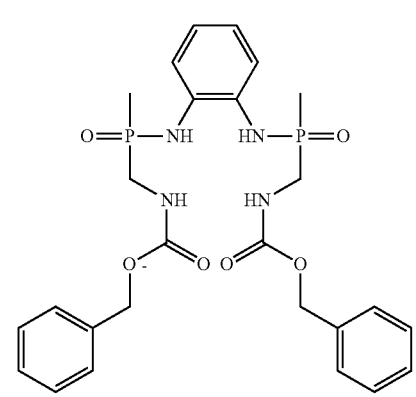

1

(N-Carbobenzoxyaminomethyl)methylphosphinic chloride will be prepared according to the procedure of Moree et al., in "Peptides Containing the Novel Methylphosphinamide Transition-State Isostere" *Tetrahedron* 1993, 49, 11055-11064. A solution of o-phenylenediamine (0.51 mmol) and N-methyl morpholine (0.51 mmol) in $CH_2Cl_2$ (10 mL) will be added dropwise to a solution of N-Carbobenzoxyaminomethy)methylphosphinic chloride (1 mmol) in $CH_2Cl_2$ (10 mL) at 0° C. under Ar with stir. The mixture will be allowed to warm to room temperature overnight with stir, be concentrated on a rotary evaporator, and purified by flash chromatography (15 g silica gel, eluent: $CH_2Cl_2$/MeOH 97/3 (v/v)) to yield 1.

ii. Synthesis of methylene methylphosphinic diamide 2 (N,N'-(1,2-phenylene)bis(P-((α2-azanyl)methyl)-P-methylphosphinic amide))

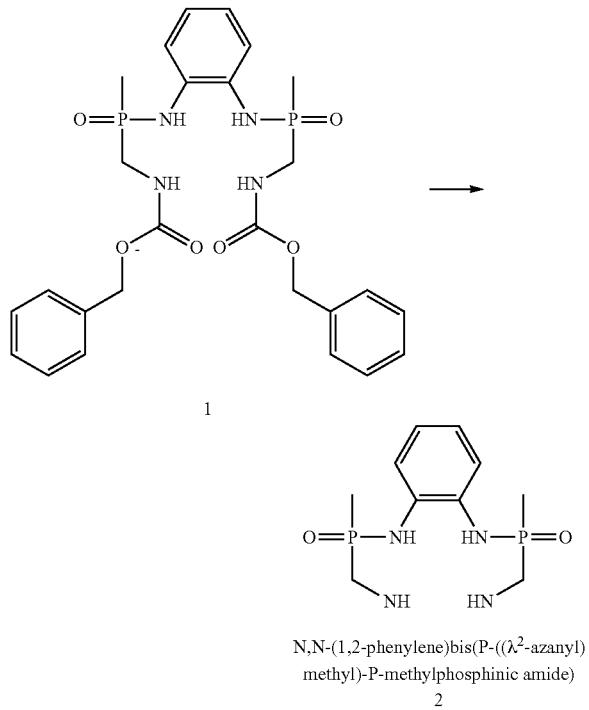

1

N,N-(1,2-phenylene)bis(P-((λ²-azanyl)methyl)-P-methylphosphinic amide)

2

Pd/C (10%) will be added to a solution of protected phosphinamide 1 (0.3 mmol) in CH₃OH (10 mL). The mixture will be stirred under H₂ at room temperature until ³¹P NMR shows complete removal of the carbobenzoxy group (2 h). After filtering the mixture over Hyflo, the solvent will be removed under reduced pressure and the product 2 will be purified by flash chromatography (silica gel, CH₂Cl₂/MeOH 9:1).

iii. Synthesis of phosphinamide macrocycle 3 (2,5,7,10-tetramethyl-1,3,4,6,8,9,11-heptahydrobenzo[1][1,4,8,11]tetraaza[2,5,7,10]tetraphosphacyclotridecine 2,5,7,10-tetraoxide)

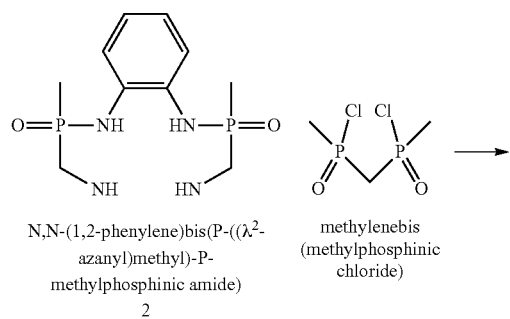

N,N-(1,2-phenylene)bis(P-((λ²-azanyl)methyl)-P-methylphosphinic amide)
2 methylenebis(methylphosphinic chloride)

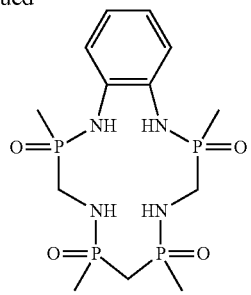

2,5,7,10-tetramethyl-1,3,4,6,8,9,11-heptahydrobenzo[1][1,4,8,11]tetraaza[2,5,7,10]tetraphosphacyclotridecine 2,5,7,10-tetraoxide
3

A solution of phosphinic diamine 2 (0.15 mmol) in dry CH₂Cl₂ (40 mL) with triethylamine (0.21 mL) and a separate solution of methylenebis(methylphosphinic chloride)₂ (0.15 mmol, 1 eq) in dry CH₂Cl₂ (40 mL) will be simultaneously added in dropwise via syringe pump to CH₂Cl₂ (400 mL) at 0° C. under argon with stirring. The flask will be allowed to warm to room temperature overnight then the solution will be filtered. The solvent will be partially removed and the residue purified by column chromatography (silica gel, eluent 80/20 EtOAc/heptane increasing to 95/5).

iv. Synthesis of [Li]4 and [PPh₄]4

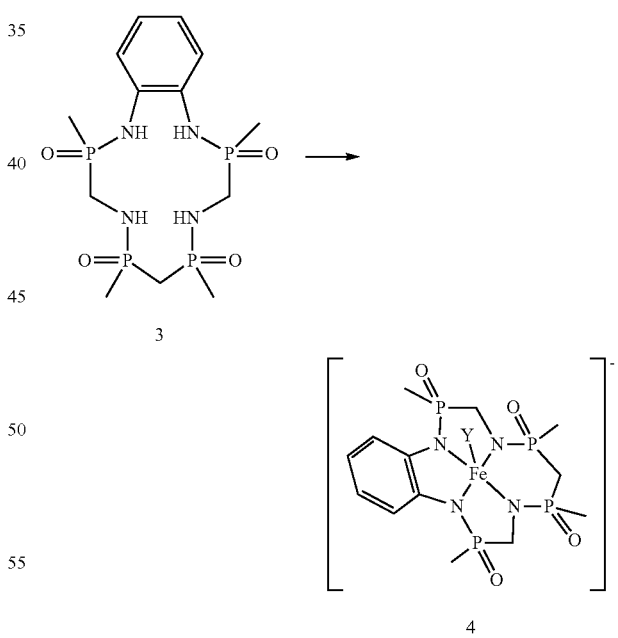

nBuLi (0.64 mL of 1.6 M in hexane, 4 eq) will be added dropwise to a solution of the macrocyclic tetradentate ligand 3 (0.25 mmol) in dry THF (20 mL) in a 3-neck round bottom flask at 0° C. under Ar with stir. Upon completion of this addition, anhydrous FeCl₃ (0.3 mmol, 50 mg) will be added in one portion. The reaction mixture will be stirred at room temperature overnight. The reaction mixture will be purified by column chromatography using basic alumina (1% Et₃N/5%

MeOH/94% CH$_2$Cl$_2$) to yield [Li]4 with Y=H$_2$O and exchanged from [Li] to [NMe$_4$] or [PPh$_4$] following the above general procedures as necessary. See the procedures in Moree, W. J.; Van Der Marel, G. a.; Van Boom, J. H.; Liskamp, R. M. J., "Peptides Containing the Novel Methylphosphinamide Transition-State Isostere," *Tetrahedron* 1993, 49, pp. 11055-11064 and Hietkamp, S.; Sommer, H.; Stelzer, O., "Synthese Und NMR-Spektroskopische Charakterisierung pH-Funktioneller Methylenverbriickter Diphosphane R2P—CH$_2$—PRH Und IMP-CH$_2$—PRH," *Chem. Ber.* 1984, 3413, pp. 3400-3413, incorporated herein by reference.

Applications of High Valent Metal Oxo Species:

Water Splitting

Water splitting is most easily described as the microscopic reverse reaction of hydrogen combustion according to the following schematic.

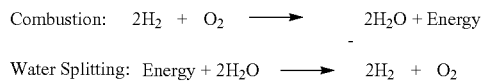

Dioxygen formation occurs in the oxidation half-cell reaction, while hydrogen formation occurs in the reduction half-cell reaction, Scheme 2. Conceptually, H$_2$O can be viewed as being comprised of 2H$^+$ and O$^{2-}$.

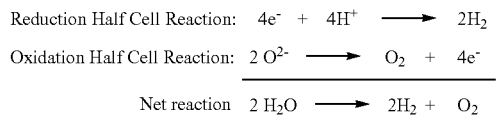

Although it is quite easy to reduce H$^+$ to form H$_2$ by procedures well known to those skilled in the art, it is difficult to oxidize water to form oxygen. This is largely due to the fact that the ions are strongly bound to the O$^{2-}$ ions rendering water oxidation very difficult to perform under neutral or acidic conditions. Under basic conditions the reaction becomes easier due to the greater facility (lower oxidation potential) by which OH$^-$ is oxidized compared to H$_2$O.

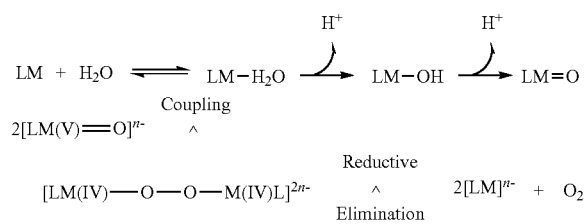

High valent metal oxo species are thermodynamically well situated to catalyze the most difficult part of the water splitting reaction, the formation of dioxygen. Metal ions readily bind water to form aqua species, for example, the aqua species of the metal ligand systems described in the Accounts article. Metal aqua species are more acidic than free H$_2$O losing protons readily to form metal hydroxo and metal oxo species. The preparation of metal oxo species in high oxidation states has been described in the Accounts article. It is believed that high valent metal oxo species can play a pivotal role in water oxidation processes according to the scheme shown above wherein LM is the metalated chelate complex of the present invention.

Solar Cells

The direct application of the catalyst systems described herein to harvest light for solar cells and particularly the indirect application of using light derived energy to perform an oxidation reaction are of profound interest. Recent results have demonstrated that metal aqua complexes of the ligand systems described herein can be oxidized via pure electron transfer reactions to yield high valent metal oxo species. This is significant because one of the big problems in solar cell technology is that of energy storage. Normally, a photovoltaic cell is used to convert solar energy to electrical energy, and then a battery is often used to store the energy in the form of chemical energy. The chemical energy in the battery is then reconverted to electrical energy for power line transmission, and then in many cases the electrical energy is converted back to chemical energy in order to perform useful chemical transformations.

The voltage generated in the first step of solar energy harvesting, the photovoltaic voltage, can be directly applied to the generation of chemical energy. The catalyst systems of the present invention offer a valuable opportunity to harvest electrical energy for the performance of chemical transformations, most notably water splitting. In this scenario, when the sun shines, photovoltaic energy is utilized by the catalyst systems as the driving force for performing the energy intensive part of water splitting, oxygen generation. The hydrogen generation part is not energy intensive and will proceed effectively from H$^+$ using known technology such as the normal hydrogen electrode. Once the chemical transformation is complete, it is believed that the energy from the sun will have been stored in the form of the technologically significant fuel, hydrogen, and the commercially important oxidant, oxygen, thereby eliminating the unnecessary storage of the electrical energy in a battery.

Another important application for the oxidation catalyst system of the present invention is the manufacture of hydrogen. Hydrogen is now manufactured by way of the water gas shift reaction being performed on hydrocarbons such as coal or natural gas. The byproducts of the water gas shift reaction are CO and CO$_2$, green house gases. Hydrogen generated from water can change the balance of the CO$_2$ released into the atmosphere, thereby significantly reducing the effect of green house gases and global warming.

Fuel Cells

Normal hydrogen/oxygen fuel cells extract the chemical energy stored in the hydrogen/oxygen combustion reaction (see Scheme 1 under water splitting, above) and convert it into electricity with a high level of efficiency. The catalyst systems of the present invention are effective utilizers of hydrogen peroxide for oxidation reactions, therefore can be useful in the production of a new type of fuel cell, the hydrogen peroxide/substrate fuel cell. Instead of burning a fuel, hydrogen, in the oxidant, oxygen, and extracting the chemical energy as electricity, this new breed of fuel cell will "burn" the substrate fuel in the oxidant hydrogen peroxide and extract the chemical energy as electricity. This is of commercial significance because of the growing need to supply energy to an energy-starved world without generating toxic waste products during the process of energy production. Normal combustion processes are suitable for the generation of heat which can be utilized for power generation. However, two significant drawbacks of combustion processes are the inefficiency by which heat can be utilized to generate electricity, on the order of 40-45% Carnot efficiency at best, and the generation of volatile toxic byproducts such as NOX, SOX, and AOX which result from the presence of nitrogen, sulfur and halides particularly chlorine in the fuel. A hydrogen peroxide fuel cell solves several of these problems definitively, avoiding NOX production entirely, and allowing for the trapping of SOX and AOX byproducts under controlled low temperature conditions that are absent in normal combustion processes. The hydrogen peroxide fuel cell is also likely to be able to harness energy efficiently at well above the 40-45% typical of combustion processes since the chemical energy is converted directly into electrical energy without the inefficient intermediacy of steam based turbine power generation.

The greatest drawback of a hydrogen peroxide fuel cell is the high cost of hydrogen peroxide relative to air. However, in some niche applications it may be possible to use other energy sources, such as solar energy, to generate the hydrogen peroxide. See the water splitting, and solar energy sections.

Liquid $CO_2$ Oxidations

As greater emphasis is placed on environmentally sound manufacturing processes, the use of environmentally non-toxic solvent systems such as supercritical (SC) $CO_2$ has become an economically important facet of the chemical industry. Recent advances in SC $CO_2$ technology have focused on the solubilization of metal containing catalyst species by the addition of perfluorinated solubilizing groups. In the absence of such perfluorinated tails, most metal catalyst systems are completely insoluble in SC $CO_2$. The metal catalyst systems of the invention perform a large variety of useful oxidations and are synthetically versatile enough to easily support the introduction of perfluorinated tails. These perfluorinated catalyst systems will provide an easy entre into the use of SC $CO_2$ as an oxidatively robust and environmentally sound solvent system for performing commercially significant oxidations.

Wastewater Clean-Up

An EPA report outlining environmental issues in the textile industry, EPA/310-R-97-009, described the wastewater streams from textile mills as being comprised of a complex mixture of different species including sizing, salts, colorants (dyes and dye chromophores), chemicals with high biological oxygen demand (BOD), acids, alkalis, and a variety of organic compounds. While dyes do not comprise a large percentage of the total waste stream, the colors that they impose if allowed to enter streams and lakes may be unacceptable, Zollinger, H., *Color Chemistry, VCH Publishers, Germany,* 1987. It is estimated that 10-15% of the 700,000 tons of dyes produced annually worldwide are released in waste streams, Snowden-Swan, L. J., *Industrial Pollution Prevention Handbook,* Freeman, H. M., Ed., McGraw-Hill, New York, 1995. Among the different technologies applied to decolorizing waste streams are adsorption of the dye onto a substrate such as charcoal followed by filtration (this is an expensive process) and oxidative degradation. Oxidative degradation processes have relied principally on chlorine and ozone as the oxidants. It is known that oxidation of organic compounds by chlorine can lead to polychlorinated aromatics which are environmental hazards. The cost of ozone is extremely high making it impractical in the long-term. The most environmentally desirable oxidant is hydrogen peroxide, $H_2O_2$, as its decomposition products are oxygen and water. It has also been noted that desizing starch with $H_2O_2$ rather than enzymes would be economically viable. The compounds described herein are excellent and efficient activators of $H_2O_2$ for a variety of oxidation reactions, particularly where a robust catalytic system is needed, and may be used effectively in the bleaching of a variety of dyes.

Further examples include the disinfection of food surfaces and water, swimming pools and spas, surface cleaning, e.g., metals, stone, glass, electronics, plastic and polymeric surfaces, surface preparation for painting to enhance adhesion and bleaching, e.g., hair, textiles and pulp and paper bleaching and delignification applications. The effluent from pulp mills can be oxidized for decolorization as well, as described in U.S. Pat. No. 6,136,223 and incorporated herein by reference. Other oxidation reactions that can be activated by the compounds of the present invention include oxidative detoxification, e.g., nerve gas, and homogenous chemical oxidations in general. Of particular interest is the use of the compounds to activate peroxide or other oxidants for disinfection, sterilization, for wound cleaning, as fungicides, as bactericides, as insecticides and as herbicides, in sewage treatment, in water treatment, and remediation. The compounds can also be used in oxidant interconversions.

The invention claimed is:

1. A complex of the formula:

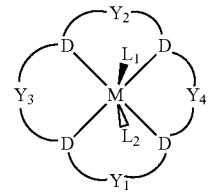

wherein:

M is a metal;

D is Nitrogen;

each of $Y_1$, $Y_2$, $Y_3$ and $Y_4$ individually form a 5-membered or 6-membered ring with the metal and two adjacent Ds, and each of $Y_1$, $Y_2$, $Y_3$ and $Y_4$ individually is selected from the group consisting of:

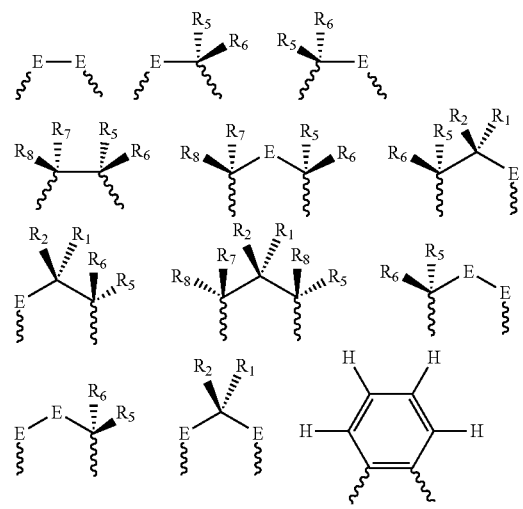

-continued

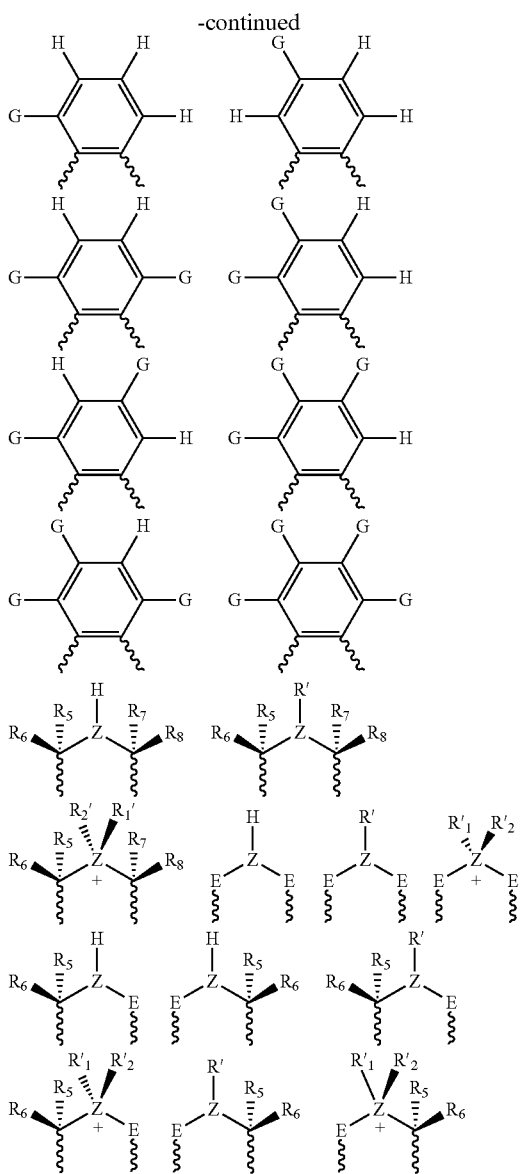

wherein
| indicates a bond to one D;
each E individually comprises a group of atoms comprising an in-ring atom forming a portion of a respective 5-membered or 6-membered ring, the in-ring atom selected from the group consisting of sulfur, phosphorous, and carbon;
at least one E in $Y_1$, $Y_2$, $Y_3$, $Y_4$, or a combination thereof is more resistant to nucleophilic attack than C=O and C=NR', wherein the at least one E that is more resistant to nucleophilic attack than C=O and C=NR' comprises an in-ring atom that is either sulfur or phosphorous and the at least one E that is more resistant to nucleophilic attack than C=O and C=NR' is directly attached to one D;
when the in-ring atom of E is sulfur, E is selected from the group consisting of $S(=O)_2$, $S(=O)R'_2$, $S(=O)$, $S(=NR')_2$, $S(=NR')R'_2$, and $S(=NR')$;
when the in-ring atom of E is phosphorous, E is selected from the group consisting of $P(=NR')R'$, $P(=O)R'$, and $P(R')_3$;
when the in-ring atom of E is carbon, E is selected from the group consisting of C=O and C=NR';
each Z is individually selected from the group consisting of oxygen, sulfur, nitrogen, phosphorous, and arsenic;
each of R', $R'_1$, and $R'_2$ is individually selected from the group consisting of hydrogen, deuterium, oxygen, a hydroxyl, a halogen, a nitrogen-containing group, a carbon-containing group, lithium, sodium, potassium, and combinations thereof;
each of $R_1$ and $R_2$ is independently selected from the group consisting of hydrogen, deuterium, alkyl, aryl, $CF_3$, halogen, perhaloalkyl, and combination thereof;
each of $R_5$, $R_6$, $R_7$, and $R_8$ is independently selected from the group consisting of hydrogen, deuterium, an alkyl, an alkenyl, an alkynyl, an aryl, an alkoxy, a phenoxy, an oxylic, a phenyl, a halogen, a halogenated alkyl, a perhaloalkyl, a halogenated aryl, a perhaloaryl, a halogenated alkenyl, a halogenated alkynyl, an alkylaryl, $CF_3$, $CH_2CF_3$, a cycloalkyl ring, a cycloalkenyl ring, a heterocyclic ring, a carboxyl, a fully oxidized or partially oxidized carboxylic acid derivative, a sulfur substituent, a fully oxidized or partially oxidized phosphorus substituent, and combinations thereof;
each G individually comprises a substituent selected from the group consisting of a halogen, a hydrogen, a fully oxidized or partially oxidized sulfur substituent, a fully oxidized or partially oxidized phosphorus substituent, an amino, an amido, a methyl, a haloalkyl, a nitrile, a nitro, a carboxylate, and combinations thereof; and
$L_1$ and $L_2$ are optional ligands.

2. The complex of claim 1, wherein M is a transition metal.

3. The complex of claim 1, wherein M is iron or manganese.

4. The complex of claim 1, wherein at least one $R_1$ and $R_2$ pair form a ring with the carbon atom to which the $R_1$ and $R_2$ pair is bound.

5. The complex of claim 4, wherein the ring is substituted or unsubstituted and comprises three members, four members, five members, or six members.

6. The complex of claim 1, wherein at least one of $R_1$, $R_2$, or a combination thereof, form a ring together with at least one R substituent on an adjacent carbon atom, E, or Z in the same one of $Y_1$, $Y_2$, $Y_3$, or $Y_4$.

7. The complex of claim 6, wherein the ring is unsubstituted, unsaturated, and mono-substituted or poly-substituted.

8. The complex of claim 1, wherein at least one of R', $R'_1$, $R'_2$, or a combination thereof, comprises a carbon-containing group selected from the group consisting of alkyl, alkenyl, alkynyl, aryl, alkoxy, phenoxy, halogenated alkyl, halogenated aryl, halogenated alkenyl, halogenated alkynyl, perhaloalkyl, perhaloaryl, a cycloalkyl ring, a cycloalkenyl ring, and a heterocyclic ring containing oxygen, nitrogen, or a combination thereof.

9. The complex of claim 1, wherein each of R', $R'_1$, and $R'_2$ is individually selected from the group consisting of hydrogen, deuterium, oxygen, hydroxyl, halogen, a nitrogen-containing group, and a carbon-containing group.

10. The complex of claim 1, wherein
(i) at least one of $R_5$, $R_6$, $R_7$, $R_8$, or a combination thereof, together with at least one R substituent on an adjacent carbon atom in the same one of $Y_1$, $Y_2$, $Y_3$, or $Y_4$, together with an R' substituent on an adjacent Z in the same one of $Y_1$, $Y_2$, $Y_3$, or $Y_4$, or together with a substituent on an adjacent E in the same one of $Y_1$, $Y_2$, $Y_3$, or $Y_4$ form a ring;

(ii) at least one pair selected from the group consisting of a $R_5$ and $R_6$ pair and a $R_7$ and $R_8$ pair, forms a cycloalkyl or cycloalkenyl ring;

(iii) at least one pair selected from the group consisting of a $R_5$ and $R_6$ pair and a $R_7$ and $R_8$ pair, together with at least one R substituent on an adjacent carbon atom in the same one of $Y_1$, $Y_2$, $Y_3$, or $Y_4$, together with an R' substituent on an adjacent Z in the same one of $Y_1$, $Y_2$, $Y_3$, or $Y_4$, or together with a substituent on an adjacent E in the same one of $Y_1$, $Y_2$, $Y_3$, or $Y_4$ form a ring; or a combination of (i), (ii), and (iii).

11. The complex of claim 10, wherein at least one ring is unsubstituted, mono-substituted, or poly-substituted and wherein at least one ring is saturated or unsaturated.

12. The complex of claim 1, wherein at least one of $R_1$, $R_2$, or a combination thereof in at least one of $Y_1$, $Y_2$, $Y_3$, or $Y_4$ is hydrogen or deuterium.

13. The complex of claim 1, wherein Z is nitrogen.

14. The compound of claim 1, wherein M is iron or manganese and Z is nitrogen.

15. The complex of claim 1, wherein each of $Y_1$, $Y_2$, $Y_3$, and $Y_4$, individually is selected from the group consisting of:

16. The complex of claim 1, wherein each of $Y_1$, $Y_2$, $Y_3$, and $Y_4$, individually is selected from the group consisting of:

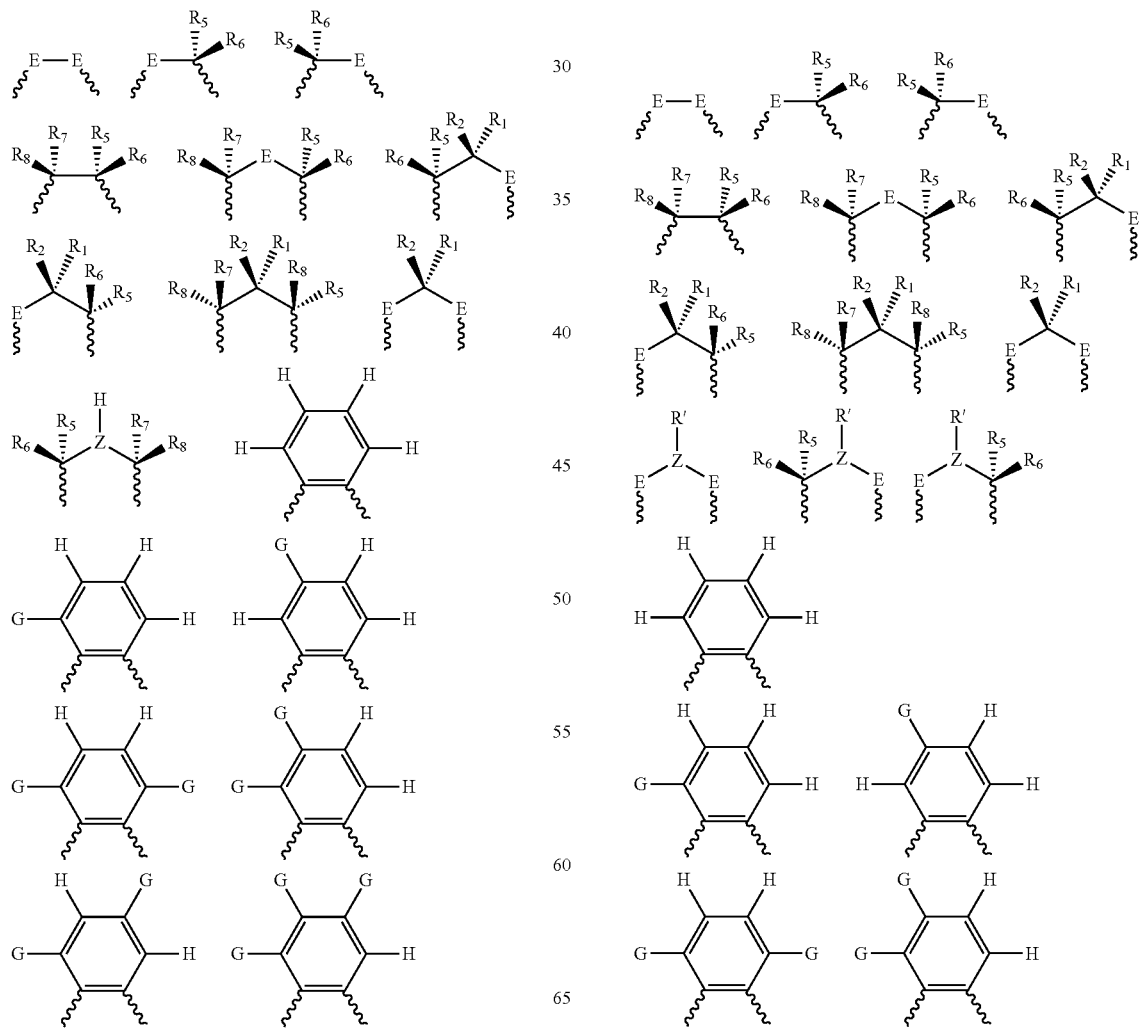

-continued

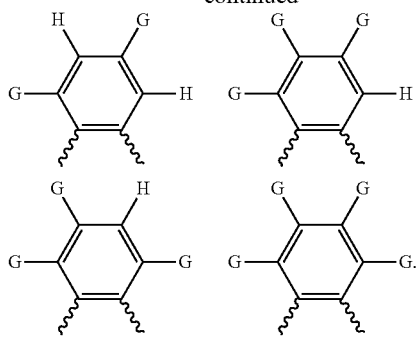

17. The complex of claim 1, wherein at least one of $Y_1$, $Y_2$, $Y_3$, $Y_4$, or a combination thereof, individually is selected from the group consisting of:

-continued

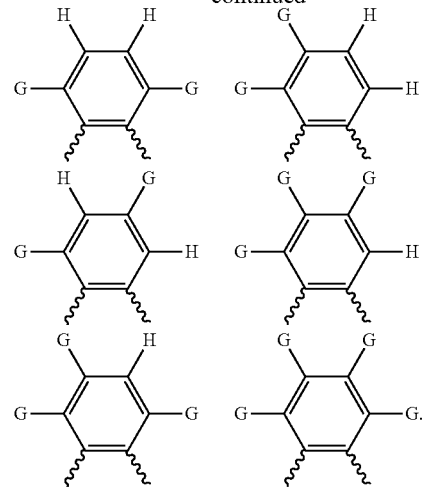

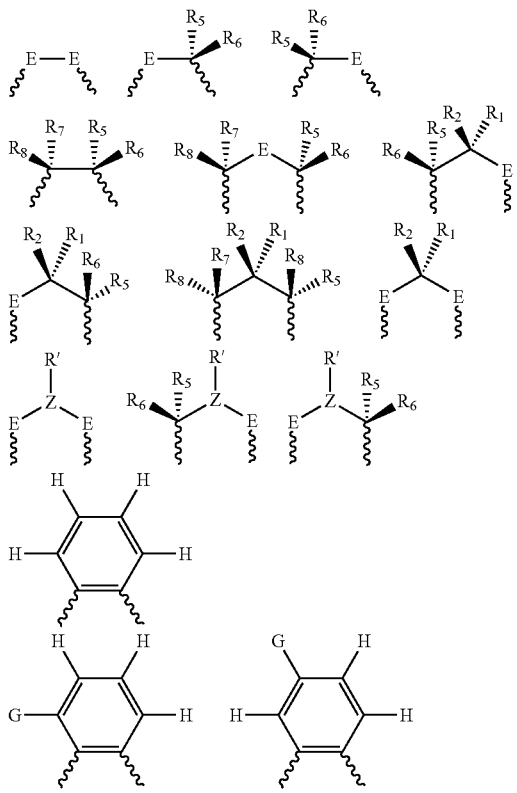

18. The complex of claim 1, wherein when the in-ring atom of E is sulfur, E is selected from the group consisting of $S(=O)_2$, and $S(=O)$.

19. The complex of claim 1, wherein when the in-ring atom of E is phosphorous, E is selected from the group consisting of $P(=O)R'$ and $P(R')_3$.

20. The complex of claim 1, wherein
M is a transition metal;
Z is nitrogen;
when the in-ring atom of E is sulfur, E is selected from the group consisting of $S(=O)_2$, and $S(=O)$; and
when the in-ring atom of E is phosphorous, E is selected from the group consisting of $P(=O)R'$ and $P(R')_3$.

21. The complex of claim 1, wherein every D is directly attached to at least one E.

22. The complex of claim 1, wherein at least D is attached to an R substituent.

23. A process comprising:
performing a catalytic oxidation reaction upon a target utilizing the complex recited in claim 1 in the presence of an oxidant.

24. The process of claim 23 wherein the oxidant is selected from the group consisting of halogen, halogen oxide, halogenoxoanion, elemental halogen, a peroxy compound, hydrogen peroxide, oxygen, air, ozone, oxygen in the presence of an adjunct and combinations thereof, an electrode with or without a mediating compound that is regenerated by an electrode; elemental chlorine, chlorine oxide, chlorine oxoanion, chlorine dioxide, hypochlorite, acidic species thereof and combinations thereof.

* * * * *